(12) United States Patent
Yost et al.

(10) Patent No.: US 9,194,744 B2
(45) Date of Patent: Nov. 24, 2015

(54) TRANSMISSION QUANTIFICATION OF OPEN PATH FTIR SPECTRA WITH TEMPERATURE COMPENSATION

(75) Inventors: Michael G. Yost, Mercer Island, WA (US); Robert S. Crampton, Seattle, WA (US)

(73) Assignee: University of Washington, Seattle, WA (US)

( * ) Notice: Subject to any disclaimer, the term of this patent is extended or adjusted under 35 U.S.C. 154(b) by 831 days.

(21) Appl. No.: 12/993,036

(22) PCT Filed: May 14, 2009

(86) PCT No.: PCT/US2009/043951
§ 371 (c)(1),
(2), (4) Date: Jan. 20, 2011

(87) PCT Pub. No.: WO2009/140492
PCT Pub. Date: Nov. 19, 2009

(65) Prior Publication Data
US 2011/0112772 A1      May 12, 2011

Related U.S. Application Data

(60) Provisional application No. 61/053,894, filed on May 16, 2008.

(51) Int. Cl.
*G01N 21/15* (2006.01)
*G01N 21/01* (2006.01)
(Continued)

(52) U.S. Cl.
CPC .... *G01J 3/42* (2013.01); *G01J 3/28* (2013.01); *G01N 21/3504* (2013.01); *G01N 2021/3595* (2013.01)

(58) Field of Classification Search
CPC .......................................................... G01J 3/00
USPC ............... 702/22, 24, 25, 179, 182, 183, 189; 250/343, 341.7; 356/325, 343; 600/328
See application file for complete search history.

(56) References Cited

U.S. PATENT DOCUMENTS

| 4,652,755 A | * | 3/1987 | Solomon et al. | 250/341.7 |
| 4,805,623 A | * | 2/1989 | Jobsis | 600/328 |

(Continued)

FOREIGN PATENT DOCUMENTS

| JP | 10-206236 A | 8/1998 |
| JP | 2000-346801 A | 12/2000 |
| WO | WO 2009/140492 A2 | 11/2009 |

OTHER PUBLICATIONS

Arnott, W. P., C. Schmitt, et al. (1997). "Droplet size spectra and water-vapor concentration of laboratory water clouds: Inversion of Fourier transform infrared (500-5000 cm(-1)) optical-depth measurement." Applied Optics 36(21): 5205-5216.

(Continued)

*Primary Examiner* — John Breene
*Assistant Examiner* — Felix Suarez
(74) *Attorney, Agent, or Firm* — Kilpatrick Townsend and Stockton LLP

(57) ABSTRACT

A transmission quantification approach that is effective at quantifying the concentration of key atmospheric gases, including water vapor and methane, does not require a background spectrum and is immune to changes between background and absorbance spectra. By using local minima and maxima in transmission of a target gas, this approach creates two spectral arrays as long as a single beam input spectra. One of these spectral arrays represents the points in wave-number space that are less absorbing points, and the other represents the more absorbing points. A concentration for a given gas is calculated by determining what reference concentration creates a residual after division by a pure gas spectrum that forces these two arrays to converge.

24 Claims, 23 Drawing Sheets

(51) Int. Cl.
  G01N 21/17    (2006.01)
  G06F 5/00     (2006.01)
  G01J 3/42     (2006.01)
  G01J 3/28     (2006.01)
  G01N 21/3504  (2014.01)
  G01N 21/35    (2014.01)

(56) References Cited

U.S. PATENT DOCUMENTS

| | | | | |
|---|---|---|---|---|
| 4,928,015 | A * | 5/1990 | Butler et al. | 250/343 |
| 5,206,701 | A * | 4/1993 | Taylor et al. | 356/325 |
| 5,822,058 | A * | 10/1998 | Adler-Golden et al. | 356/303 |
| 6,748,334 | B1 * | 6/2004 | Perez et al. | 702/24 |
| 6,862,535 | B2 * | 3/2005 | Binder | 702/24 |
| 6,885,965 | B2 | 4/2005 | Butler et al. | |
| 2003/0070451 | A1 | 4/2003 | Ouellet et al. | |

OTHER PUBLICATIONS

Bacsik, Z., J. Mink, et al. (2004). "FTIR spectroscopy of the atmosphere. I. Principles and methods." Applied Spectroscopy Reviews 39(3): 295-363.
Blackwood, T. R. (1999). "An evaluation of flare combustion efficiency using open-path Fourier transform infrared technology." Annu. Meet. Exhib. Proc. CD-ROM—Air Waste Manage. Assoc., 92nd: 5445-5455.
Bradley, K. S., K. B. Brooks, et al. (2000). "Motor vehicle fleet emissions by OP-FTIR." Environmental Science & Technology 34(5): 897-899.
Childers, J. W. (1993). "Resolution considerations in long-path, open-path FT-IR spectrometry." Proc., Annu. Meet.—Air Waste Manage. Assoc. 86TH(vol. 8):93/RA/121 05, 11 pp.
Childers, J. W., E. L. Thompson, et al. (2001). "Multi-pollutant concentration measurements around a concentrated swine production facility using open-path FTIR spectrometry." Atmospheric Environment 35(11): 1923-1936.
Childers, J. W., G. M. Russwurm, et al. (1995). "Quality assurance considerations in a long-term FT-IR monitoring program." Proc. SPIE-Int. Soc. Opt. Eng. 2365(Optical Sensing for Environmental and Process Monitoring): 389-95.
Childers, J. W., G. M. Russwurm, et al. (1997). "QA/QC issues in OP/FTIR monitoring." Proc., Annu. Meet.—Air Waste Manage. Assoc. 90th: RA14107/1-RA14107/10.
Connes, P. (1984). "Early history of fourier transform spectroscopy." Infrared Physics 24(2-3): 69-93.
Crampton, R.S. (2007) "Transmission quantification for open path Fourier transform spectroscopy with temperature compensation." Ph.D. thesis, University of Washington, Seattle, Washington.
Drescher, A. C., D. Y. Park, et al. (1997). "Stationary and time-dependent indoor tracer-gas concentration profiles measured by OP-FTIR remote sensing and SBFM-computed tomography." Atmospheric Environment 31(5): 727-740.
Espinoza, L. H., T. M. Niemdzyk, et al. (1998). "Generation of synthetic background spectra by filtering the sample interferogram in FT-IR." Applied Spectroscopy 52(3): 375-379.
Farhat, S. K. and L. A. Todd (2000). "Evaluation of open-path FTIR spectrometers for monitoring multiple chemicals in air." Appl Occup Environ Hyg 15(12): 911-23.
Francis, P., C. Chaffin, et al. (1996). "Remote determination of SiF4 in volcanic plumes: A new tool for volcano monitoring." Geophysical Research Letters 23(3): 249-252.
Gamiles, D. S., M. Rodgers, et al. (1997). "Evaluation of innovative air monitoring technologies for the measurement of ambient concentrations of ozone and its precursors at the 1996 summer olympics." Proc. SPIE-Int. Soc. Opt. Eng. 3107(Remote Sensing of Vegetation and Water, and Standardization of Remote Sensing Methods): 56-63.
Giese-Bogdan, S. and S. P. Levine (1996). "International diffusion of open path FTIR technology and air monitoring methods: Taiwan (Republic of China)." Journal of the Air & Waste Management Association 46(8): 761-764.
Giese-Bogdan, S., S. P. Levine, et al. (1999). "Application of the shifting method as a technique to correct for the background in quantitative analysis by open-path FTIR." Journal of the Air & Waste Management Association 49(2): 114-124.
Griffith, D. W. T. (1996). "Synthetic Calibration and Quantitative Analysis of Gas-Phase FT-IR Spectra." Applied Spectroscopy 50(1): 59-70.
Grim, L., T. C. Gruber, Jr., et al. (1995). "Generation of synthetic remote FTIR interferograms." Proc. SPIE-Int. Soc. Opt. Eng. 2366: 224-32.
Hashmonay, R. A. and M. G. Yost (1999). "On the application of Open-Path Fourier Transform Infra-Red spectroscopy to measure aerosols: Observations of water droplets." Environmental Science & Technology 33(7): 1141-1144.
Hong, D. W., G. S. Heo, et al. (2004). "Application of the open path FTIR with COL1SB to measurements of ozone and VOCs in the urban area." Atmospheric Environment 38(33): 5567-5576.
Horrocks, L. A., C. Oppenheimer, et al. (2001). "Open-path Fourier transform infrared spectroscopy of SO2: An empirical error budget analysis, with implications for volcano monitoring." Journal of Geophysical Research-Atmospheres 106(D21):27647-27659.
Horrocks, L., M. Burton, et al. (1999). "Stable gas plume composition measured by OPFTIR spectroscopy at Masaya Volcano, Nicaragua, 1998-1999." Geophysical Research Letters 26(23): 3497-3500.
International Search Report and Written Opinion for corresponding International Patent Application No. PCT/US2009/043951 dated Dec. 28, 2009, 11 pages.
Kagann, R. H. and E. Ringler (1994). "The use of temperature dependent calculations of spectra as references for open-path FTIR measurements." Proc., Annu. Meet.—Air Waste Manage. Assoc. 87th(vol. 1B, Atmospheric Sciences & Ozone): 1-9, 94-RA106 05.
Kagann, R. H. and O. A. Simpson (1990). "Open-path FTIR measurements of gaseous emissions from a chemical plant wastewater treatment basin." Proc.—A&WMA Annu. Meet. 83rd(vol. 5): 90-86. 7.
Kagann, R. H., C. D. Wang, et al. (1999). "Open-path FTIR measurement of criteria pollutants and other ambient species in an industrial city." Proc. SPIE-Int. Soc. Opt. Eng. 3534(Environmental Monitoring and Remediation Technologies): 140-149.
Kagann, R. H., W. L. Woturski, et al. (1999). "Measurement of ambient air quality in urban settings using open-path FTIR." Annu. Meet. Exhib. Proc. CD-ROM—Air Waste Manage. Assoc., 92nd: 5415-5430.
Kuttler, W., T. Lamp, et al. (2002). "Summer air quality over an artificial lake."Atmospheric Environment 36(39-40): 5927-5936.
Learning, C. C. f. N. M. T. a. (2007). "Understanding Spectroscopy." Retrieved Oct. 12, 2007, from http://www.columbia.edu/ccnmtl/draft/dbeeb/chemudl/spectrometer.html.
Li, Y., Wang, J. D. et al. (2002). "Monitoring leaking gases by OP-FTIR remote sensing." Journal of Environmental Science and Health Part a-Toxic/Hazardous Substances & Environmental Engineering 37(8): 1453-1462.
Mastalerz, M., M. Glikson, et al. (1998). "Analysis of atmospheric particulate matter; application of optical and selected geochemical techniques." International Journal of Coal Geology 37(1-2): 143-153.
McLaren, S. L., D. H. Stedman, et al. (1996). "Detection of chemical agents by open path FTIR spectroscopy." Book of Abstracts, 211th ACS National Meeting, New Orleans, LA, Mar. 24-28: ENVVR-059.
Michelson, A. A. (1891). "Visibility of Interference-Fringes in the focus of a telescope." Phil. Mag. 31(5): 256.
Morrison, P. W. J. and O. Taweechokesupsin (1998). "Calculation of Gas Spectra for Quantitative Fourier Transform Infrared Spectrscopy of Chemical Vapor Deposition." Journal of the Electrochemical Society 145(No. 9): 3212-3219.
Park, D. Y. (1996). Tomographic Reconstruction of Air contaminant concentration maps using an OP-FTIR spectrometer. Occupational Health. Ann Arbor MI, University of Michigan. Doctor of Public Health: 262.
Park, D. Y., J. A. Fessler, et al. (2000). "Tomographic reconstruction of tracer gas concentration profiles in a room with the use of a single OP-FTIR and two iterative algorithms: ART and PWLS." Journal of the Air & Waste Management Association 50(3): 357-370.

(56) References Cited

OTHER PUBLICATIONS

Park, D. Y., M. G. Yost, et al. (1997). "Evaluation of virtual source beam configurations for rapid tomographic reconstruction of gas and vapor concentrations in workplaces." Journal of the Air & Waste Management Association 47(5): 582-591.
Phillips, B. and G. M. Russwurm (1998). An Open Path FTIR Data Reduction Algorithm with Atmospheric Absorbtion Corrections:the NONLIN code. SPIE Conference on Environmental Monitoring and Remediation technologies, Boston MA, SPIE.
Phillips, B. J. (2001). "IR spectral modeling and reference spectra generation with ETrans." Proc. Air Waste Manage. Assoc. Annu. Conf. Exhib., 94th: 3093-3108.
Phillips, B., D. Brown, et al. (1997). "Innovative FTIR open path data reduction algorithm." Meas. Toxic Relat. Air Pollut., Proc. Spec. Conf. 2: 586-596.
Phillips, B., D. Brown, et al. (1997). "Non-linear FTIR open path data reduction algorithm." Proc. SPIE-Int. Soc. Opt. Eng. 3106(Spectroscopic Atmospheric Monitoring Techniques): 33-43.
Phillips, B., R. Moyers, et al. (1995). "Improved FTIR open path remote sensing data reduction technique." Proc. SPIE-Int. Soc. Opt. Eng. 2365(Optical Sensing for Environmental and Process Monitoring): 374-88.
Pollard, M. J., P. R. Griffiths, et al. (2007). "Investigation of the Christiansen effect in the mid-infrared region for airborne particles." Applied Spectroscopy 61(8): 860-866.
Ren, Y. B., Y. Li, et al. (2005). "Reconstruction of air contaminant concentration distribution in a two-dimensional plane by computed tomography and remote sensing FTIR spectroscopy." Journal of Environmental Science and Health Part a-Toxic/Hazardous Substances & Environmental Engineering 40(3): 571-580.
Rodler, J., P. J. Sturm, et al. (2001). "Measurements with UV-DOAS in a street tunnel for validation of emission factors for road vehicles." Proc. SPIE-Int. Soc. Opt. Eng. 4169(Sensors, Systems, and Next-Generation Satellites IV): 422-431.
Rothman, L. S., C. P. Rinsland, et al. (1998). "The HITRAN molecular spectroscopic database and HAWKS (HITRAN Atmospheric Workstation): 1996 edition." Journal of Quantitative Spectroscopy & Radiative Transfer 60(5): 665-710.
Russwurm, G. M. a. C., J.W., (1995). FTIR Open-Path Monitoring Guidance Document. US-EPA:. Research Triangle Park. SP-4420-95-04.
Russwurm, G. M. and B. Phillips (1999). "Effects of a nonlinear response of the Fourier-transform infrared open-path instrument on the measurements of some atmospheric gases." Applied Optics 38(30): 6398-6407.
Russwurm, G. M. and J. W. Childers (1996). "Compendium method TO-16. Long path open path FTIR method for monitoring ambient air." Proc., Annu. Meet.—Air Waste Manage. Assoc. 89th: mp504/1-mp504/6.
Russwurm, G. M. and J. W. Childers (1996). FT-IR open-path monitoring guidance document, ManTech Environ. Technol., Inc., Research Triangle Park, NC, USA.: 168 pp.
Samanta, A. and L. A. Todd (2000). "Mapping chemicals in air using an environmental Cat scanning system: evaluation of algorithms." Atmospheric Environment 34(5): 699-709.
Talwar, D.N. (2003) "Characterisation of intrinsic and compensated defect microstructures in dilute III-V-N alloys," in: Circuits, Devices and Systems, IEEE Proceedings, 150(6):529-536.
Todd, L. A., M. Ramanathan, et al. (2001). "Measuring chemical emissions using open-path Fourier transform infrared (OP-FTIR) spectroscopy and computer-assisted tomography." Atmospheric Environment 35(11): 1937-1947.
Tomasko, M. S. and L. A. Todd (1995). "Evaluating open-path FTIR spectrometer data using different quantification methods, libraries, and background spectra obtained under varying environmental conditions." Proc. SPIE-Int. Soc. Opt. Eng. 2365(Optical Sensing for Environmental and Process Monitoring): 411-17.
Vogt, F. (2006). "Trends in remote spectroscopic sensing and imaging—experimental techniques and chemometric concepts." Curr. Anal. Chem. 2(2): 107-127.
Webb, J. D., K. R. Loos, et al. (1996). "Initial applications of open path FTIR to three Shell Oil facilities—a chemical plant, a refinery and a natural gas processing plant." Proc. SPIE-Int. Soc. Opt. Eng. 2883(Optical Remote Sensing for Environmental and Process Monitoring): 315-322.
Weber, K., A. Ropertz, et al. (2004). "Measurement and analysis of the air quality within the region of an urban green area using optical remote measurement techniques." Gefahrstoffe Reinhaltung Der Luft 64(6): 271-279.
Wu, C. F., M. G.Yost, et al. (2003). "Applying open-path FTIR with a bi-beam strategy to evaluate personal exposure in indoor environments: Experimental results of a validation study." AIHA Journal 64(2): 181-188.
Wu, C. F., M. G. Yost, et al. (2003). "Path concentration profile reconstruction of optical remote sensing measurements using polynomial curve fitting procedures." Atmospheric Environment 37(14): 1879-1888.
Wu, C.-F., Y.-L. Chen, et al. (2007). "Applying open-path Fourier transform infrared spectroscopy for measuring aerosols." J. Environ. Sci. Health, Part A: Toxic/Hazard. Subst. Environ. Eng. 42(8): 1131-1140.
Wu, R. T., S.-Y. Chang, et al. (1995). "FTIR remote sensor measurements of air pollutants in the petrochemical industrial park." Proc. SPIE-Int. Soc. Opt. Eng. 2552(Pt. 2, Infrared Technology XXI): 719-27.
Yost, M. G., R. A. Hashmonay, et al. (1999). "Estimating maximum concentrations for open path monitoring along a fixed beam path." Journal of the Air & Waste Management Association 49(4): 424-433.
Zwicker, J. O. and A. J. Mechling (1999). "Use of OP-FTIR monitoring to determine downwind concentrations of methyl bromide and chloropicrin resulting from fumigation of strawberry fields." Annu. Meet. Exhib. Proc. CD-ROM—Air Waste Manage. Assoc., 92nd: 5384-5396.

\* cited by examiner

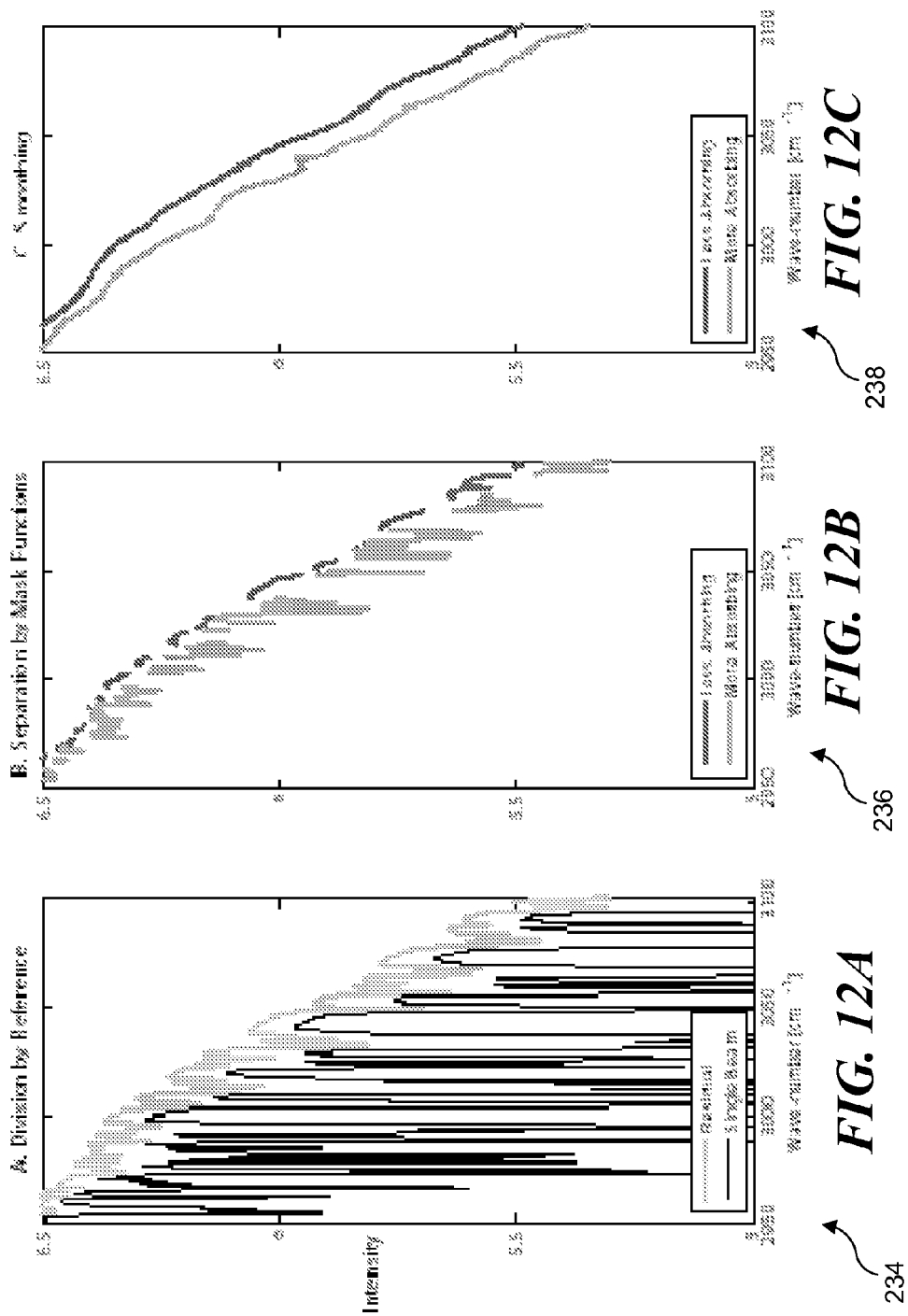

TRANSMISSION QUANTIFICATION OF OPEN PATH FTIR SPECTRA WITH TEMPERATURE COMPENSATION

RELATED APPLICATIONS

This application is based on a prior provisional application Ser. No. 61/053,894, filed on May 16, 2008, the benefit of the filing date of which is hereby claimed under 35 U.S.C. §119(e).

BACKGROUND

Open Path Fourier Transform Infrared (OP-FTIR) Spectroscopy is a remote sensing air monitoring technique that was first used in the 1960's for the purpose of measuring the atmospheres of earth and other planets. It is based on the traditional line of FTIR spectrometers, which started with Michelson's invention of interferometry in 1891. FTIR spectroscopes have been used for the evaluation of solid, liquid, and gas analytes since that time. Bench-top gas FTIR spectrometers are the most similar spectrometers to OP-FTIR spectrometers, as both are designed to measure the infrared spectra of gases in a sample space by way of interferometry. The bench-top FTIR is used to analyze gas analytes in an enclosed compartment or cell. The cell can be purged with nitrogen or even evacuated to obtain a background spectrum, and then filled with the analyte for analytical spectrum measurement.

The concept of a background spectrum is central to spectroscopy. In the simplest terms, Beer's law relates the amount of a substance present in an analytical sample to the amount of light absorbed by the analytical beam. The substance absorbs light, so more of the substance means less light passes through the sample space. To understand what is in an analytical spectrum, the light that is absorbed or not transmitted is measured. To make this measurement, it is necessary to know how much light would be there without the analyte present. The background spectrum ($I_0$) ideally represents what the spectrum would look like without the analyte. The issue is trivial with a bench-top unit, since the cell can be filled with nitrogen, which has almost no features in the mid-infrared region of the spectrum.

The OP-FTIR spectrometer is radically different, since its sampling volume is the open atmosphere. The open atmosphere cannot be put into a cell, and the necessary innovation of OP-FTIR was the use of the sun or another distant infrared source enabling for the first time, the powerful FTIR technique to be used as a remote sensing technology. This same remoteness of the environment being evaluated prevents the sample space from being filled with a vacuum, nitrogen, or any other non-infrared absorbing gas, and as a result, the background problem is created. Under such uncontrolled conditions, it is not possible to measure what would be in an open path without the analyte present.

The limitations in obtaining the ideal background spectrum have not prevented OP-FTIR from being useful for monitoring air pollutants in a variety of terrestrial environmental and workplace situations. These include the monitoring of hazardous waste sites, waste lagoons from confined animal feeding operations, smog analysis, volcanic emissions, and chemical plants. The transportability of the measurement system has allowed it to be flexibly used for mobile source monitoring, stack monitoring, workplace monitoring, and urban air pollution monitoring. The most common gaseous air pollutants regulated by the U.S. Environmental Protection Agency (US-EPA), termed "criteria" pollutants, are lead, particulate matter, $SO_2$, CO, ozone ($O_3$), $NO_2$, and NO. All of these gases can be detected by OP-FTIR, and some work has been done on detecting particulate matter, a non-gaseous criteria pollutant, as well. These gases typically are monitored by a suite of instruments, using one for $O_3$, one for NO and $NO_2$, one for $SO_2$, and a fourth separate instrument for CO.

The 1990 Clean Air Act Amendments expanded the US-EPA list of air pollutants by adding 189 Hazardous Air Pollutants (HAPs) to the original criterion air pollutants as potentially dangerous compounds that should be monitored. OP-FTIR spectroscopy has proven particularly useful for the identification and quantification of a number of these compounds due to their unique infrared absorption features. Many of these compounds are larger organic molecules and would require capture in a bag, charcoal tube or canister, and transport to a lab for analysis by gas chromatography or mass spectroscopy. These methods are accurate but very costly for each sample and usually not able to obtain time resolution better than an hour. OP-FTIR can theoretically simultaneously monitor for many of these compounds, along with the criterion pollutants, over distances on the scale of hundreds of meters, and in real time.

Fence line and area sources have been the focus of most applications of this technology due to the nature of a beam average concentration. Since the sample space is spread along the beam-path, the concentration calculated represents a path integral measurement. The path integral measurement, which represents the total number of molecules in the path, can be converted into a path average measurement by dividing by the path-length. This conversion is beneficial when trying to calculate a flux from an area source with irregular source strength and/or changing wind direction. Another benefit is the speed of data acquisition; OP-FTIR offers much better time resolved data than other techniques, such as evacuated SUMMA™ canisters analyzed by gas chromatography-mass spectrometry (GC-MS), which collect samples typically integrated over several hours. With OP-FTIR, it is possible to obtain valid spectra every few minutes, and to quantify these spectra for any combination of the aforementioned gases. In theory, any gaseous compound having a dipole moment can be detected in this manner. The quantification of several species simultaneously is typically done using Beer's Law and classical least squares techniques. The resulting output data are in units of parts per million-meters (ppm-m) and represent the fence line or ambient concentration measurement integrated over the entire beam path. Both stable and unstable compounds can be measured with OP-FTIR in this way, since no sample handling or storage is involved. This benefit makes OP-FTIR a useful tool for monitoring changes in reactive atmospheric gases and for quantifying reaction products that play a role in urban air pollution.

Cost also is an important consideration when selecting a sampling method; the initial cost of an OP-FTIR is considerable (~$100,000 when done by Cerex Environmental Services in 2007) but has been decreasing in recent years. Yet, when compared to the cost of several monitoring devices that a single OP-FTIR could be replacing, and the lack of sample transport and lab analysis costs for the HAPs, the total operational cost of OP-FTIR can be competitive with conventional sampling for many applications.

The main advantages of OP-FTIR can be summarized as follows:

1. Flexibility for simultaneous monitoring of multiple gases;
2. Fast sample collection & analysis;
3. Average over path less susceptible than a point sample to a small spike in space;

4. Long-term cost is comparable to or cheaper than other methods; and

5. Measurement of reactive species that cannot be captured and analyzed later.

Despite these advantages, the full promise of OP-FTIR has not yet been fulfilled. Although OP-FTIR has many advantages as described above, its optimal use is constrained by two key problems. First, the instrument is characterized by an inherent inability to determine the physical location or magnitude of the maximum point concentration of a pollutant along the beam path. The path average ppm-meters quantity is helpful in determining fluxes for area sources, but unable to determine a peak concentration in space. This "spatial resolution problem" has been the subject of considerable research and can be solved by using multiple beam paths.

Second, the OP-FTIR requires a true background spectrum to calculate concentration using the Beer Lambert law. As mentioned above, this "background problem" stems partially from the inability to control environmental factors (mainly temperature and relative humidity (RH)) in an open sampling volume. Additional factors that contribute to the background problem are slight changes in instrumental parameters such as resolution and spectral shift.

The spatial resolution problem exists because the data collected by open path instruments are in the form of an integral of the concentration along the entire beam path, expressed in ppm-meters, which means that a one meter wide plume of 100 ppm concentration at any point along the path-length would create the same instrument response as a 100 meter wide plume of one ppm. Effectively, the only concentration value that can be obtained from a single path integrated measurement is the average over the entire beam path. Since health effects depend greatly on the air concentration at a particular location, for exposure assessment in workplaces or near source and fence line monitoring applications, this lack of spatially resolved concentration information is unacceptable. However, by combining data from multiple beam paths of different lengths, it becomes possible to describe the spatial concentration distribution over a desired sampling space.

Ambient monitoring for urban air pollution applications should not be affected by spatial resolution, since the pollutants typically are well mixed on a scale of hundreds of meters. Therefore, the lack of spatial resolution is of little consequence for this situation. However, urban air monitoring often requires monitoring of trace compounds with very low detection limit goals (i.e., the monitoring instrumentation must have great sensitivity), and consequently, can be affected by interference and fluctuations in light transmission due to variations in the normal constituents of the atmosphere in the beam path. The $I_0$ or background spectrum determination has been a serious problem and the subject of substantial research. Water vapor, $CO_2$, particles, and slight variations of instrument performance can all affect the data and make a particular analytical spectrum inappropriate for a given background spectrum. These issues can severely degrade detection limits and lead to an apparent increase in instrument noise.

The OP-FTIR "background problem" comprises many parameters. A single beam spectrum is affected by numerous environmental and instrumental factors. The method is based upon the differences between $I_0$ and $I_A$ caused by the target gas. All of the other factors can also change between $I_0$ and $I_A$. Essentially, what is needed to solve this problem is a spectrum other than the analytical spectrum that is identical to the analytical spectrum, except for the lack of target gases.

Accordingly, it would be desirable to address the background problem through the use of single-beam spectra for determining temperature and concentration of water and other gases for each analytical spectrum. In OP-FTIR spectroscopy, the water vapor interference and its temperature dependence are a subset of this background problem that can be of particular difficulty. Water vapor is always present in the atmosphere, so it is a background issue. The amount of water vapor present is also usually changing at a rate that makes it an interfering gas as well, and is at the percent level, which is orders of magnitude more than any pollutant. Thus, a small error in the calculation of water vapor concentration can result in a large error in the concentration of an analyte. Typically, interfering gases are included in the quantification method, and their concentrations are calculated along with the target gases. However, since water vapor is such a dominant absorber, it is best to use a background spectrum having a water content that is as close to the expected level as possible. This approach does not preclude the need to use water in the quantification method as an interfering species.

Water vapor has absorption features that interfere with potential target gas absorption in most of the usable bandwidth of an FTIR. Bench-top spectrometers have had to deal with this problem since their inception. Even the water vapor contained in a few inches of ambient air within a sample space can cause limitations. This problem is magnified for OP-FTIR instruments because their path-lengths are longer. Water vapor content is often the limiting factor for the maximum path-length for a given part of the spectrum. The band from $1200\ cm^{-1}$ to $1800\ cm^{-1}$ contains important features for many gases, but is unusable in OP-FTIR due to the water vapor absorption. Deuterated (heavy) water (HDO) molecules that include a deuterium hydrogen isotope as one of the two hydrogen atoms represent only 1/8,000 of water molecules in the atmosphere. Even so, the HDO features are clearly seen in OP-FTIR single beams due to the magnitude of water vapor in a typical path. FIGS. 1A and 1B show that water vapor absorbs in the entire working range from $400\ cm^{-1}$ to $4,000\ cm^{-1}$.

In an exemplary infrared absorption spectrum graph 100 (and a more detailed graph 100a shown respectively in and FIGS. 1A and 1B, hundreds of individual absorption lines with great variation in their magnitude are displayed. As will be evident in graph 100a, in FIG. 1B, the absorbance of water vapor in air is never actually zero. The tails of all of the lines in the mid-infrared spectrum and beyond add to form a continuum spectrum. Thus, even between lines, there is some absorption by water vapor.

FIG. 2 is an exemplary graph 110 illustrating the transmittance spectrum of water vapor in air, which shows that the plot never quite reaches 100% transmission (transmittance of 1) between lines, even at the relatively short and dry path of 64 meters and 10,000 ppm $H_2O$. This lack of points with 100% transmission leads to difficulty in some methods of creating a background from the field spectrum. These methods for creating backgrounds depend on interpolating between absorption-free points on the spectrum without water absorption.

Water molecules absorb infrared radiation by entering higher rotational and vibrational energy states. This phenomenon creates the complex infrared spectral features. At any specific ambient temperature, the ratios of water molecules in the different energy states reach a unique equilibrium. Because the spectral lines are a function of the initial energy state distribution, the infrared spectrum of water vapor is considerably temperature dependent. The differences in the spectrum that result from temperature variation at a given concentration can exceed the instrument noise and the absorption of target gases. Therefore, it is crucial to have a water reference and/or water containing background with the correct temperature as well as water concentration for each analytical spectrum. An acceptable background spectrum must have these two parameters correctly represented, as well as any variable instrument parameters, to properly account for the water vapor that is present.

The answer to this problem has increasingly been the use of synthetic spectra created with the high-resolution transmission molecular absorption database (HITRAN) or another spectral database. HITRAN is a compilation of spectroscopic parameters (i.e., a database) that a variety of computer codes use to predict and simulate the transmission and emission of light in the atmosphere. The creation of this database is a long-running project started by the Air Force Cambridge Research Laboratories (AFCRL) in the late 1960's in response to the need for detailed knowledge of the infrared properties of the atmosphere. It is unreasonable to try to create a comprehensive library by collecting water vapor spectra over the entire range of concentrations, path-lengths, and temperatures that would be needed in the field. Others have done considerable work with this idea and have created software such as "NONLIN" and "MALT," among others, that synthetically generates reference spectra for each analytical spectrum for several gases including water and $CO_2$. The ambient temperature is an important input to all of these models that the user must measure carefully for each spectrum. Temperature, however, can vary over distances of several hundreds of meters, especially over a water surface or other differing surfaces. Many applications of OP-FTIR have beam-paths of this length over non-homogeneous surfaces. Errors in the temperature input to these models results in errors in the size and shape of spectral features in the synthetic spectra. However, it is clear that developing an approach for accurately determining the true average temperature of the molecules along the entire beam would result in more accurate synthetic spectra and better quantification of the gases in the beam, which can be invaluable in many applications of OP-FTIR.

SUMMARY

Accordingly, an exemplary method has been developed for automatically determining an actual concentration of a gas in an path using an optically derived analytical spectrum for the path, and using transmittance reference data for the gas. The transmittance data comprise a plurality of transmittance spectrum for each of a corresponding plurality of different concentrations of the gas. The method includes the steps of dividing the analytical spectrum by the transmittance spectrum for each of the plurality of different concentrations of the gas, to determine residual spectra for the different concentrations of the gas. Using mask functions that are derived from the transmittance reference data, the residual spectra are separated into absorbing and non-absorbing residual spectra. The absorbing and non-absorbing residual spectra are then smoothed, to produce smoothed absorbing and non-absorbing residual spectra. An actual concentration of the gas in the path is determined by identifying the concentration of the gas for which a difference between the smoothed absorbing and non-absorbing residual spectra is a minimum.

The method can further include the step of determining an absorbing mask function and a non-absorbing mask function from the reference transmittance data. Then, the step of determining the absorbing mask function and the non-absorbing mask function can include the step of comparing each transmittance point of a reference transmittance spectrum to a floating median of transmittance within a (moving) window around that transmittance point. The absorbing mask is based on the transmittance points that are on one side of the floating median, and the non-absorbing mask is based on the transmittance points on an opposite side of the floating median. The residual spectra can be multiplied by the mask functions, to produce the absorbing and non-absorbing residual spectra.

In addition, the method can include the step of removing specific values (e.g., zeroes) after multiplying the residual spectra by the mask functions, to produce the absorbing and non-absorbing residual spectra. However, other options exist for this step. For example in the floating median split, it is possible to remove the median value before proceeding with the quantification.

The step of determining the actual concentration of the gas in the path by identifying the concentration of the gas for which a difference between the smoothed absorbing and non-absorbing residual spectra is a minimum can comprise the step of subtracting the smoothed absorbing residual spectra from the non-absorbing smoothed spectra for each of the different concentrations of the gas, to determine a differential intensity. The actual concentration can be determined to be the concentration of the gas that minimizes the differential intensity.

Further, the transmittance reference spectra can be interpolated using the actual concentration of the gas, to create an interpolated transmittance spectra for the gas. Then, the analytical spectrum can be divided by the interpolated transmittance reference spectrum to determine a new residual spectrum that can be used for determining a concentration of a different gas in the path.

The step of creating the analytical spectrum can be implemented by directing light along the path and obtaining the analytical spectrum using a spectrometer selected from a group of spectrometers consisting of a Fourier transform infrared spectrometer; an ultraviolet absorption spectrometer; a visible light spectrometer; and a Raman spectrometer.

Another aspect of the present novel approach is directed to a medium including machine readable and executable instructions for carrying out a plurality of functions to automatically determine an actual concentration of a gas in an path using an optically derived analytical spectrum for the path and transmittance reference data for the gas. The plurality of functions are generally consistent with the steps of the method discussed above.

Still another aspect is directed to a system for automatically determining an actual concentration of a gas in an path using an optically derived analytical spectrum for the path and transmittance reference data for the gas. The system includes a memory in which are stored the transmittance data, and a plurality of machine executable instructions, an input port coupled to receive an input signal corresponding to the analytical spectrum, and a processor that is coupled to the memory and the input port. The processor executes the machine executable instructions to carry out a plurality of functions that are again, generally consistent with the steps of the method discussed above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 10:
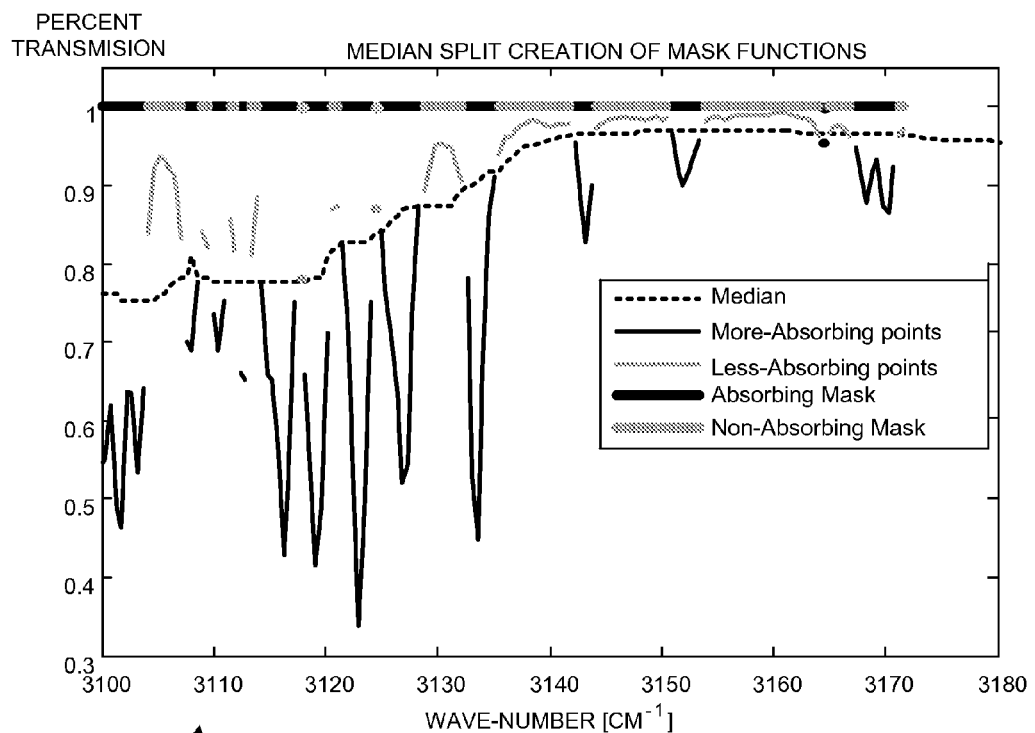
Figure 11A:
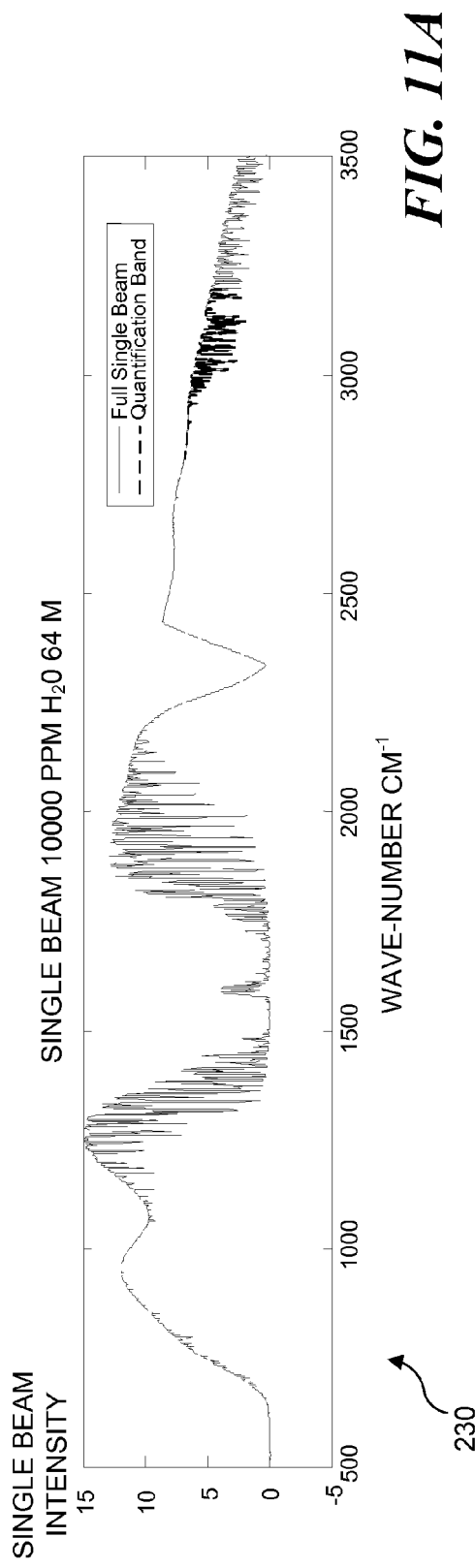
Figure 11B:
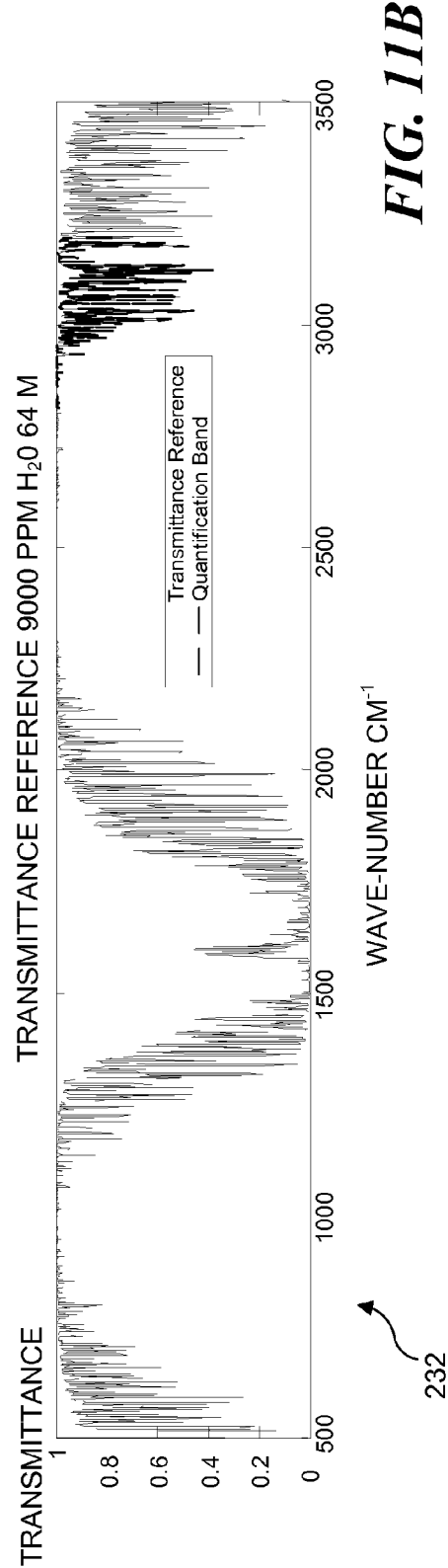
Figure 13:
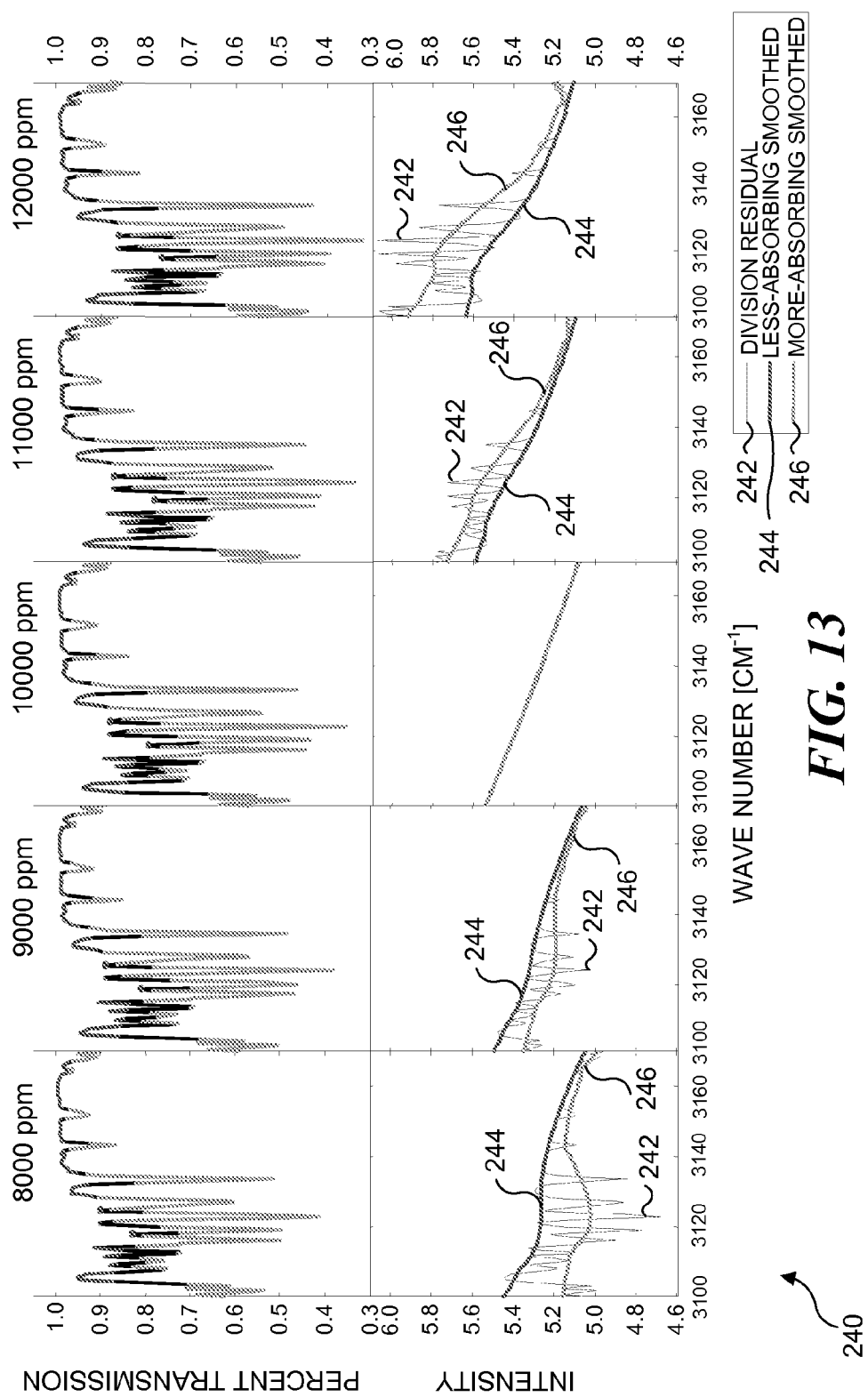
Figure 14:
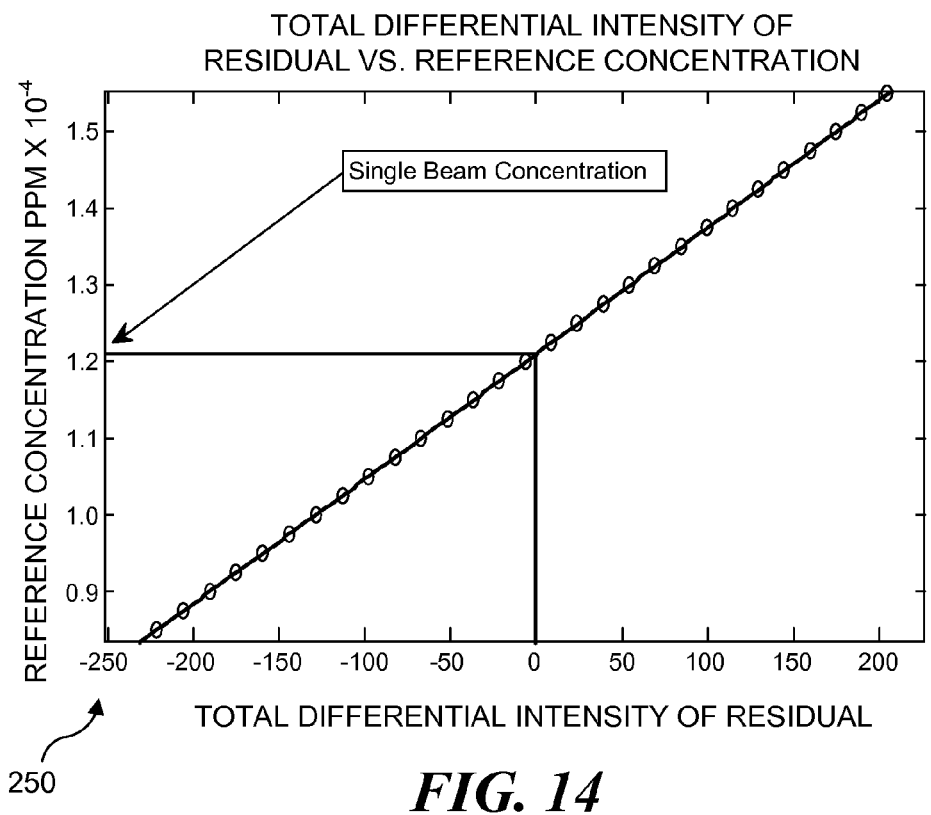
Figure 15:
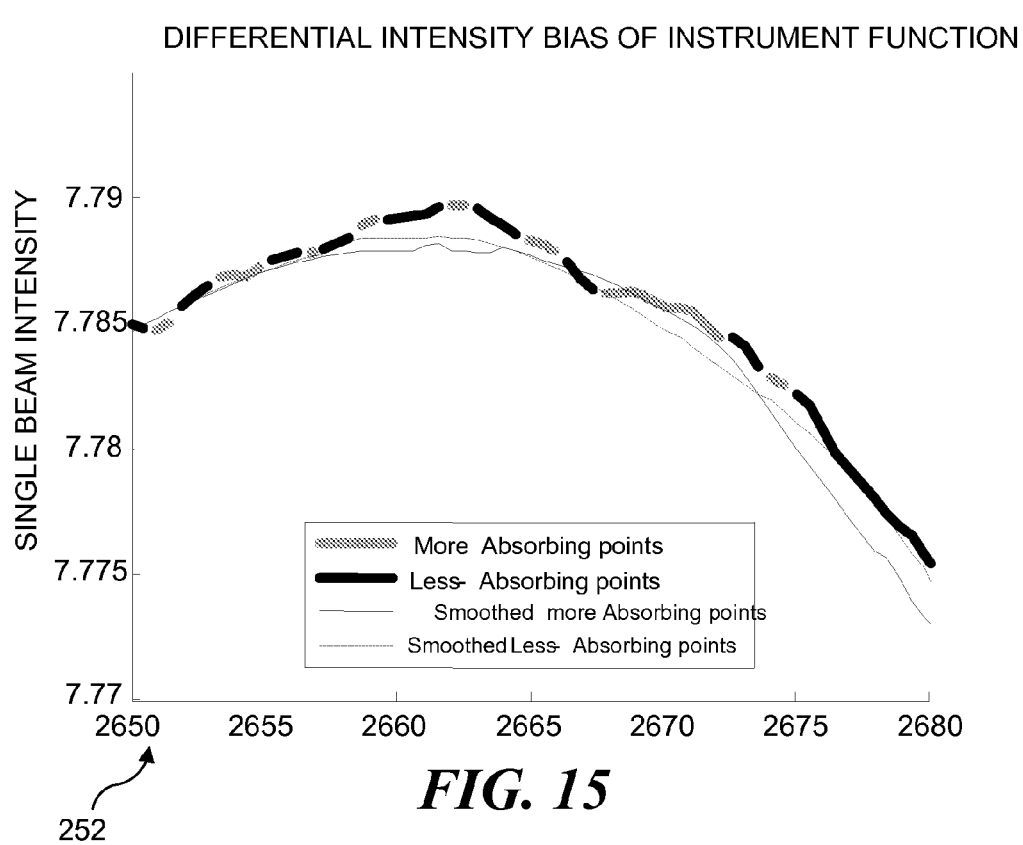
Figure 16:
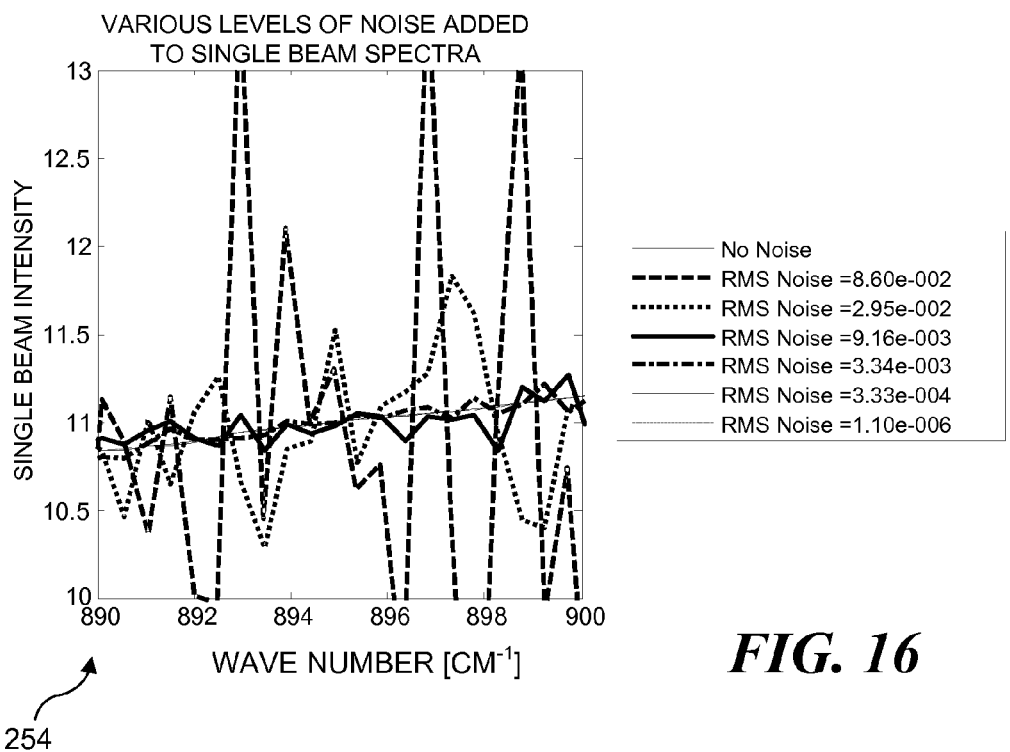
Figure 17:
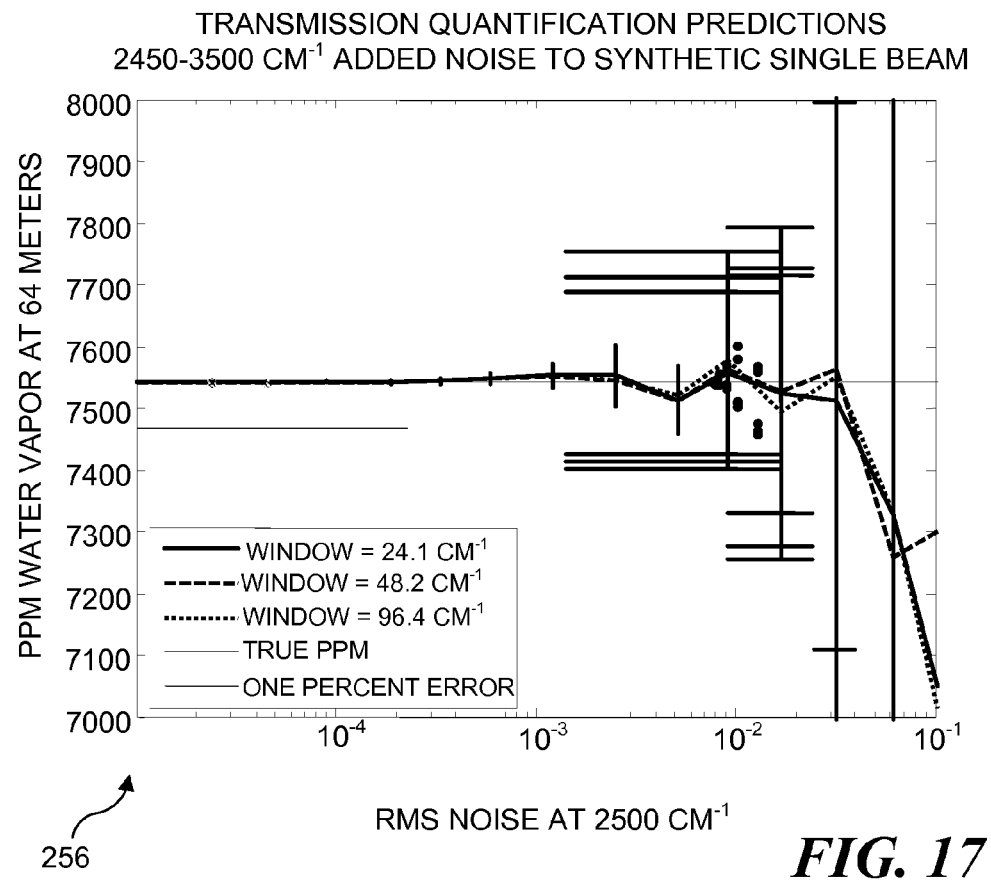
Figure 18:
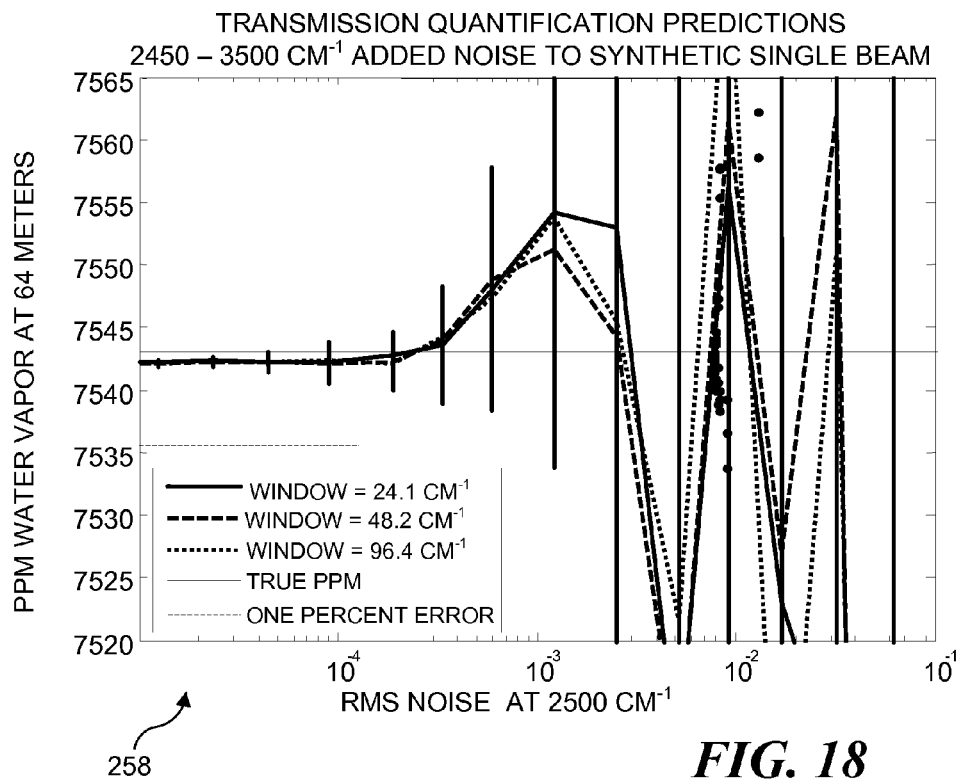
Figure 19:
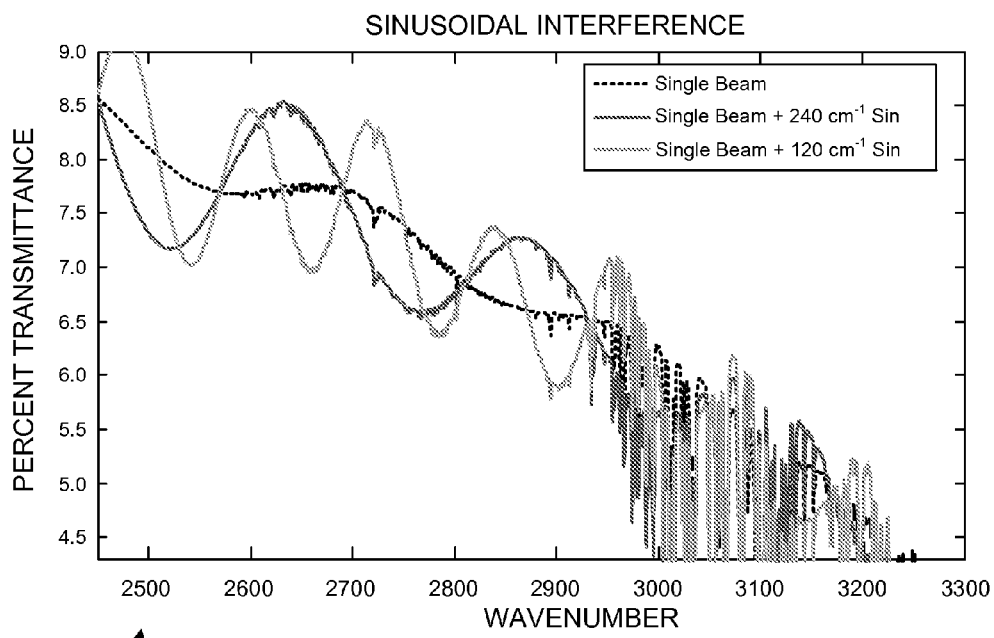
Figure 20:
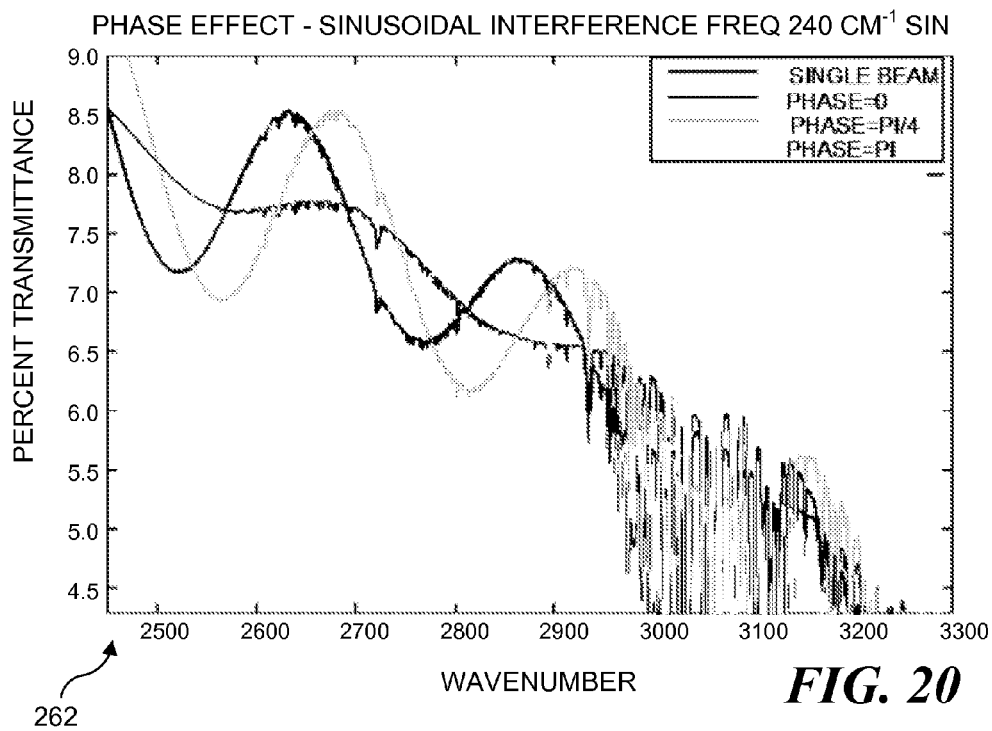
Figure 21:
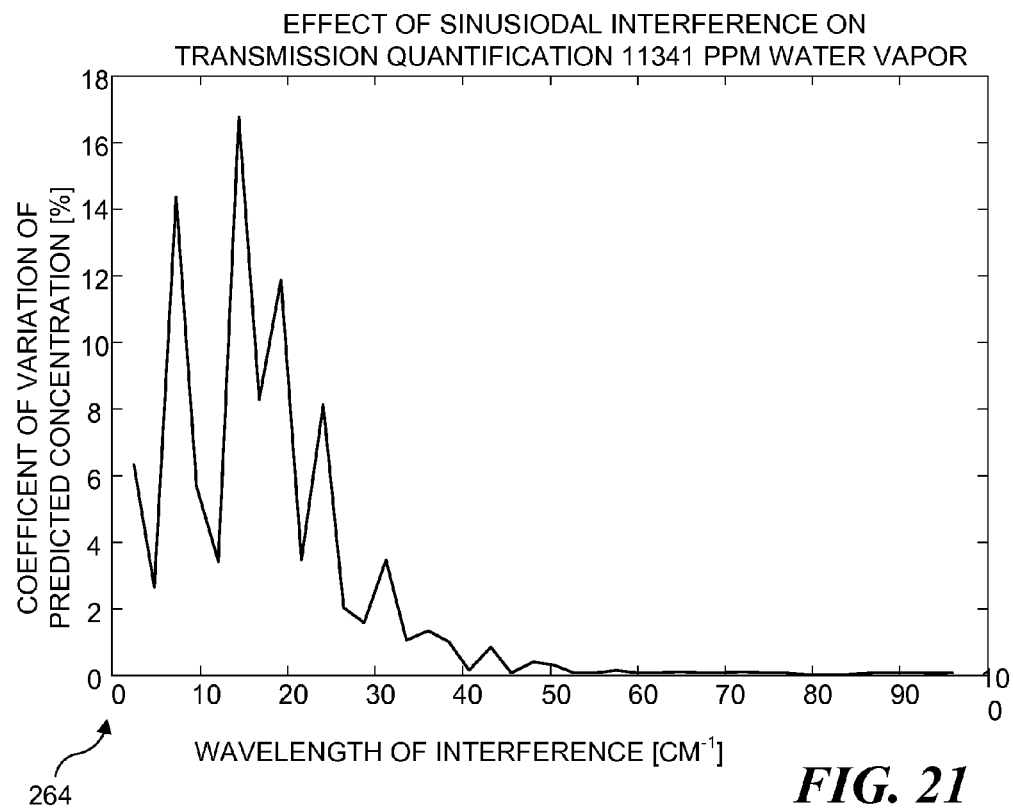
Figure 22:
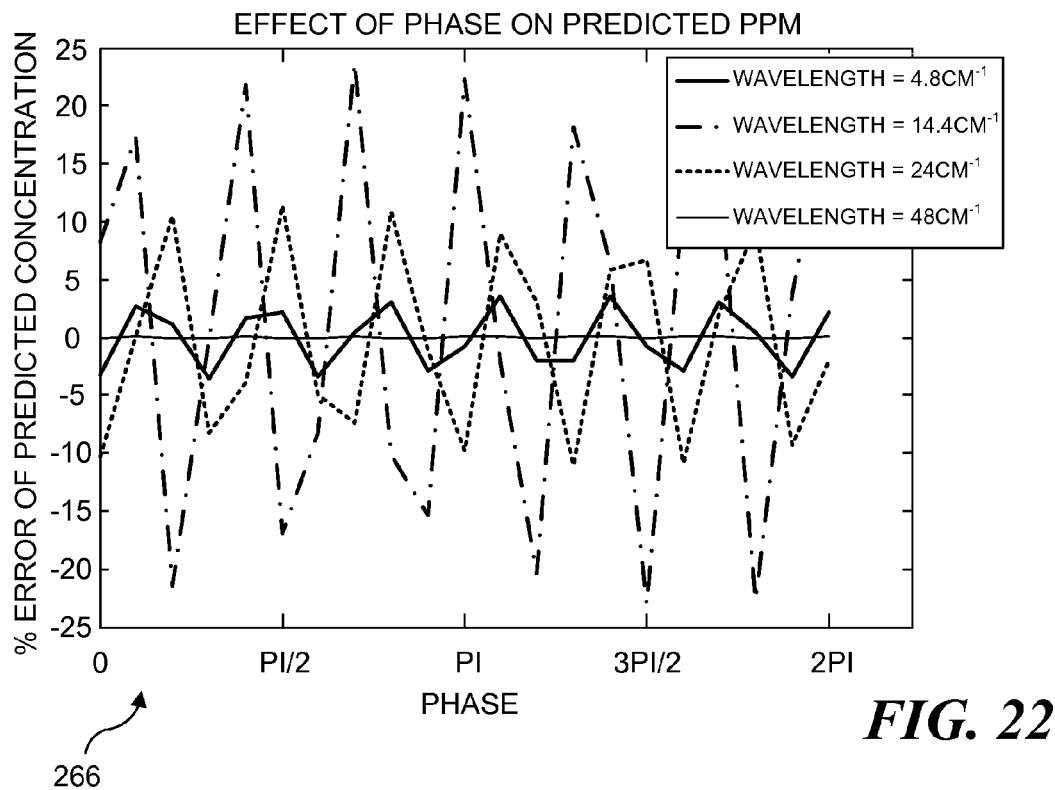
Figure 23:
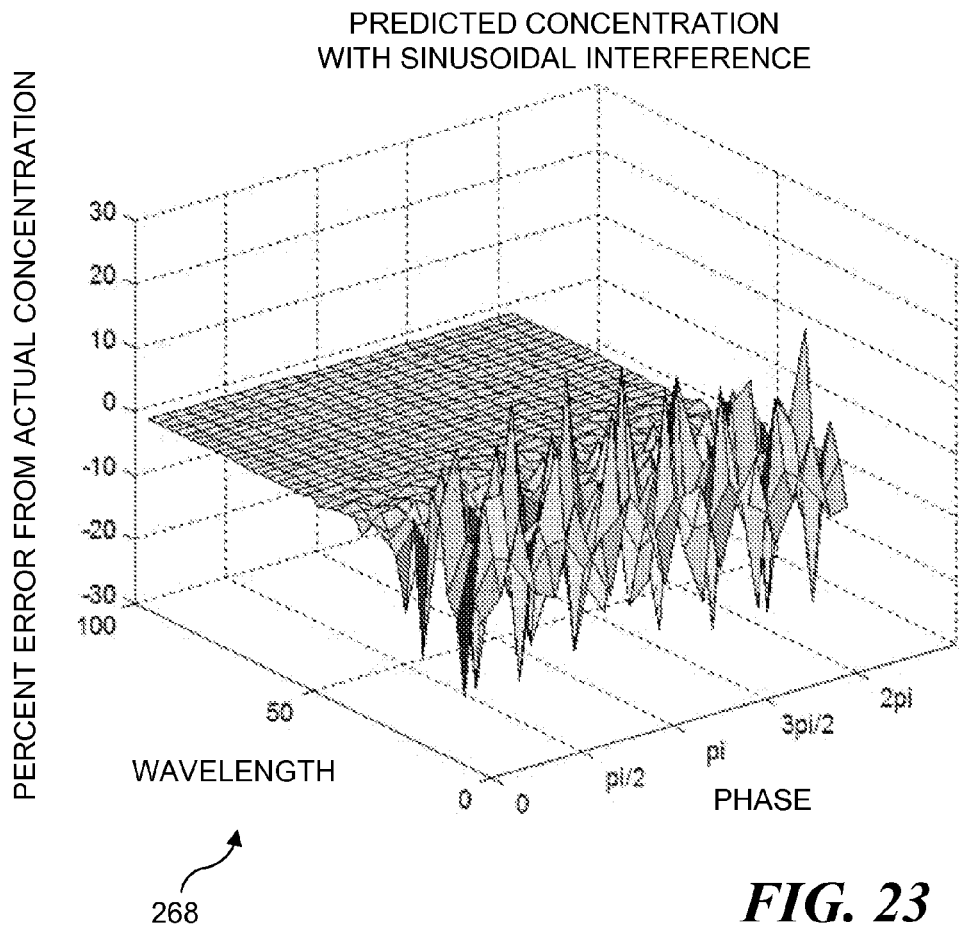
Figure 24:
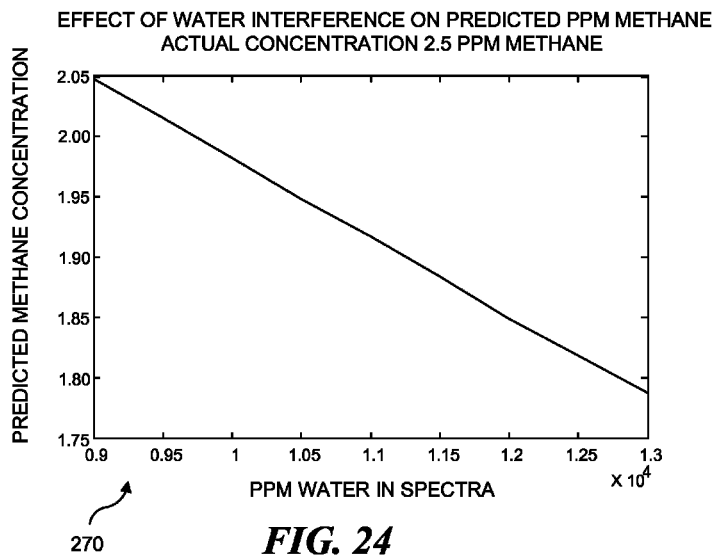
Figure 25:
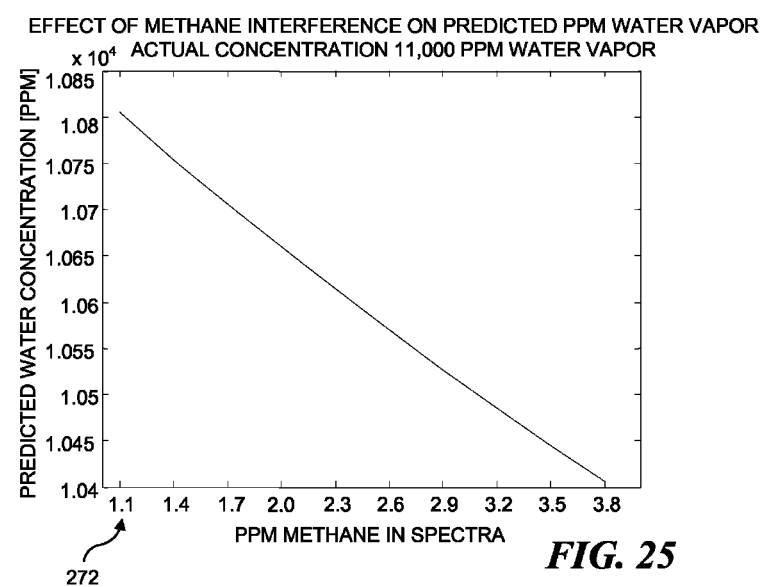
Figure 26:
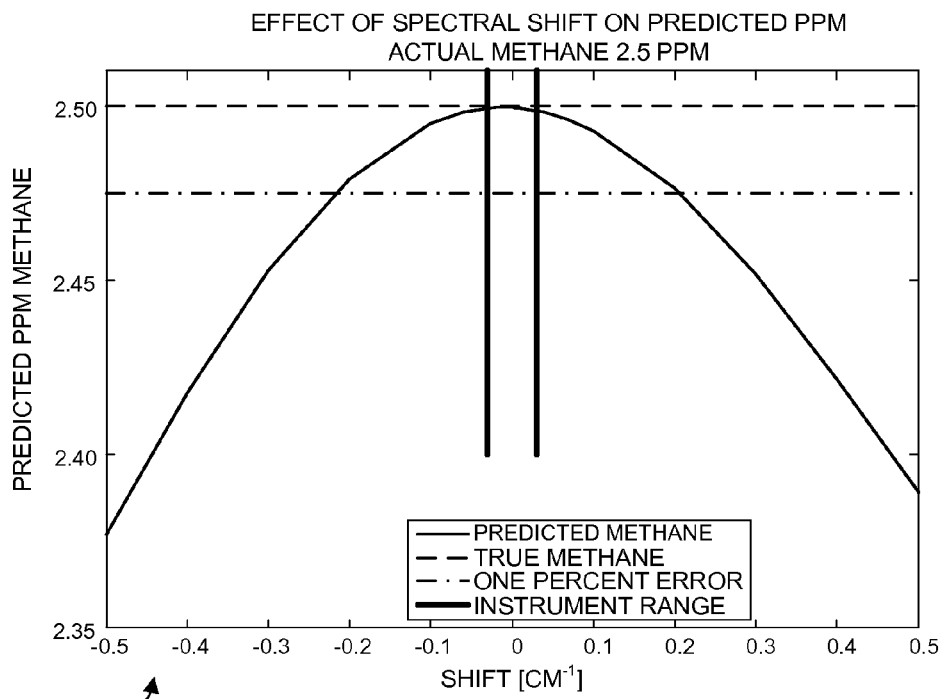
Figure 27:
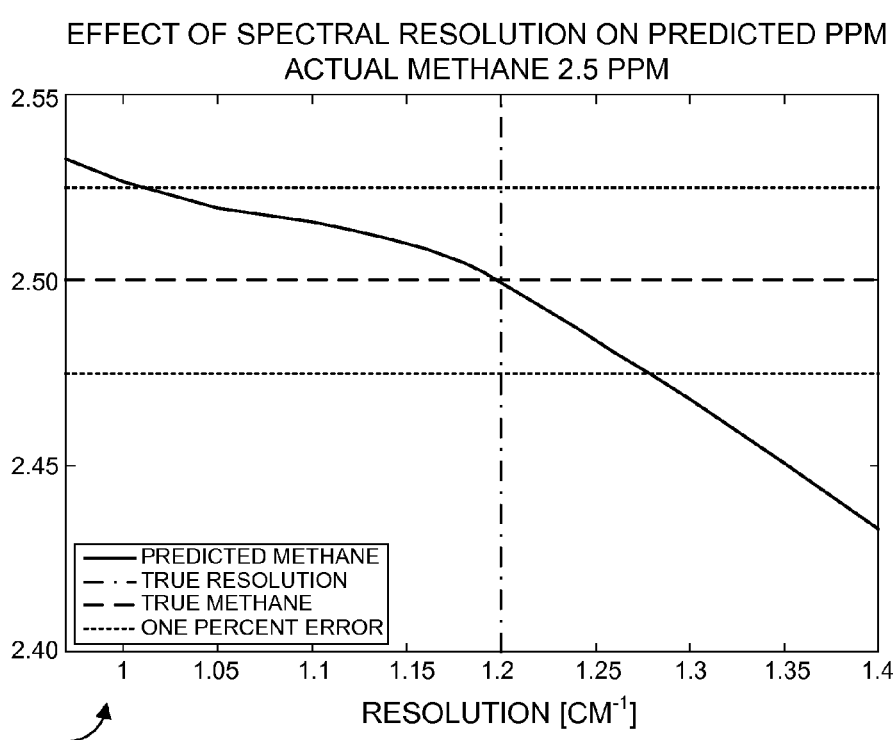
Figure 28:
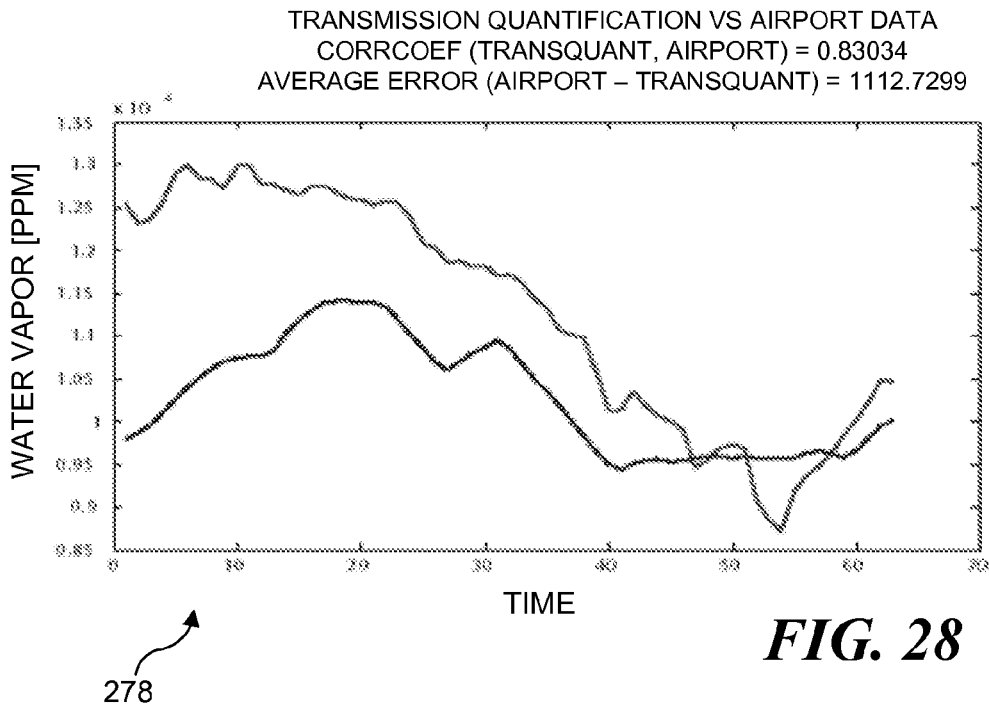
Figure 29:
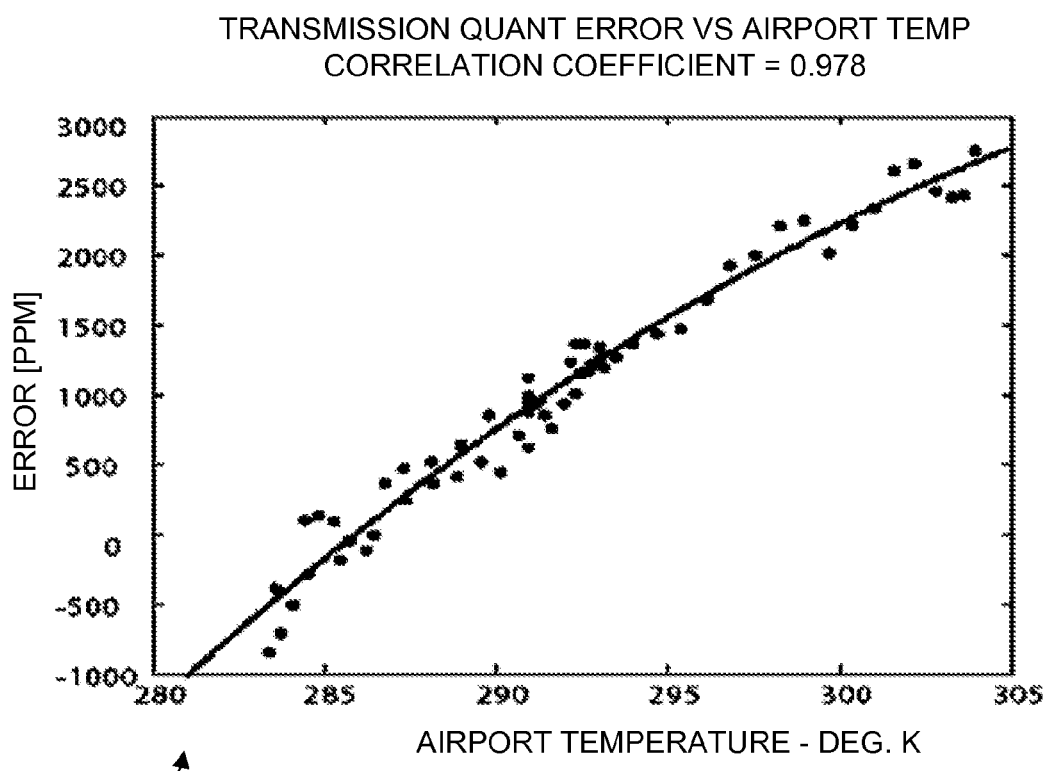
Figure 30:
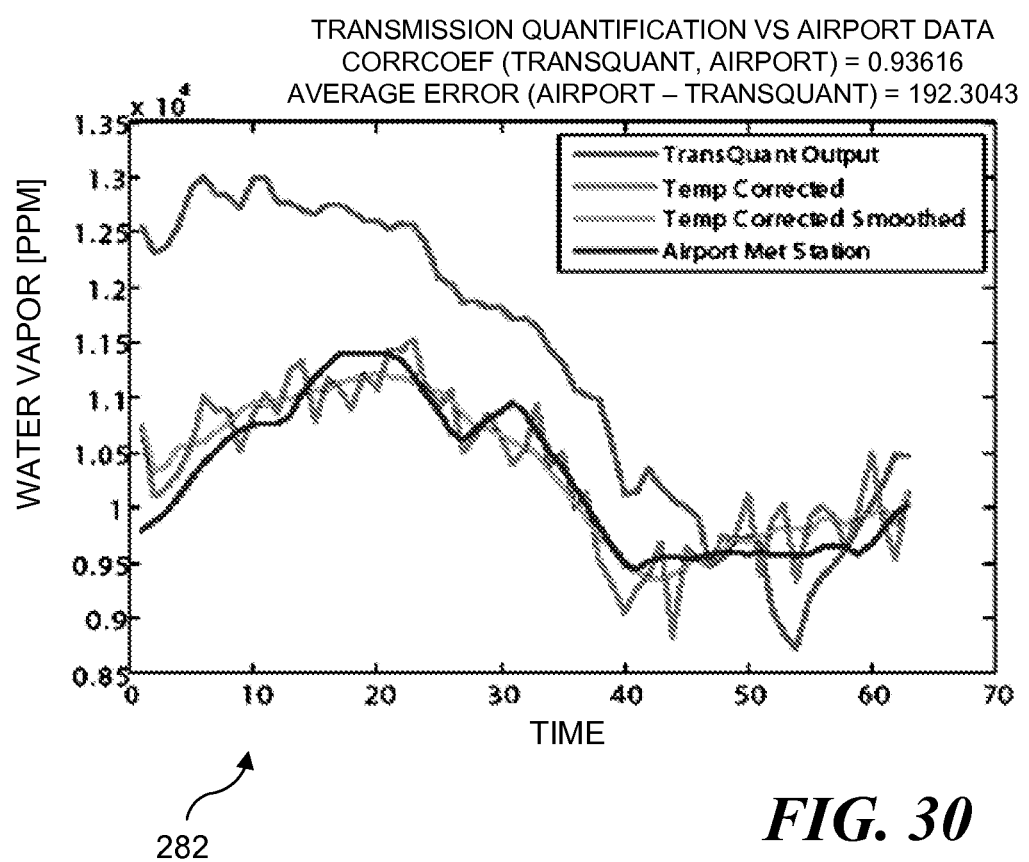
Figure 31:
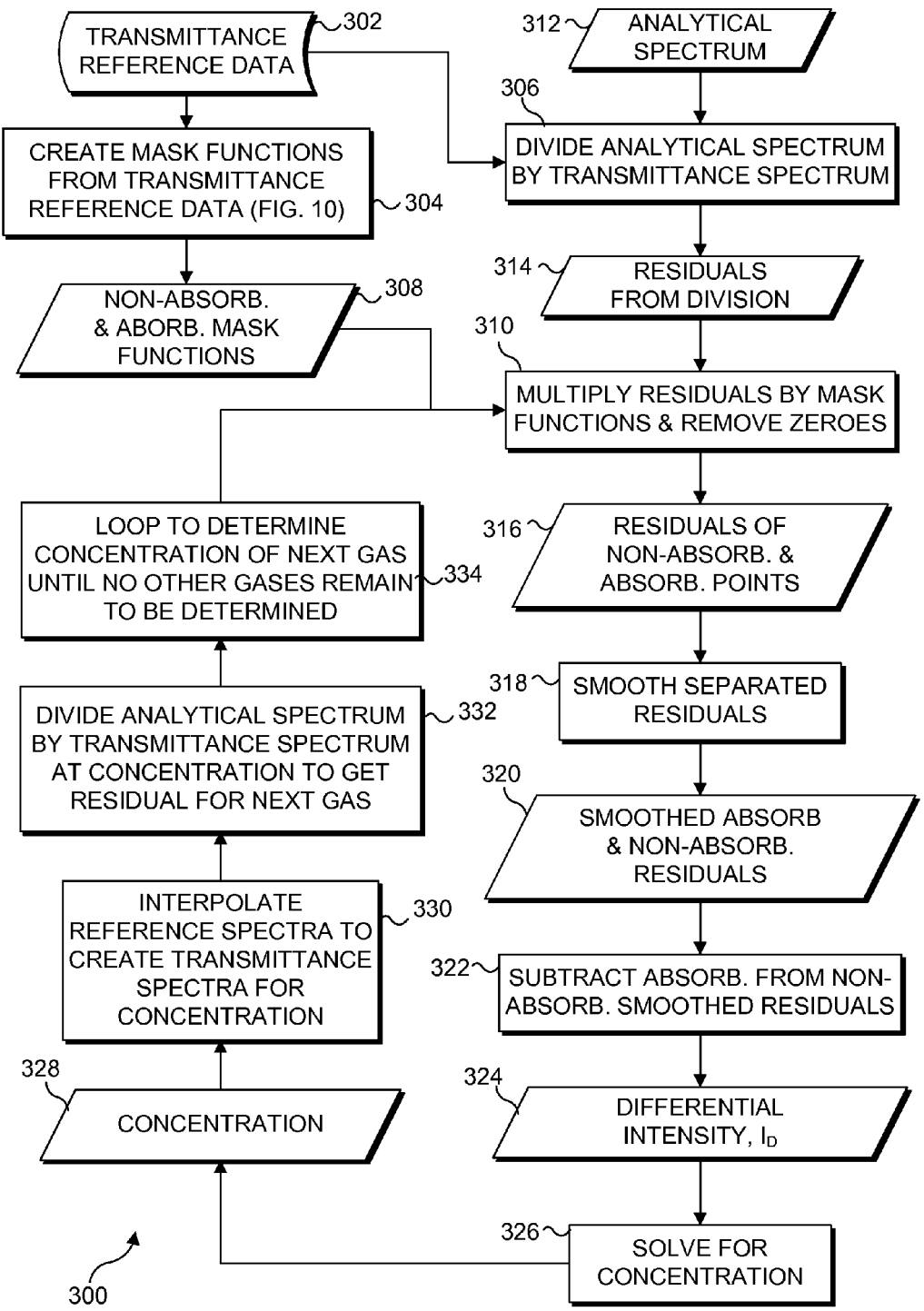
Figure 32:
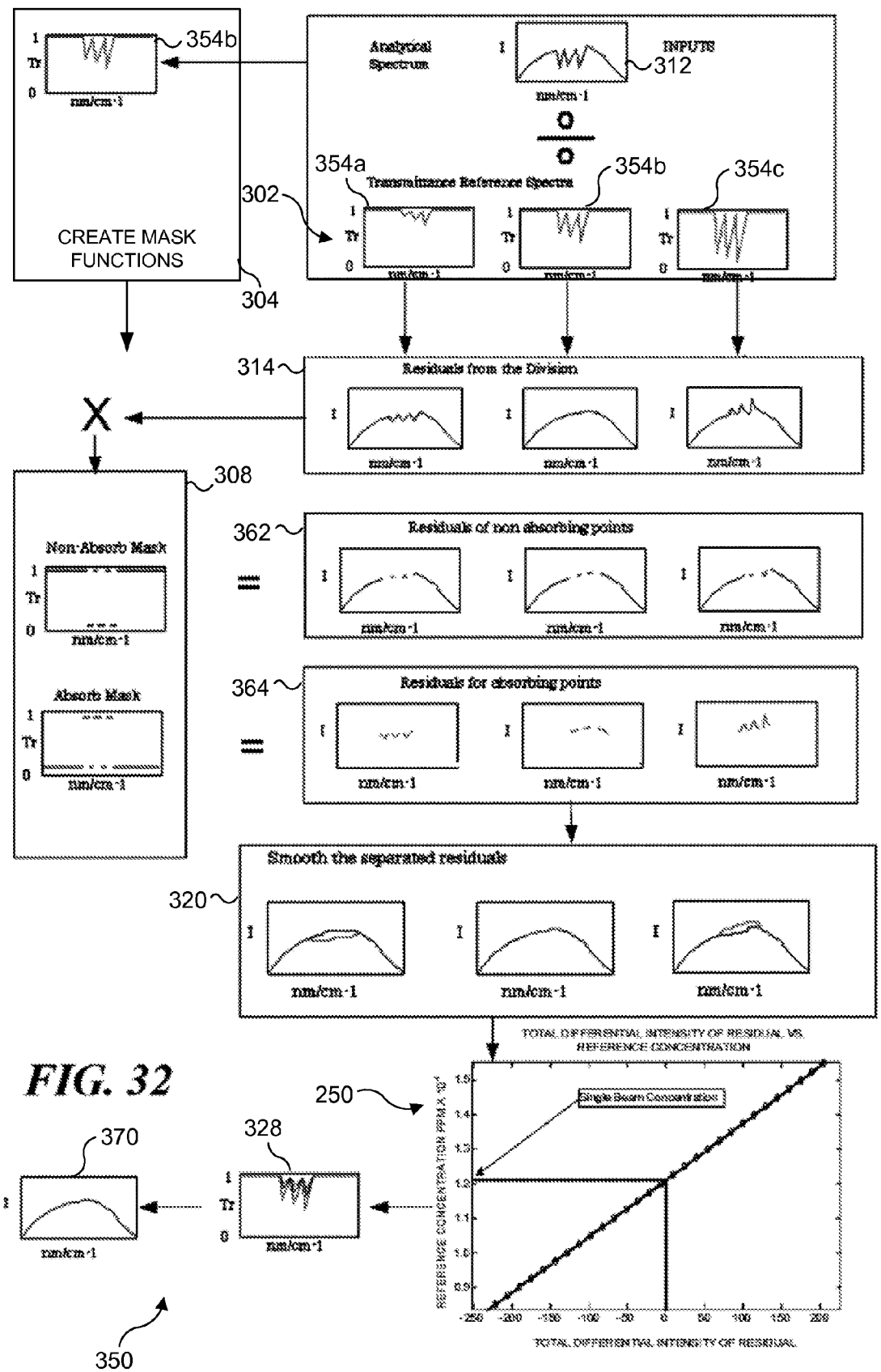
Figure 33:
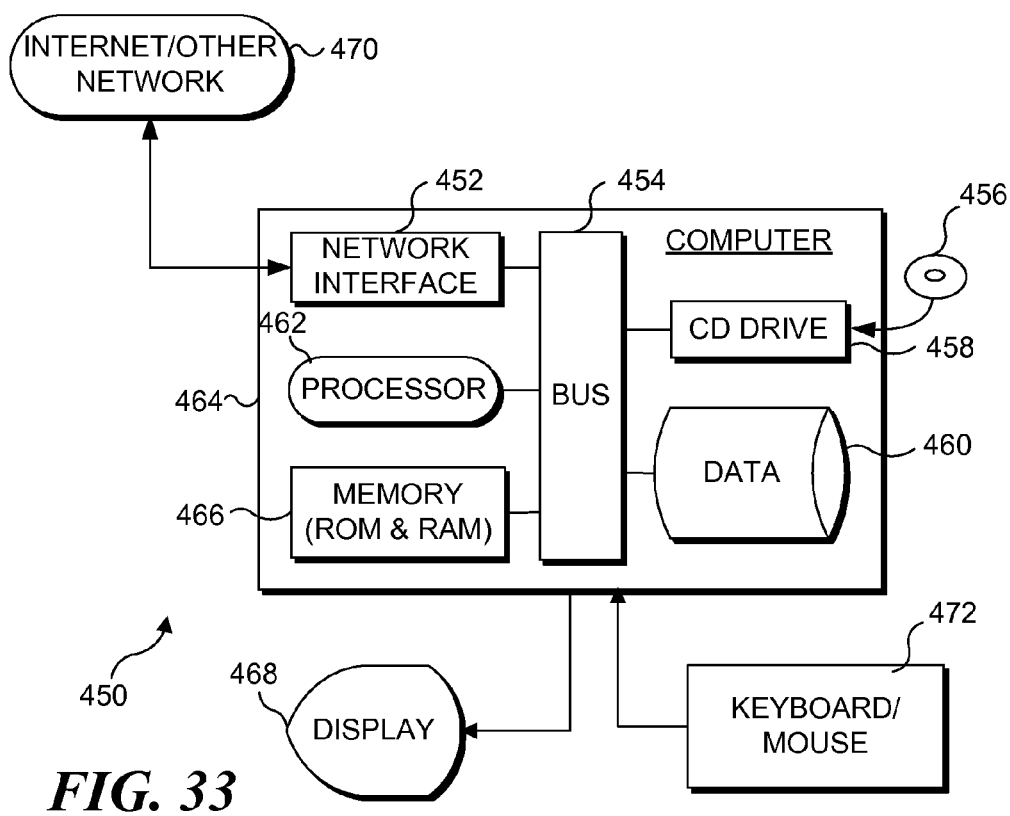

FIG. 10 is an exemplary graph illustrating how a floating median divides a synthetic water vapor spectrum into "more absorbing" and "less-absorbing" points; in this approach, two masking functions are created from this separation of points, and the functions oppose each other, so that a value of one or "no value" at each point indicates the designation of that point as a "more" or "less" absorbing point;

FIGS. 11A and 11B are graphs that respectively illustrate inputs for a transmission quantification model for a single beam spectrum (FIG. 11A) and a transmission reference spectrum (FIG. 11B);

FIGS. 12A, 12B, and 12C are exemplary graphs that respectively show division of an input single beam by a reference transmission spectrum, the results of separation of the resulting residual into two arrays by multiplying it by two mask functions, and the results of smoothing the two arrays so an area can be calculated between them;

FIG. 13 is a multi-panel graph illustrating that after division of a single beam spectrum by a series of synthetic water reference spectra, the less absorbing pixels are smoothed independently of the more absorbing pixels, wherein the center frame in the bottom series represents a correct concentration and the other bottom frames indicate the subsequent lining up of the more absorbing and less absorbing points in the residual;

FIG. 14 is an exemplary graph of total differential intensity ($I_D$) in a residual spectrum vs. reference water vapor concentration, wherein a point along the X-axis where the value of $I_D$ approaches zero represents the concentration of water vapor in the single beam spectrum;

FIG. 15 is an exemplary graph of differential intensity bias of an instrument function, wherein more absorbing and less absorbing arrays smoothed on an $I_0$ estimation illustrate how a bias in total differential intensity is created by the relationship of the two arrays to the underlying shape of the FTIR spectrum (the difference between the smoothed lines is small but not zero);

FIG. 16 is an exemplary graph illustrating different noise levels that are added to single beam spectra, to emphasize that the present transmission novel quantification algorithm can quantify water vapor concentration to within 1%, even with the highest amount of noise shown in this exemplary graph;

FIG. 17 is an exemplary graph showing the predictive ability of the present transmission quantification algorithm at three window widths, with increasing noise added, to illustrate that the predicted concentration of water vapor is within 1% of the actual concentration at noise levels of $10^{-2}$, which is 100 times the noise level of a typical OP-FTIR system;

FIG. 18 is a more detailed view of a portion of FIG. 17, wherein the predicted concentration of water vapor is within 1 ppm of the actual concentration at noise levels of $10^{-4}$, which is the noise level of a typical OP-FTIR system;

FIG. 19 is an exemplary graph of a synthetic single beam spectrum both with and without added sinusoidal interference, it being noted that similar effects can occur in the field when particulates enter the beam-path or settle on the retroreflector;

FIG. 20 is an exemplary graph showing a phase effect on the single beam spectra, with different sinusoidal interference functions added, wherein each spectrum is for a wavelength of 240 $cm^{-1}$, with different phase offsets;

FIG. 21 is an exemplary graph showing the wavelength of sinusoidal interference vs. predicted concentration, to emphasize that the novel transmission quantification method described here is very robust to sinusoidal interference with wavelengths longer than 40 $cm^{-1}$;

FIG. 22 is an exemplary graph illustrating the effect of the phase offset of interfering sinusoidal function on predicted concentration, wherein longer wavelengths have little effect on the transmission quantification method and shorter wavelengths that can cause errors in the predicted concentration are highly dependent on phase;

FIG. 23 is an exemplary three-dimensional graph illustrating the effect of sinusoidal interference of varying frequency and phase on the ability of the transmission quantification method to predict the concentration of water vapor in synthetic spectra;

FIG. 24 is an exemplary graph showing the negative bias of water vapor on the present novel transmission quantification model's predicted concentration of methane from a single beam spectrum, wherein the ranges shown are the approximate ranges of methane and water vapor from the experimental data, and the addition of water results in a decreasing prediction of methane by the transmission quantification algorithm;

FIG. 25 is a graph showing the negative bias of methane on the transmission quantification model's predicted concentration of water vapor from a single beam spectrum, wherein the ranges shown are the approximate ranges of methane and water vapor from the experimental data, and the addition of methane results in a decreasing prediction of water vapor by the present novel transmission quantification algorithm;

FIG. 26 is an exemplary graph showing that spectral shift errors between the input spectra and the reference array results in small errors in predicted concentration from the present novel transmission quantification method;

FIG. 27 is an exemplary graph showing the effect of a difference in resolution between the references input into the present novel transmission quantification model and the input single beam spectra, wherein over the entire range of expected resolutions, the error in predicted concentrations is marginal, and the 1% error line encompasses most of the range;

FIG. 28 is an exemplary graph showing transmission quantification results compared to the water vapor content, as recorded at the Yakima, Wash. Airport;

FIG. 29 is an exemplary graph illustrating how errors in prediction for the data of FIG. 28 are almost entirely explained by the effect of temperature;

FIG. 30 is an exemplary graph showing how temperature correction of the data for FIG. 28, as determined along the propagation path and smoothing, brings transmission quantification close to 1% accuracy;

FIG. 31 is a graph showing exemplary steps that are carried out in the present novel approach to determine the concentration of gases using OP-FTIR (and other related measurement techniques);

FIG. 32 is a schematic diagram illustrating an example that applies the logical steps of FIG. 31; and FIG. 33 is a functional schematic block diagram of a generally conventional computing device, such as personal computer, which can be employed for carrying out calculations in connection with the novel approach for determining gas concentrations along a light propagation path.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Two Desired Goals of Novel Approach

Transmission Quantification

One goal of an exemplary embodiment of the present approach is to provide a method of quantification that involves only a single beam analytical spectrum and a synthetically created transmittance reference spectra. The temperature of the beam can be determined from the model as discussed in detail below, and the other important parameters can also be determined a-priori. These transmittance spectra can be created with the HI-TRAN data base and used on a single beam output of an OP-FTIR.

An important difference between the present novel method and traditional OP-FTIR quantification is that in the present approach, the references are transmittance spectra and not absorbance spectra. The Beer-Lambert law is not used in the transmission quantification method of determining gas concentration. Furthermore, the present method does not compare absorbance spectra of known reference gases at known concentrations to calculated absorbance spectra from the field. Instead, transmission quantification compares transmittance reference spectra to the single beam intensity output from the field. The transmission reference spectra can be created from a computer database (synthetic spectra) or obtained from carefully controlled laboratory experiments. This novel way of quantifying gases is not affected by many of the problems that can arise in traditional approaches due to a mismatched background or reference. The method has been shown to be very robust to noise and broadband interferences.

Temperature Determination

In the field, temperature sensors can be used to detect the ambient temperature at one or more points along the path that light will propagate during the detection of components in the light path while implementing OP-FTIR measurements. However, there can be significant variations in temperature along a relatively long light path that will not be accurately noted by just measuring the temperature at just a few selected points. Thus, another goal was determine the effective temperature along the entire light path rather than just at a specific measurement point. Accordingly, a model was created for water vapor temperature determination based on the relative strengths of water transmission lines in the raw single beam analytical spectrum, which eliminates the need for one or more very accurate thermometers in the sample space along the light path. The temperature is then derived from the same spectral features that it is used to model. Therefore, this approach better represents the true water vapor temperature for the beam path at that time than even several accurate measuring devices, especially, if rapid single scan data are required in a dynamic environment. The optically derived temperature can then be used to create synthetic reference spectra for quantification of each analytical spectrum. This model is discussed below.

Conventional OP-FTIR Techniques

Figure 4:
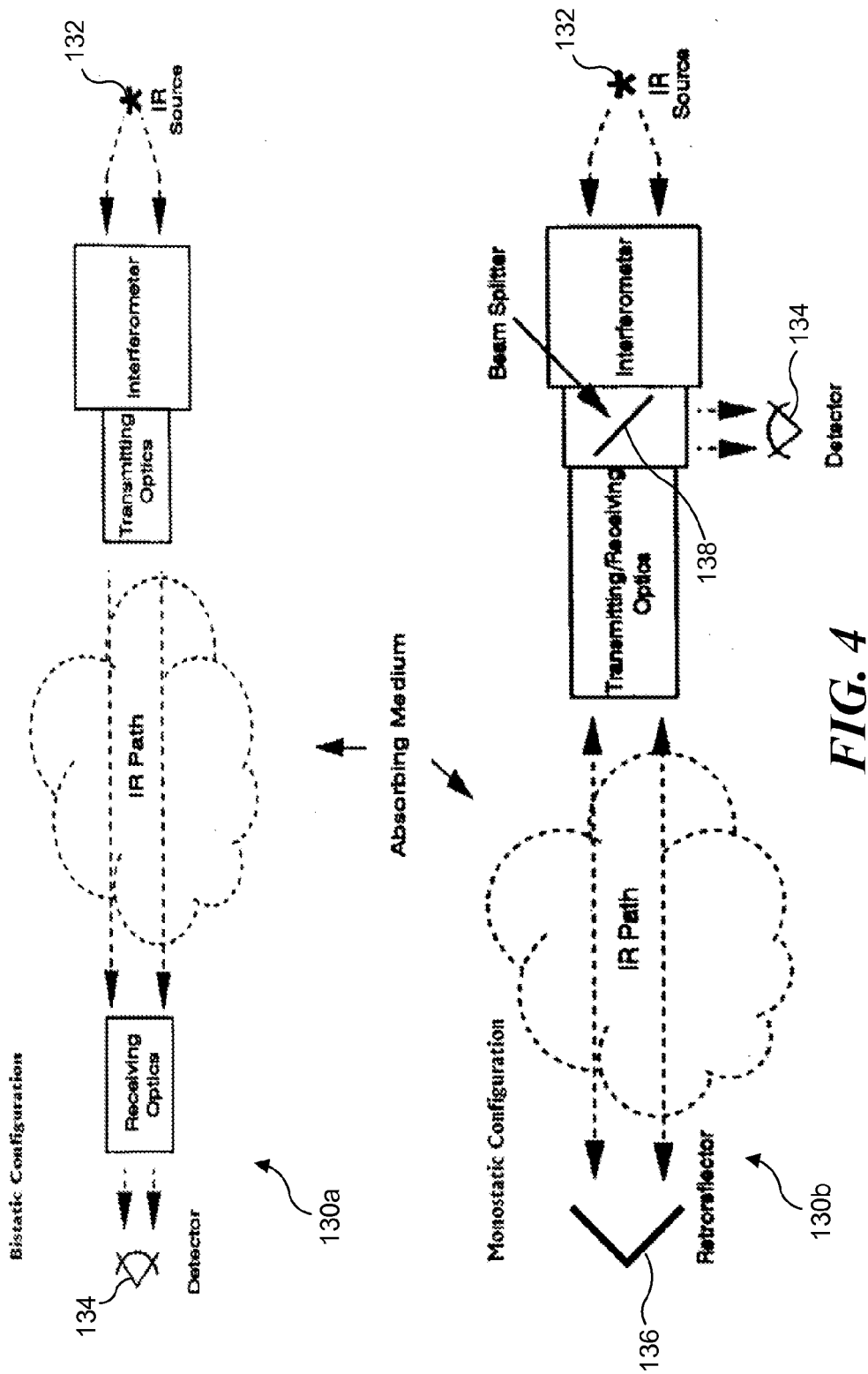
FIG. 4 (Prior Art) illustrates schematic diagrams of a bistatic (top) and a monostatic (bottom) OP-FTIR configuration.

Several detailed descriptions of conventional OP-FTIR methods are available in the literature and are only briefly described herein. There are two primary geometrical configurations available for transmitting an infrared beam along an open path. One is a bistatic system 130a; the other a monostatic system 130b, as shown schematically in FIG. 4 (Prior Art). In the monostatic system, both an infrared source 132 and a detector 134 are disposed at the same end of the path, whereas for the bistatic system, the IR source is disposed at one end of the path and the detector at the other. The system used in the novel approach described below is monostatic. Monostatic systems have several advantages, including: (1) they are easy to align with a retro-reflector 136; (2) they have a compact design with only one power supply (not shown); and, (3) they employ an increased path length (by a factor of two), since the beam travels both to and from retro-reflector 136. A disadvantage of the monostatic system is the need for an additional beam splitter 138 separating the outgoing and incoming beams, which reduces the signal-to-noise ratio by 50%.

Figure 5:
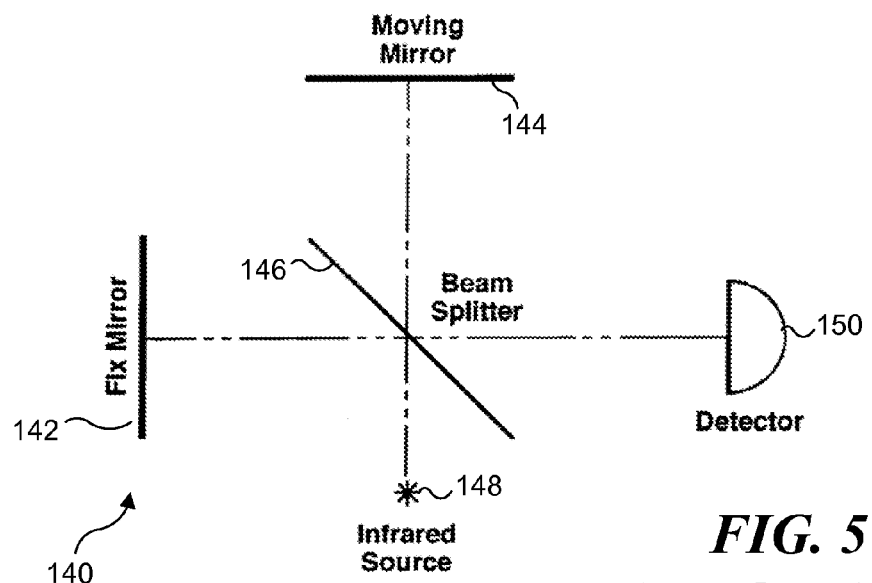
FIG. 5 (Prior Art) is an exemplary schematic diagram of a simple Michelson Interferometer.

A Michelson interferometer 140 (see FIG. 5—Prior Art) is the heart of the FTIR spectrometer. Its design includes two orthogonal mirrors 142 and 144 (where mirror 144 moves), and a beam splitter 146 that directs approximately half of the infrared energy from a source 148 to each mirror. As mirror 144 moves, the two beams have varying amounts of constructive and destructive interference at different wavelengths, detected by a detector 150. Thus, all wavelength intensities are modulated at a frequency that is dependent on the mirror velocity and the wavelength of the light.

The data recorded are the infrared intensity at the detector as a function of the moving mirror position, which comprises an interferogram. These data typically comprise relatively large files, with several times as many points as the subsequent spectra. The data are archived as interferograms, since some information is lost through the processing. A fast Fourier transform (FFT) is performed on this interferogram and results in a single beam spectrum for the intensity of light at the detector as a function of inverse wave-number ($cm^{-1}$). The single beam spectrum is then used for further processing.

Traditional FTIR Data Analysis

Figure 6:
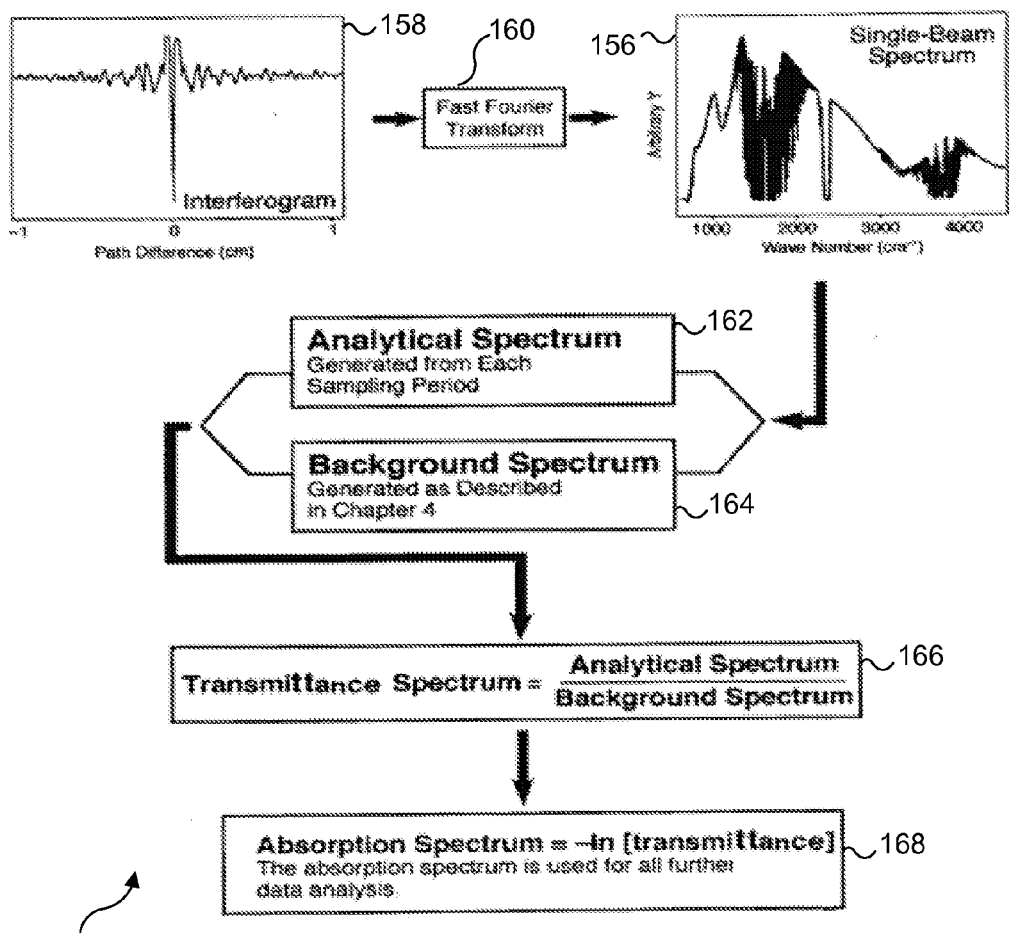
FIG. 6 (Prior Art) is a simplified flowchart illustrating exemplary steps for carrying out a Fourier Transform Infrared (FTIR) data analysis.

A flowchart 154 illustrating the steps employed for conventional FTIR data analysis is shown in FIG. 6 (Prior Art). A single beam spectrum 156 converted from an interferogram 158 is generated and recorded for each sampling period using a fast Fourier transform 160. This spectrum is also called an analytical or sample spectrum 162 and indicates the absorbance from the chemicals of interest and ambient concentrations of gases, in addition to the emission spectrum of the infrared source.

A background spectrum 164 also is required to characterize the source emission, the generation of which has been discussed in many studies, as will be well-known to those of ordinary skill in the art. Transmittance spectra 166, often called double beam spectra, are obtained by dividing the analytical spectra by the background spectra. Absorbance spectra 168 are the negative logarithms of the transmittance spectra and are used to quantify the gases using the Beer-Lambert law. Conventional data analysis of OP-FTIR sampling is based on the Beer-Lambert law, which states that the infrared energy traversing an absorbing medium diminishes exponentially with concentration and path length. Mathematically, this relationship is written as:

$$I_A(\nu) = I_0(\nu) e^{-\alpha(\nu)CL} \quad (1)$$

where $I_0(\nu)$ is the intensity of the incident beam measured on the clean background spectrum, and $\alpha$ is the optical absorption coefficient of the absorbing material(s), such as target gases and $H_2O$. All terms are a function of $\nu$ which is wavenumber, usually in units of $cm^{-1}$. C is the concentration of material and L is the path length. The absorbance, A, due to a specific gas can then be written as:

$$A = -\ln(I_A/I_0) = \alpha(\nu)CL. \quad (2)$$

The absorbance spectrum is compared to a standard reference spectrum of the target gas at known concentrations in the appropriate wave-number region. The selection of reference spectra should be based on an examination of the standard and the type of analysis method chosen. Ideally, the gas should have a high absorption coefficient in the selected region, and the region should be free of any interfering species. The most common multi-component analysis method used in OP-FTIR monitoring is based on a classical least squares (CLS) fitting algorithm. The CLS performs a linear regression by using the unknown analytical absorbance spectrum and a set of standard absorbance spectra with known concentrations over one or more wave-number regions. From the slope of this regression, the integrated concentration in the entire path length of the double beam spectrum is calculated for one or more components. The units of this measurement are ppm-meters. A beam average concentration is thus obtained as:

$$C_{average} = C_{pic}/L \quad (3)$$

where $C_{average}$ is the path average concentration (ppm), $C_{pic}$ is the path integrated concentration (ppm·m), and L is the beam path length in meters. The fundamental point illustrated in Eq. (3) is that the path average concentration is a derived parameter, whereas the instrument response is always in terms of $C_{pic}$, which is path length dependent.

Factors that Influence OP-FTIR Spectra

Many factors can affect the final spectrum, some of which are known and can be controlled, while others are unknown and uncontrollable. Factors such as the nominal resolution (mirror displacement), and FFT parameters, such as zero fill, phase correction, and apodization, can be controlled or documented. The instrument mirrors, beam splitters, and the interferometer all have known optical transmission characteristics that should remain fairly constant over long periods for a single FTIR. The infrared energy source is usually a glow-bar or ceramic resistor element whose temperature can be adjusted by changing the current that heats it. This component will wear out over time, causing its emission spectrum to slowly change. Some beam splitters are made of salt or other materials that can be damaged by humidity and require desiccation or other measures to protect them. The infrared detector also has a limited life span, and it has other specific requirements. For example, the widely used Mercury-Cadmium-Telluride (MCT) semiconductor detector must be kept near 80° K to function properly. It is also possible to overload the detector or damage it when operated improperly. When the liquid nitrogen level is insufficient or the cryogenic cooler is not doing its job, the detector response also suffers, and stable cooling of the detector is necessary to achieve acceptable results.

OP-FTIR spectrometers differ from their bench-top versions in important ways. Being exposed to the outside atmosphere means that they can be subjected to changes in temperature as great as 100° F. Another important difference is that the retro-reflectors are not attached to the spectrometer with an accuracy and consistency that is anywhere near that of a typical optical bench. This fact makes the retro-reflector the optical component that is most likely to be changed under field conditions and the one that is most exposed to the elements. Dust or other film deposits may decrease the beam transmittance or even "color" the infrared beam (change the spectral energy distribution) if they are allowed to collect on the retro-reflector or any other optical surface of the system. Interferometry, due to its dependence on the relative position of micron and smaller scale waves, has always been dependent on extremely accurate physical equipment. The tiny inconsistencies of retro-position and thermal-expansion effects on the interferometer can change the apparent spectra considerably. It has been shown that the spectral resolution and shift can and do change at a given setup over a matter of minutes to hours. These changes do not much affect the spectra of broadband absorbers, such as octane, but for the most important atmospheric infrared absorbers with narrow line features, i.e., water vapor and carbon dioxide, the effects can be very important.

As stated above, another set of factors that will affect the final spectrum is not known beforehand and therefore, can be harder to manage. These factors can be considered part of the background problem or an interference problem. Water and $CO_2$ contribute the primary infrared absorbance features in the troposphere. Water is particularly troublesome for OP-FTIR spectroscopy, because it produces numerous lines across the mid-infrared, and because of its tendency to change with time. The water vapor spectrum also has a nonlinear relationship with temperature and concentration. Atmospheric aerosols/particulates can also change concentration and typically, are unknown. In the 2-10 micrometer size range, these particles will scatter infrared energy from the beam path according to Mie theory, leading to changes in the light extinction spectrum. This effect depends on size distribution, shape, abundance, and the chemical properties of the scattering aerosols. The unknown factor that is of greatest interest is the concentration of one or more trace target gases that have an infrared absorption feature. In absolute terms, the analytical single beam spectrum obtained with the OP-FTIR is affected orders of magnitude more by parameters other than the absorption of a target gas, which can adversely impact determination of the desired concentration results. Therefore, relatively small differences in any of the other factors can greatly affect the quantification of the target compound. All of these factors must be dealt with in the process of background selection and/or interference/target gas reference selection.

Synthetic Background Strategies
Polynomial Fit Background

Commercially available software, which is included with most OP-FTIR instruments and is readily available, generally includes a polynomial fit background routine. This routine involves the user locating points where the baseline is at zero across the bandwidth of concern, and then employs computer fitting for a polynomial of user determined degree, to use as a background. This prior art approach can be time consuming and in some cases, it is difficult to find enough points on the spectrum where the absorbance is truly zero. The continuum spectrum of water can be non zero for large portions of the infrared range. This method is able to correct for scattering and broadband absorption of particulate matter, since those features can cause errors in the quantification of gases. After a polynomial fit to the baseline, the gases can be quantified by Beer's law.

An Iterative Approach

Iterative techniques have also been used to create synthetic backgrounds. An initial $I_0$ is used as the background for the first spectrum in a series. Then, as the concentrations are determined for a sample, the background for the next sample is created. This step is carried out by subtracting the gases found in the first sample from the raw spectrum for the first sample. The iterative approach is a variation of the pre/post event method mentioned above. The synthetic version of this method is when the low points for different gases are on different individual spectra. These two spectra are combined to form a single background with the lowest amount of both gases.

HITRAN Based

HITRAN is a compilation or database of spectroscopic parameters, which a variety of computer codes use to predict and simulate the transmission and emission of radiation in the atmosphere. This database has been used in the prior art as a basis for OP-FTIR background components and reference spectra creation by several groups. Spectrsoft Inc.'s Nonlin™ program is one such example. These programs create synthetic spectra for water, $CO_2$, and other atmospheric gases. It is important to note that the gas absorption is only a part of the background modeling. The Nonlin™ code also uses elements of the polynomial fit method to determine instrumental features of the background.

Purpose and Context of Synthetic Spectra

The generation of accurate synthetic spectra is critical to achieving two central objectives in connection with the present approach. These are: (1) the determination of the temperature of the gases in the sample space of an OP-FTIR spectrometer from a single beam spectra; and, (2) the quantification of gases from an OP-FTIR single beam spectra without a background.

These objectives also both operate upon the single beam spectra that are created by the OP-FTIR system. It is important to note that the single beam spectrum does not represent the raw data from the OP-FTIR. Instead, the raw data from an OP-FTIR comprises the interferogram, which is a record of the intensity or voltage at the detector throughout the path of the Michelson interferometer's moving mirror. Mirror path difference is typically plotted on the X-axis, and intensity is typically plotted on the Y-axis.

The point in the interferogram having the maximum magnitude is referred to as the centerburst and corresponds to the point when destructive interference is at the minimum and constructive interference is at the maximum, because the moving mirror and the fixed mirror are equidistant from the beam splitter. Since these two paths are equidistant, the path difference, or retardation, is zero. The Bomem interferometer in the Environmental Technologies (ETG) AirSentry™ FTIR has a wishbone configuration that creates two points during a mirror scan, where the retardation is zero. Thus, there are two centerbursts.

Figure 7:
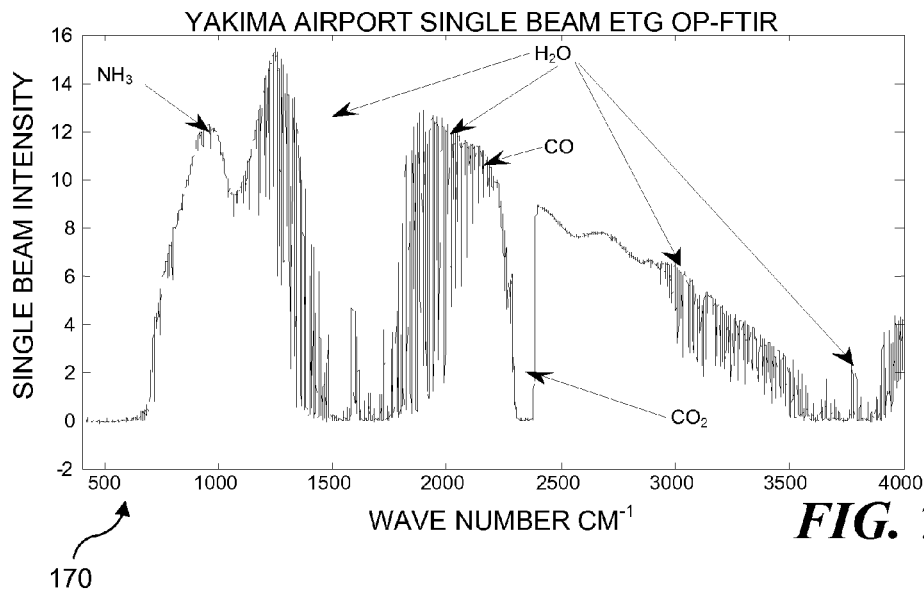
FIG. 7 (Prior Art) is a schematic diagram illustrating a system for determining an upwind background spectrum.

A Fast Fourier Transform (FFT) is applied to the interferogram to transform the data into the frequency domain. Apodization functions are chosen by the user for the purpose of reducing side lobes and other artifacts. Triangle apodization is used in the present exemplary approach, due to the availability of reference spectra and the limits of the software that drives the ETG Airsentry™ spectrometer. After the FFT is performed, the data are referred to as a "single beam spectra," in which frequency in inverse centimeters ($cm^{-1}$) is plotted against intensity at the detector. The term "single beam spectrum" is traditional nomenclature, contrasted with a "double beam" or transmittance spectrum. These terms come from the fact that to derive the transmittance of a sample, a second spectrum, $I_0$ is needed. As can be seen in an exemplary graph 170 that is shown in FIG. 7, water vapor absorption is the dominant feature in the fine structure of the data at this point.

Modeling the Gases

At this point, it may be helpful to provide a full explanation of how synthetic spectra are created and to note the parameters that are required. The starting point for most of these models is the U.S. Air Force HITRAN spectral database. The HITRAN database, which contains 32 gases, including gases with different isotope compositions that are commonly found in the atmosphere. Wavelengths from about 0.44 um to microwave are included. Available compounds include the important interfering species of $H_2O$ and $CO_2$; two of the gas tracers that are used in research, $N_2O$ and $SF_6$; as well as possible target gases in the atmosphere, such as CO, $SO_2$, $NO_2$, NO, $CH_4$ and $NH_3$. The HITRAN database has all the information needed to create synthetic spectra, including: the location of lines, the probability of transition, air-broadened and self-broadened half widths, and quantum indices describing the transition from lower to upper states. With these data, an ideal infrared transmittance spectrum is created. The ideal spectrum is then convolved with a model of the instrument line function, which simulates the instrument's effect on the ideal spectrum, to create an apparent transmittance spectrum that mimics the actual spectrum observed from an FTIR measurement. The user inputs for the ideal transmission spectrum are path-length, gas concentrations, temperature, and atmospheric pressure.

Path-length is the distance that the infrared beam travels in the atmosphere between the source and the detector. This distance is easily measured with a range finder in the field. Paths of up to 1,000 meters can be used for the measurement of some compounds. For industrial hygiene applications and tomography, paths as short as five meters have been useful. For a monostatic system using a retroreflector or mirror, the entire round trip distance must be used because absorption occurs in both directions.

Gas concentration is the most important factor affecting the transmission spectra. Its accurate determination is the purpose of most OP-FTIR measurements. Target gases and interfering species absorb infrared energy at different frequencies across the spectrum, each decreasing the transmission of infrared energy in a unique pattern. These absorption lines can clearly be seen for $H_2O$ and $CO_2$. The presence of these gases is indicated by downward pointing peaks in the single beam spectrum at the characteristic frequencies of each gas.

Single Beam Model

To illustrate the effect of added water vapor concentration, two "simulated single beam spectra" were created by multiplying a function that represents the instrument shape $I_0$ by transmittance output from E-Trans. The instrument shape is simply a smoothed residual spectrum and is by no means, a perfect $I_0$. The reason for carrying out this step is to create spectra that represent the single beam spectra more accurately than the simple E-trans output in transmittance space. For example the band from 3300 cm$^{-1}$ to 3500 cm$^{-1}$ has about half of the intensity of the band from 2500 cm$^{-1}$ to 2700 cm$^{-1}$ due to detector response falloff. Water quantification models that use simple synthetic transmittance spectra as inputs would most likely use lines that are not optimal when applied to real single beam data.

Inputs for Gas Modeling

Concentration

The quantity that is desired as an endpoint in the present approach and almost all other OP-FTIR experiments is the concentration of interfering and target gases. The addition of an infrared absorbing gas decreases the amount of infrared radiation reaching the detector and thus in the spectra. To examine this effect, two synthetic spectra were created with different concentrations of water vapor. These two synthetic single beam spectra were created from the HITRAN database by the E-Trans software.

Two important things were observed in these spectra. First, the two absorption features get stronger as expected, with an increase of the water concentration from 10,000 ppm to 11,000 ppm. The transmission at 11,000 ppm relative to the off peak transmission is 1.68% less for 3281 cm$^{-1}$ and is 1.36% less for 3283 cm$^{-1}$. Secondly, all of the points including those between the absorption features at 3282 cm$^{-1}$ also show a decreased transmission with the additional water in the path. The entire plot for 11,000 ppm lies below the 10,000 ppm plot, which demonstrates the "water continuum spectrum" and re-emphasizes the problem of using points between features as spline points for an artificial $I_0$.

Temperature

Figure 1A:
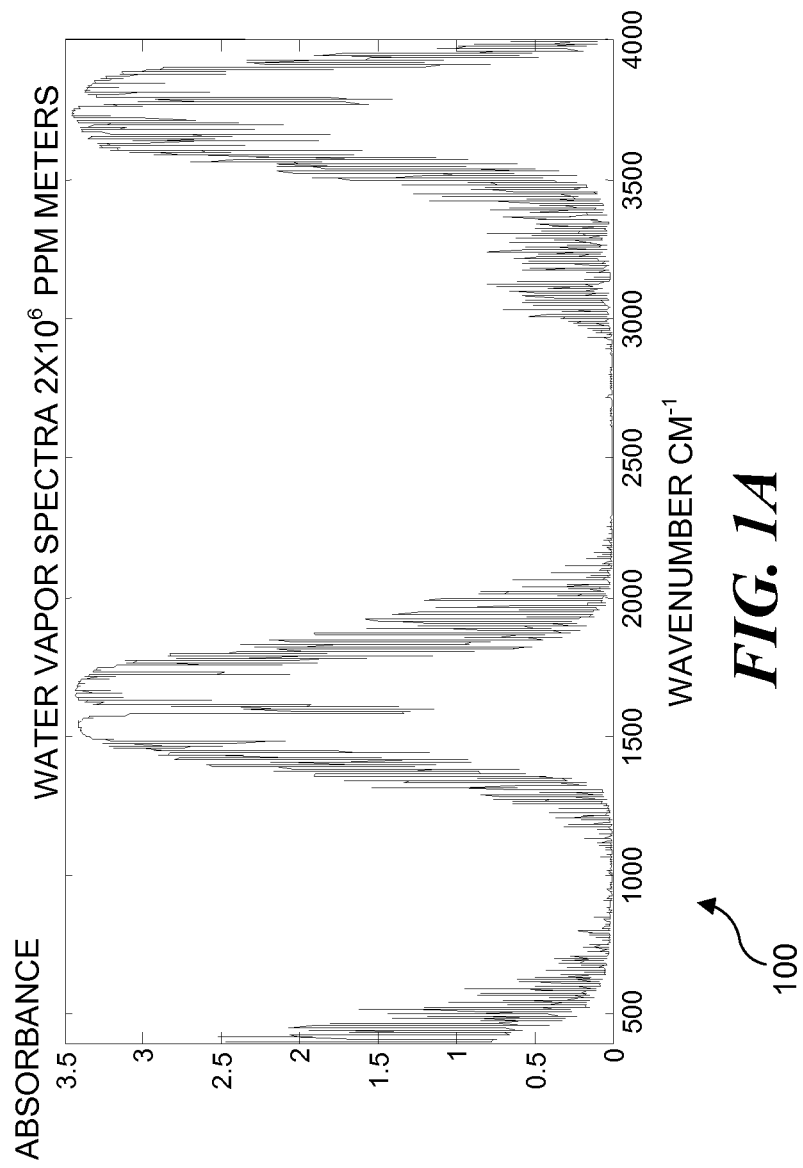
FIG. 1A is a graph of wavenumber and absorbance, illustrating the infrared absorption spectrum of water vapor.
Figure 1B:
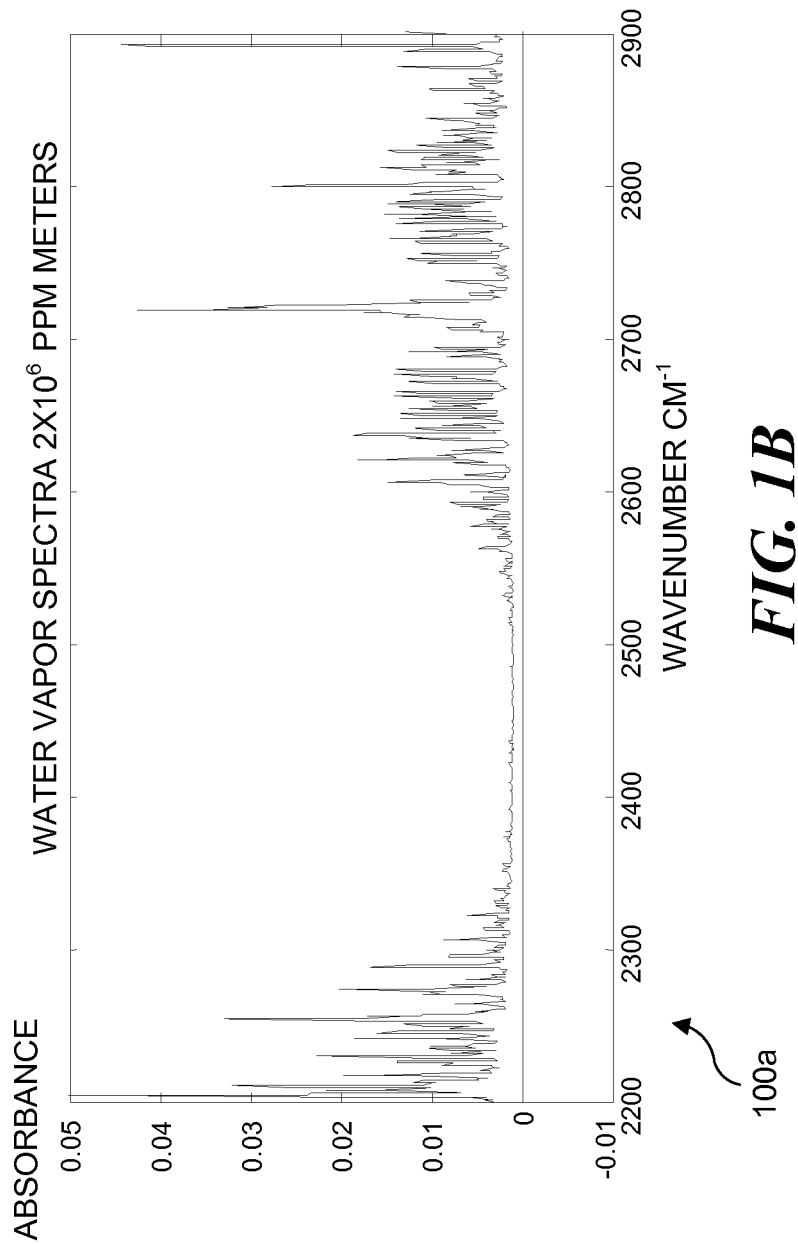
FIG. 1B is a more detailed graph of a portion of FIG. 1A that has the least water vapor absorbance.
Figure 2:
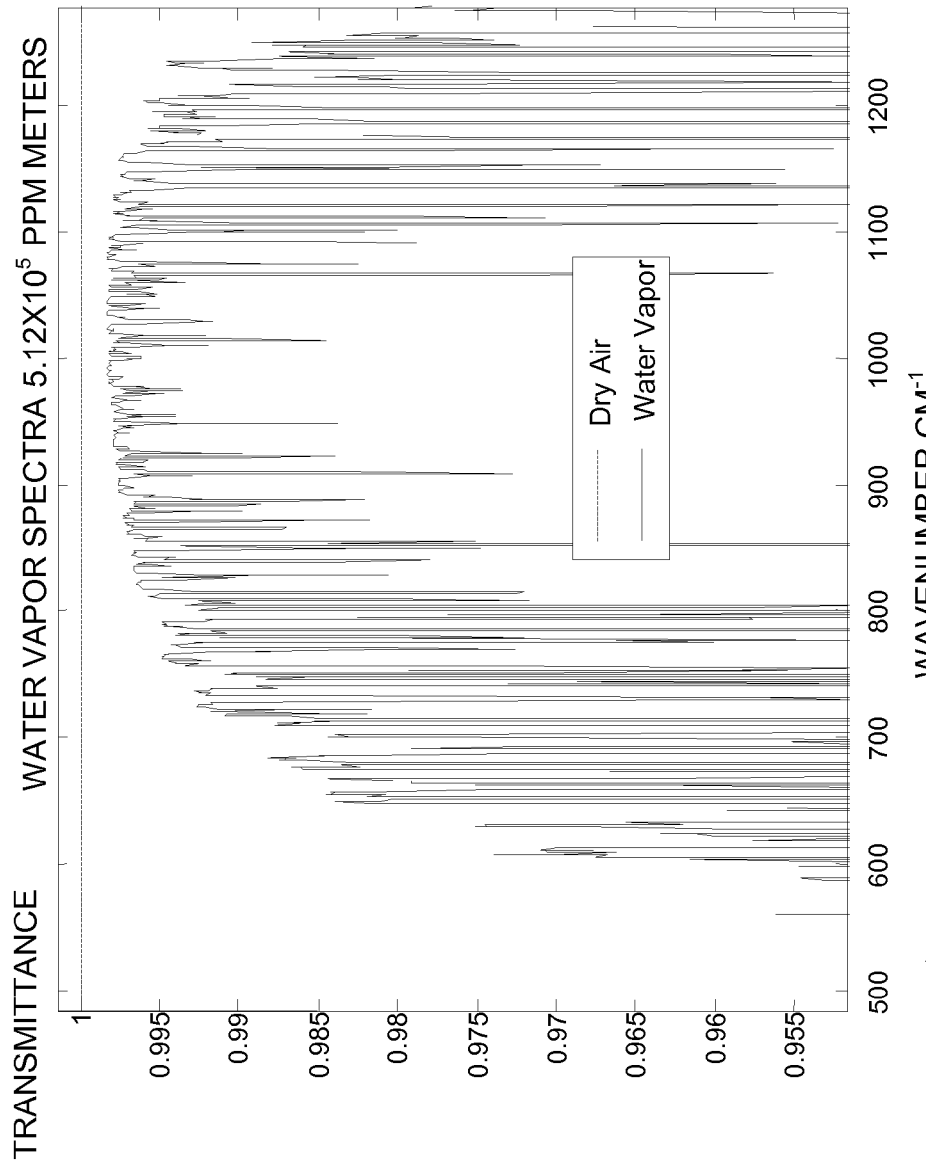
FIG. 2 is a graph of wavenumber and transmittance, illustrating the transmittance spectrum of water, from which it will be apparent that at no frequency, is 100% of the infrared energy transmitted through air even along a dry short path of 64 meters and 8,000 ppm water vapor, as shown in this exemplary data.
Figure 3:
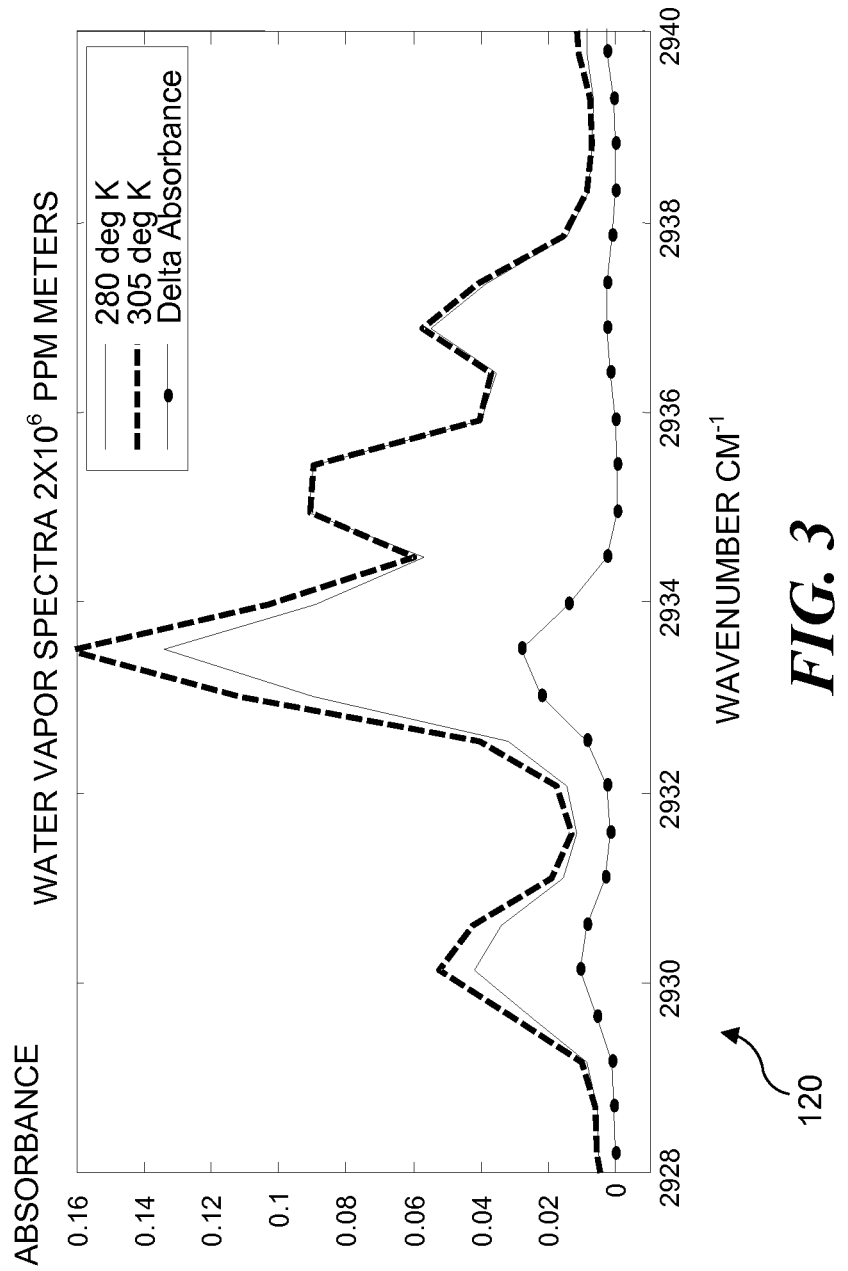
FIG. 3 is a graph of wavenumber and absorbance, showing the differences in a single water vapor absorption line with temperature, wherein the feature at 2934 $cm^{-1}$ has temperature dependence, while the feature at 2935 $cm^{-1}$ does not.

Temperature effects in the spectra of small gases arise from the changing distribution of molecules in different energy states. In an exemplary graph 120 illustrated in FIG. 3, this effect was shown in absorbance space for a single water vapor line at 2934 cm$^{-1}$. The water spectrum at 305° K shows more absorbance than the same concentration at 280° K, so the difference [305° K-280° K] showed positive delta absorbance. This absorbance is referred to herein as a "hot line." There are also many lines that exhibit the opposite effect with decreasing absorbance at higher temperatures. These lines will be referred to as "cold lines." In transmission space and single beam space, the hot lines will still be stronger at higher temperatures, but since they are negative peaks, they have a numerical value that is lower at higher temperatures. This fact is because higher absorbance results in lower transmittance.

The transmission line at 3281 cm$^{-1}$ showed more transmission at the higher temperature, meaning less absorbance, indicating that it is a "cold" line. The line at 3283 cm$^{-1}$ is a "hot" line. The magnitude of this effect is very important; the cold line at 3281 cm$^{-1}$ had a −2.78% change in transmission relative to the background points, and the hot line at 3281 cm$^{-1}$ experienced a 3.52% increase.

To put this finding in perspective, the magnitude of the average change in single beam intensity of these two water vapor lines was 3.15% for the 25° C. temperature change and only 1.5%. for a change in concentration from 10,000 to 11,000 ppm. This range of temperatures is equivalent to the overnight change in temperatures documented below in the experimental part of this disclosure. The absolute value of differences in transmittance of these lines is on the order of 0.1 percent per ° C. Therefore, a 1° C. change between the temperature when acquiring the background spectrum and the temperature when acquiring the analytical spectrum would cause errors of ~100 ppm. Knowing the water content of the air to this accuracy may not be an important goal, but the 100 ppm equivalent water vapor absorbance left in the residual spectra due to the temperature effect can cause significant difficulty with the quantification of trace gases. It is clear from this comparison that for quantification and/or subtraction of water to be optimized, the correct temperature must be used for the reference spectra.

Pressure

The final parameter that is required as an input to the ideal transmission spectra is pressure. At ambient surface conditions, the range of possible atmospheric pressures is not sufficient to alter the shape of the infrared spectra in a significant way. However, the transmission spectra will become weaker with decreasing pressure, due to the fact that there are fewer molecules per volume.

To explain this effect, reexamine Eq. (1), which is repeated below.

$$I_A(v)=I_0(v)e^{-\alpha(v)CL}. \quad (1)\text{—Repeated}$$

The exponent $-\alpha(v)CL$ can be broken up into three parts, where $-\alpha(v)$ refers to the absorption cross-section at a given (v) and has the units $$\frac{Meters^2}{Molecule};$$

L refers to the path length and has the units Meters; and C refers to the concentration and has the units $$\frac{Molecule}{Meters^3}.$$

Beer's law is based on the number of molecules in the sample path, which means that it is based on mass. Typical units for measuring gases in air, such as parts per million (ppm), or parts per billion (ppb), are volume ratios of gases to the total number of molecules present. The open atmosphere does not have a constant density due to pressure and temperature fluctuations. Thus, a volume based concentration measurement, such as ppm or ppb, must take into account pressure and temperature as the number of $$\frac{Molecules}{Meters^3}$$

changes.

The Ideal Gas Law is Stated as:

$$P_i V = N_i k T \quad (4)$$

where:

$P_i$=Partial pressure of trace constituent;

V=Volume of sample;

$N_i$=Molecules of trace constituent;

k=Boltzmann's Constant; and

T=Temperature in Kelvin.

It follows that $$\frac{N_i}{V} = \frac{P_i}{kT},$$

and that $$C = \frac{\text{Molecules}}{\text{Meters}^3} = \frac{N_i}{V} = \frac{P_i}{kT}.$$

Then combining with Eq. (4):

$$I(v) = I_0(v)\exp^{\left(-\alpha_i(v)\frac{P_i}{kT}L\right)}. \tag{5}$$

It can be seen from Eq. (5) that the value of the exponential is directly related to the value of $P_i$ and L and inversely related to T. An increase in pressure, $P_i$, results in more molecules $N_i$ in the sample beam, and a decrease in Volume, V, results in fewer molecules $N_i$ in the sample beam. Volume is equal to beam area multiplied by path length. Therefore, these two parameters, pressure and path length counteract each other in terms of the transmittance spectrum. Although large changes in pressure can alter the line shape through collision broadening of the features, over the range of pressure changes encountered near the earths' surface, this effect is minimal. For example, the three conditions listed in the Table 1 below would have the same infrared spectrum.

TABLE 1

Combinations of pressure, concentration, and path-length create identical spectra

| Path-length (Meters) | Concentration (ppm) | Pressure (torr) | Temp (K) |
|---|---|---|---|
| 100 | 1,0000 | 760.0 | 300 |
| 99 | 1,0000 | 767.7 | 300 |
| 100 | 9900 | 767.7 | 300 |

Temperature also has an effect on the molecules $N_i$ in the sample beam. However, since temperature changes $\alpha_i$, the features change shape as well as size. The effect is more complex than that of pressure or path-length. An error in temperature cannot be compensated by adjusting any other input parameters in the synthetic spectra process. Therefore, there is no temperature other than 300° K that would create identical spectra to the ones in Table 1 at a different pressure or path or concentration. This conclusion means that the temperature must be accounted for independently, but at ground level, pressure can be accounted for in the concentration-path length term. In situations where substantial pressure changes may occur, such as vertical profiles in the atmosphere, pressure also must be accounted for as an independent term in the model. Pressure, concentration, temperature and path-length all contribute to the number of molecules $N_i$, in the sample volume according to the Ideal gas law. This same $N_i$, molecule number fits into the numerator of the concentration, $$C\frac{\text{Molecule}}{\text{Meters}^3}$$

component of the Beer's law exponent.

After path length, gas concentration, temperature, and pressure have been chosen, it is possible to determine a "perfect transmittance spectra" or "true spectra" from the HITRAN database. The transmittance spectra are created one absorption feature at a time. Each feature is the result of a single transition from a lower energy state $E_0$ to a higher energy $E_1$. To model the effect of a single transition on the spectrum, several parameters are required. The magnitude of the feature is determined by the integrated line strength S. This is a measure of the total area of the feature at any pressure or temperature. The pressure and temperature effects are also feature-specific, and an additional parameter is needed to define a given feature at different temperatures and pressures. Lorentzian half widths $\alpha_L$ that are a function of pressure and temperature fulfill this purpose.

For each absorption line, the HITRAN database provides line frequency $v_0$, integrated line strength S, lower state energy level $E_0$, and pressure and temperature dependent Lorentzian half widths $\alpha_L$. Individual absorption lines are created from these parameters. For water vapor, there are thousands of these lines that contribute to the FTIR region from 400 $cm^{-1}$ to 4,000 $cm^{-1}$. These lines are then superimposed in absorbance space and converted to transmittance space to create high resolution 0.06 $cm^{-1}$ transmittance spectra that represent the true spectrum T(v).

Instrument Modeling

The model so far is a model of how a gas, in this case, water vapor, physically interacts with infrared radiation in the sample beam. This result is what a spectrometer with no noise, no spectral shift, and nearly infinite resolution would record. Of course, real instruments have noise, spectral shift, and finite resolution. The rest of the process of synthetic spectra creation is a modeling of how a true instrument operates physically and optically to record the real spectrum. The process of converting the actual transmission spectra to an observed transmission spectra can begin once the laser frequency, spectral shift, resolution, and apodization have been determined. Variations of a Fourier convolution method have been used by Phillips at Spectrosoft software. Etrans is the software method used in the present exemplary approach.

If $I_0(v)$ represents the zero gas path source intensity, then the true intensity I(v) is the product of $I_0(v)$ and T(v), where T(v) represents the true transmission created from the individual Lorentzian lines.

$$I(v) = I_0(v)T(v). \tag{6}$$

The observed or measured spectral intensity $I_m(v)$ is given approximately by:

$$I_m(v) = D(v)\int_{-\infty}^{\infty} f(v+x, R)I(x)\,dx \tag{7}$$

$$= D(v)\int_{-\infty}^{\infty} f(v+x, R)I_0(x)T(x)\,dx. \tag{8}$$

The integral is a result of a Fourier convolution of the instrument line shape function [$f(v+x, R)$] with the incident intensity. In the above equation, f(x) represents the integral normalized instrument line function containing resolution and apodization information. D(v) is an instrument response function including information on the detector, the optics, and the electronics and other instrumental factors. Since the source intensity $I_0(v)$ changes very slowly with frequency, $v$, relative to individual pixels, the above equation can be approximated as:

$$I_m(v) = I_0(v)D(v) \int_{-\infty}^{\infty} f(v+x, R)T(x)dx. \qquad (9)$$

Note that the product of $I_0(v)D(v)$ is the zero gas single beam spectrum. In terms of measured quantities the equation becomes:

$$I_m(v) \approx I^0_m(v)T_m(v) \qquad (10)$$

where the measured transmittance is the convolution of the true transmittance and the instrument's line function.

$$T_m(v) \approx \int_{-\infty}^{\infty} f(v+x, R)T(x)dx \qquad (11)$$

Figure 8:
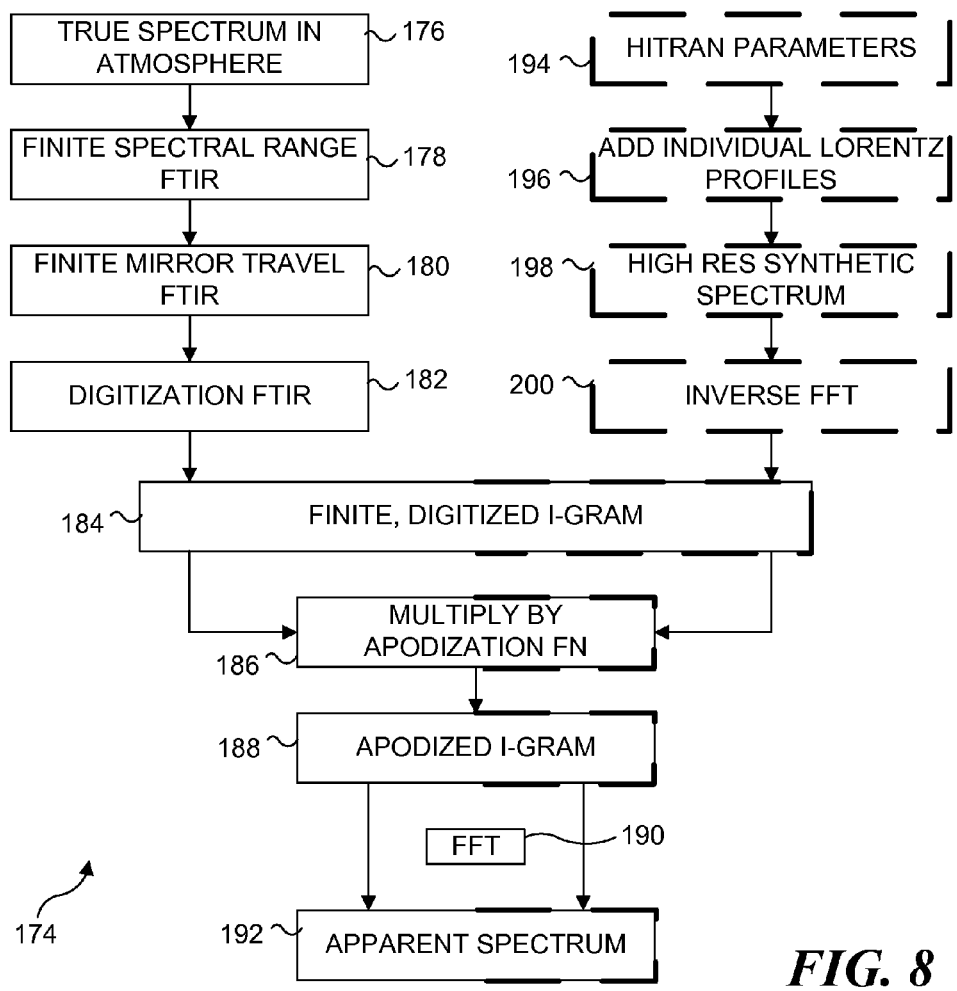
FIG. 8 is a graph illustrating an exemplary single beam spectrum from an OP-FTIR system.

A summary 174 of how the E-trans software mimics the actual FTIR spectrometer convolution is outlined in the schematic flowchart displayed in FIG. 8. The flowchart presented in this Figure represents a "state-of-the-art" technique for creating a synthetic reference. The left side of the flowchart (solid boxes) shows the path of the data from a true spectrum in the atmosphere through the OP-FTIR instrument. A first step 176 represents the true spectrum of a gas in the atmosphere absorbing radiation of all frequencies. A second step 178 indicates that the detector, source, and other optical elements prevent the instrument from observing frequencies above or below certain limits. A third step 180 shows that the moving mirror of the interferometer only moves for a finite distance, limiting the resolution of the FTIR causing the fine lines of small molecules like water vapor to be grouped into larger frequency intervals. A next step 182 shows that the interferogram is a digitally sampled version of the continuous interferogram that exists. There is significant over sampling for the mid-infrared as the wavelength of the laser is in the visible spectrum. No information is lost but noise is introduced via the imperfect timing of the zero crossings. Steps 176-182 represent ways that the physical reality of the instrument alters the true spectrum. The end result is step 184, which is a finite digitized interferogram (I-Gram) recorded by an instrument.

On the right side of FIG. 8, the flow of data in the simulated spectra is detailed. The starting point at a step 194 refers to the line parameters from the HITRAN or other database, which is the basic information that is needed to define each transmission line. A Lorentzian profile is then calculated (a step 196) for each transmission feature and then they are all summed into a "true spectrum" (a step 198). This spectrum needs to be much higher resolution than the final apparent spectrum, because the features of many atmospheric gases are significantly sharper than the final apparent spectrum. In a step 200, an Inverse FFT (IFFT) is now performed on this high resolution synthetic spectrum, which is analogous to the interferometer sampling the actual detector. This IFFT results in a finite digitized interferogram in step 184, where the two flowcharts merge. A next step 186 for both the instrumental and synthetic processes is the multiplication of the interferogram by an apodization function. Finally, a Fast Fourier Transform (FFT) 190 is applied to the data to create an apparent spectrum in a step 192.

Inputs for Instrument Modeling

There are four user inputs for the process of transforming a "true" water transmission spectrum into an instrumental water transmission spectrum. They are apodization, laser frequency, spectral shift, and resolution.

Apodization

As stated above, the raw data from the FTIR comprises an interferogram, which is a record of voltage at the detector through the range of motion of the mirror (retardation) in the Michelson interferometer. The distance that the mirror travels is finite, which imposes a limit on the resolution of the spectrometer. There is another important result of the mirror travel being limited. The point at which the mirror stops moving, the interferogram abruptly stops being recorded in retardation space. If the mirror were to travel for an infinite distance, the line could be fully reproduced from the series. Since the mirror has to stop in the real world, only a subset of the infinite series can be sampled. The term "boxcar" refers to the shape of a function by which the real infinite interferogram is multiplied. The sampling simply stops, and the interferogram is either on or off. The truncation causes a ringing in the spectrum, because the transform cannot handle the rapid step function. The spectrum adds width and takes on positive and negative lobes. These lobes create problems with the further evaluation of the spectrum. The use of an apodization function makes this transition less of a problem, by slowly tapering the interferogram from a value of 1 at the centerburst, to a value of 0 at the limit of mirror travel. Apodization increases the line width, but removes the lobes or "feet." The term apodization literally means "without feet." Triangle apodization is commonly used in OP-FTIR and is used throughout this discussion due to availability of references and limitations of the bgrams software that interfaces with this model of the ETG Airsentry™ OP-FTIR.

In addition to the apodization function chosen there is further apodization that occurs due to the limitations of the instrument. Even in a well aligned FTIR, the spectrometer will apodize itself to some degree. This effect is an additional apodization and decreases the resolution still further. A main source for this is the divergence of the infrared beam in the spectrometer due to the finite size of the source and/or detector. These issues are managed by applying an apodization function that reaches zero before the end of the interferogram.

After apodization of the inverse FFT of the "perfect transmission" spectrum, an FFT is performed to return to the frequency domain. Now this synthetic apparent spectrum has the same resolution, line width, and line shape as the field measurement obtained from the modeled instrument. The residual noise for this type of operation can be as low as $10^{-5}$ Absorbance units (Au). With this level of accuracy in the synthetic transmittance reference spectra, the concentration calculations will be limited by the actual noise of the measurement, not by the effective method noise from errors in temperature, shift, and resolution. The E-trans™ and Nonlin™ computer codes developed by Spectrasoft Inc. use this technique to create spectra for water, $CO_2$ and several other gases for use in OP-FTIR work. All synthetic spectra referenced in this discussion were created with E-trans™. The Nonlin™ program is more complex and actually uses these synthetic spectra to quantify gases. For each single beam intensity spectrum, Nonlin™ requires an input temperature. Nonlin™ determines spectral shift and resolution for each input spectrum and creates appropriate reference spectra based on these quantities and the input temperature. Then, the Nonlin™ code quantifies the amount of water and several other interfering species as well as target gases in the input spectrum using a polynomial background to calculate absorbance. The user input of temperature is crucial, because the calculated spectra for several of the gases, especially water vapor, are highly temperature dependent.

Laser Frequency

The laser frequency refers to the laser that is used by the interferometer to determine when data-points are digitally sampled in the interferogram. This laser passes through the same interferometer as the infrared light. As the mirror moves, the monochromatic light of the laser goes through cycles of constructive and destructive interference. A separate detector monitors these cycles. The zero crossing points recorded by this detector create an internal standard for the accurate determination of the mirror position in time based on the wavelength of the laser, which allows the voltage measurements at the infrared detector to be assigned to the correct optical path difference in the interferogram. The optical path difference is referred to as the retardation. Small shifts in the frequency of the laser contribute to shifts in the location and spacing of spectral data-points in interferogram space and wave-number space of the subsequent spectra. For the spectral modeling in an exemplary method discussed in this disclosure, the laser wavelength was known to five decimal places in wave-number space.

Spectral Shift

Spectral shift is the difference in wavenumber between where a feature actually is and where the spectrometer records it in wavenumber space. Many optical and physical instrumental parameters can contribute to the overall spectral shift. Changes in retro-reflector location and alignment have an impact on this parameter and can change over time in an open path system. Another factor that can contribute to spectral shift and can change over time is the thermal effects on the physical alignment of the interferometer. Changes on the order of 0.5 $cm^{-1}$ have been reported in the literature and seen in the ETG AirSentry™ OP-FTIR. The infrared spectra of small molecules such as $H_2O$, $CO$, and $CO_2$ are most affected, because they have sharp features that are finer than the resolution of the instrument. The shift can be determined from the single beam spectrum by comparing the location of a known line feature to the apparent location determined by the instrument.

As the spectral shift of an OP-FTIR instrument changes, it causes corresponding errors to appear in the spectrum. For example, the fine water line at 2044.3 $cm^{-1}$ contributes to the neighboring spectrometer intervals in frequency space in different ratios. The difference between the 0.41 $cm^{-1}$ and the 0.2 $cm^{-1}$ spectral shift can easily be discerned, while the smaller shift difference from 0.39 $cm^{-1}$ to 0.41 $cm^{-1}$ is harder to discern. What is important is how this parameter affects the ability of the spectrometer to quantify gases in the path. The Limit of Detection (LOD) of a spectrometer for a specific gas at a specific waveband is based on the relative size of the absorption feature to the noise in the spectrum. Generally, the feature of the target gas needs to be three times the root mean square (RMS) noise. There are several sources for this noise that include actual instrumental noise and apparent or "method noise." One source of method noise is the use of backgrounds and/or references with different spectral temperatures, shifts, and resolutions. The single beam spectrum has a given shift and resolution that may not be the same as a background, even if that background is from the same spectrometer on the same day. These sources of method noise arise when a double beam transmittance spectrum is created. They exist in the double beam transmittance spectrum and the subsequent absorbance spectrum, but not in the single beam.

A slight change in spectral shift between a sample and a background can effect the resulting absorbance calculation. For example, the spectral shift will be altered on simulated single beam spectra from 0.41 $cm^{-1}$ to 0.36 $cm^{-1}$, while all other parameters are held constant. This range of spectral shift has been seen in the experimental portion of the present work. The differences in calculated transmittance of these lines relative to the background points at 3282 $cm^{-1}$ are on the order of 0.4% or less, which is negligible when compared to the effects of temperature and concentration on these same lines. However, even when a correct determination of water line transmittance and concentration is made, the effects on the residual spectrum after the subtraction can be considerable. The residual spectrum is the spectrum that remains after the calculated amount of water absorbance is subtracted from the absorbance spectrum or divided out of the intensity spectrum. The same residual errors would remain in a single beam transmission space after a division by a reference transmission spectrum. Therefore, to minimize possible errors, a correction for spectral shift should be applied when possible, to either the transmission reference spectra, or the sample spectrum to align the frequency domain of the reference transmission spectra with the single beam transmission spectra generated by an instrument in field conditions. It should be understood that a spectra shift in either the sample data or the reference transmission spectrum data can cause unacceptable errors, and that these errors can be minimized by matching the spectral shift of the reference transmission spectra data to the spectral shift in the sample single beam data. Also, it should not matter which way the alignment is performed (either the reference transmission spectra or the single beam spectra can be moved). The important point is that they should both align as closely as possible in frequency space.

It is impossible to have greater than 100% transmission, but that is precisely the result when an error, in this case a change in the spectral shift, occurs that records $I_A(v)$ as being greater than $I_0(v)$. However, this makes no physical sense. At 3280 $cm^{-1}$ in the percent transmission plot, there is a value above 101%, which also does not make physical sense unless there is some emission of energy at this precise wavelength in the exact direction of the FTIR beam at this time. At the next point in wave-number space, the situation is reversed. Specifically, at 3281 $cm^{-1}$ the sample beam has a smaller value than the background, which is expected. At this wave-number in the percent transmission plot, the value is 98%, which is physically possible, but in this case is an error due to shift. The correct result of this transmission calculation would be a flat line at 100% because there is nothing in the sample beam that is not in the background as well. The mean of this plot is 100% transmission, because any error on the left side of a line has an equal and opposite error on the right side. Therefore, the result of a shift error is an apparent increase in the RMS noise in the transmission and absorbance spectra.

The next step in traditional OP-FTIR quantification is the calculation of the absorbance. Absorbance is calculated from the percent transmission data, and the error in shift alone can be up to 0.02 absorbance units. This error is a very large number, since the noise of a typical instrument can be 200 times less than this value. These errors are similar to the errors in transmission, but with the opposite sign. The absorbance errors from a shift change average to zero over a wave-number range significantly larger than the feature width.

Method noise resulting from a change in spectral shift between the background and sample spectra occurs across the entire mid-infrared spectrum. In the field, spectral shift can vary across a range of values. The amount of method noise absorbance is directly proportional to the amount of shift. An instrument noise value of $10^{-4}$ is a typical quality assurance goal for OP-FTIR. Small amounts of shift error (0.005 $cm^{-1}$, 0.01 cm$^{-1}$, and 0.02 cm$^{-1}$) cause absorbance method noise less than 10$^{-4}$ and do not add to the instrument noise. The values 0.05 cm$^{-1}$ and 0.1 cm$^{-1}$ have been observed to create higher than 10$^{-4}$ values in absorbance space, resulting in higher noise and potentially affecting the ability of the FTIR to detect and quantify target gases in this region.

Above 0.05 cm$^{-1}$, the shift differential results in enough absorbance to equal an instrument noise of 10$^{-4}$ absorbance units. For example, at 2500 cm$^{-1}$, even a shift error of 0.1 cm$^{-1}$ does not result in damaging levels of method noise, while at 3100 cm$^{-1}$, a shift of just 0.005 cm$^{-1}$ causes difficulties. This result is due to the far greater amount of water absorption at the higher frequencies.

The end result of these errors is a loss of spectral band that is limited by instrument noise. When the method noise from shift errors is greater than the instrument noise, it becomes the limiting factor if an analyte can be identified and quantified. The bands that are instrument noise limited shrink as the error in shift between the background spectrum and the analytical spectrum increases. It is important to note that analytes can still be identified and quantified in the lost bandwidths, but not at as low a concentration. The LOD for gases may be increased by the method noise.

Resolution

Resolution is a defining quality of a spectrometer. It refers to the bandwidth that contributes to the recorded signal of an individual pixel or data-point in frequency space. Higher or finer resolution indicates that a smaller range of wavelengths in the electromagnetic spectrum can influence an individual data-point. In FTIR spectroscopy, the distance that the mirror travels is inversely proportional to the possible resolution. As the mirror travels farther in centimeters (greater retardation), the ability of the spectrometer to distinguish between two distinct lines at different wave-numbers becomes better. If two absorption lines have a separation $\Delta v$ ($v_1-v_2$) cm$^{-1}$, then they become out of phase after a retardation of $0.5(\Delta v)^{-1}$ and become back in phase again after a retardation of $(\Delta v)^{-1}$.

The best resolution that can be obtained is therefore given by:

$$\Delta v = (\Delta_{max})^{-1}.$$

When a user is selecting a resolution on an FTIR, the distance that the mirror moves per scan is the parameter that is being adjusted. There has been considerable discussion in the literature as to what resolution is best for the determination of gas concentrations by OP-FTIR. Higher resolutions, i.e., 1 cm$^{-1}$ and higher, have the advantage of being able to better resolve the finer features in the smaller molecules like CO, NO, H$_2$O, and NH$_3$. These high resolution interferograms require a longer mirror travel, so more points are required to completely record it. Therefore, these interferograms are slower to acquire. Higher resolution interferograms and subsequent spectra are also noisier. The lower resolution spectra are faster to acquire, so they are less affected by a changing atmosphere and also contain less instrument noise. Most OP-FTIR systems have resolution as an adjustable parameter, because the best resolution for a specific application depends on the target gases and interfering gases expected. In FTIR, the nominal resolution refers to the number of points per wave-number in the frequency domain, based on the mirror movement. However, two different spectrometers, or the same spectrometer at different times, can have the same nominal resolution and different actual resolutions. This result is due to neighboring data points being influenced more or less by each other, as the actual physical bandwidth of energy that affects a given pixel increases and decreases. Differences in ambient temperature and slight movements of the retro-reflector can cause a change in resolution with open path spectrometers. The instrument used for the experiments in the exemplary embodiment employed for evaluating the novel approach was observed to have resolutions between 1.1 cm$^{-1}$ and 1.35 cm$^{-1}$. Resolution has been seen to change, along with spectral shift, during OP-FTIR experiments on the timescale of hours.

Following the data processing, a transmission spectrum is calculated using resolution 1.20 cm$^{-1}$ as a sample and resolution of 1.15 cm$^{-1}$ as a background. The actual water peaks that were observed during this step all showed a percent transmission above 100 due to the sample beam apparently having more transmission than the background. The points between actual water lines all have less than 100% transmission.

Finally the absorbance spectrum is calculated from the transmission and method errors greater than 0.02 absorbance units are seen. If the sample and background are reversed, then the absorbance and transmission spectra of these errors become a mirror image, and the RMS method noise errors are unchanged. This mirroring effect of the absorbance and/or transmission errors would occur if the direction of change of any of the instrumental or environmental sources method noise errors were reversed (shift, temperature, concentration, apodization laser frequency, or even pressure/path-length product).

The error in spectral resolution of 0.05 cm$^{-1}$ is seen here to create absorbance errors of up to 0.015 absorbance units. This is less than the effect of changing shift the same amount (0.02 absorbance units), but still considerably more than instrument noise for this spectral region. In the field, these two parameters are both changing at the same time and the errors can be additive. These effects have all been demonstrated at 10,000 ppm H$_2$O and 64 meters, which is a relatively short and dry path for OP-FTIR, and the errors would increase proportionally with wetter and longer path lengths.

Spectral Regions

These spectral parameters and their effect on the absorbance have so far been discussed in an area of the spectrum that has considerable water vapor interference. This area of the infrared spectrum is usually not useful for longer path OP-FTIR gas measurement, mostly due to this water vapor interference. However, this area was chosen to demonstrate the effects of temperature due to the existence of strong hot and cold water vapor lines and good instrumental signal strength. To evaluate the importance of modeling all of these parameters in the creation of water vapor reference spectra, other regions of the infrared region must be examined. The importance of the improved modeling is the lowering of LODs and increased accuracy for target gas concentration calculation. To understand if and to what extent these goals can be achieved, the magnitudes of instrument noise and method noise must be compared in the regions of interest at expected concentrations of water vapor. Instrument noise is the unavoidable noise that arises from various physical facts of the spectrometer. The detector is the most important source of this noise, but there are other sources such as digitization noise from the analog/digital converter and sampling noise from very small errors in the sampling of the interferogram in the time domain. Method noise comes from changing factors such as the errors in shift, resolution, temperature, concentration of known interfering gases, and existence of unknown interfering gases. Several sources of method noise have been discussed above, and the reduction or elimination of these is a desirable goal.

Fingerprint Region

There are three regions that are relatively free of absorption from H2O and $CO_2$ that have good signal at the detector. The first is 700 $cm^{-1}$ to 1200 $cm^{-1}$, which is often referred to as the fingerprint region. Many hydrocarbons in the Clean Air Act Amendments of 1990 have unique absorption features in this region. Also, the Environmental Protection Agency (EPA) method TO-16 uses a part of this region (980 $cm^{-1}$ to 1020 $cm^{-1}$) for signal strength and noise calculation for OP-FTIR quality assurance and quality control. In one empirical test, the false absorption features "method noise" created by differences in the various modeling parameters were compared to actual instrument noise from the ETG AirSentry™ OP-FTIR. This quantity for instrument noise was calculated by using 50 single beam spectra from the AirSentry™ OP-FTIR interleaved to create sample and background spectra. Each single beam was a result of five instrument interferograms that required about 4.3 seconds each to record. This amount of noise represents slightly less than nine minutes of averaging, which is longer than typical OP-FTIR measurements that might tend to underestimate instrument noise and therefore overestimate the effects of method noise in comparison. However, the TO-16 based RMS noise calculation for these spectra was 0.0003, which is higher than most commercial instruments claim to have, so it appears that the comparisons are valid.

Several important ideas were developed based on this test. First, it was noted that the EPA region for noise calculation (980 $cm^{-1}$ to 1020 $cm^{-1}$) represented the best part of the fingerprint region to avoid water vapor. The various sources of water vapor-based method noise are all at minimum from 980 $cm^{-1}$ to 1020 $cm^{-1}$. Another important observation was that the plot of temperature changes was the largest for almost this entire region. It is important to note that this was an extreme case of temperature change, but none the less, an actual one recorded overnight in Yakima, Wash. in July of 2006. The temperature-based errors were 10 times greater than instrument noise for most of this region, implying that a temperature error of just 2.5° K would be enough to dominate the instrument noise and decrease the ability of the OP-FTIR to identify correctly and quantify target gases in much of this important region of the spectrum. Another interesting feature of the plot was that the temperature induced method noise has a broad-based effect on the continuum spectrum in addition to the very large effects on the peaks. Concentration has a similar, but opposite, effect as expected, which implies that $I_0$ assumptions made between water lines would be affected by ambient temperature as well as by water vapor concentration. This observation also implies that using this area for determination of signal strength may be prone to temperature-based errors. Unlike the temperature-based errors, the shift and resolution errors and instrument noise all average to a value of close to zero over the entire fingerprint region.

The magnitude of any type of water vapor-based method noise is proportional to the amount of water vapor absorbance. In a previous test discussed above, the path-length was 64 meters, and the water vapor concentration was 10,000 ppm, resulting in a concentration path product of $6.4 \times 10^5$ ppm·meters. The relative magnitudes of the three sources of method noise in the fingerprint region of the spectrum were smoothed with a 25 $cm^{-1}$ wide moving average to make the resulting plot easier to read. All values in this region are positive because the plot was a measure of magnitude. A temperature differential of 1° K dominates from 750 $cm^{-1}$ to 1,100 $cm^{-1}$. Above and below this band, the shift effects of 0.01 $cm^{-1}$ are larger than the temperature effects. Resolution plays a smaller role throughout the region.

This path-length used in this experiment was a very dry, short path that represents the approximate conditions during most of the experimental part of this investigation. To understand the consequences of the various sources of method noise throughout the range of typical OP-FTIR field conditions, the calculations were repeated with different amounts of water and longer path-lengths. For example, the same water vapor-based method noise calculations were made at a path-length of 200 meters and a concentration of 20,000 ppm, yielding $4 \times 10^6$ ppm·meters, and at a path-length of 400 meters and 20,000 ppm, yielding $8 \times 10^6$ ppm·meters.

A path integrated concentration of $4 \times 10^6$ ppm·meters is a more typical amount of water vapor for an OP-FTIR measurement. For the test at a path-length of 200 meters, it is clear that all of the effects except instrument noise are greatly enhanced with this amount of water vapor. The temperature effect at 1° K is ten times the instrument noise, and even the resolution effect is at or above the target instrumental noise level of 0.0001 absorbance units for the entire length of the fingerprint region. In this water regime, the shift and resolution errors are larger than the instrumental noise, and the temperature effect is larger still. There was no significant portion of the fingerprint region in these tests, where instrument noise is the limiting factor.

An important observation in these tests was that the temperature now dominates the shift from 700 $cm^{-1}$ to 800 $cm^{-1}$, unlike in the earlier tests. This point is notable because it illustrates that these factors must be accounted for on a case-by-case basis; their relative importance can vary, depending on the ppm·meters regime.

A value of $1.2 \times 10^7$ ppm·meters represents a level of water that has made the method of OP-FTIR unusable in the past. In the $1.2 \times 10^7$ ppm·meter plot, even the shift errors are much larger than instrument noise, and the Y scale had to be altered to keep the temperature effects at this regime on the graph. An interesting fact became apparent on the $1.2 \times 10^7$ ppm·meters plot: the baseline effects of temperature overpower all other parameters including the temperature effects on the peaks. An ambient temperature differential between a sample beam and a background beam with this much water could be mistaken for particulate scattering.

CO Region

The second area of the infrared spectrum that is useful in OP-FTIR is the region from around 2,000 $cm^{-1}$ to around 2,300 $cm^{-1}$, depending on path-length and water concentration. High levels of $CO_2$ can reduce the higher end to 2,250 $cm^{-1}$ in combustion situations.

As was the case in the fingerprint region, the effects on the water spectra from a strong diurnal temperature signal are greater than the effects of a 10% change in concentration for $H_2O$ and far greater than instrumental noise. Another point about this region of the spectrum is that CO and $NO_X$ are all present as interfering species, and these gases also are subject to the same sources of method noise as water vapor, but at far lesser concentrations. The last plot only contained $6.4 \times 10^5$ ppm·meters water vapor. When the water content was increased to the more typical $4 \times 10^6$ ppm·meters, the effects are greatly increased. Clearly, the inclusion of a multidimensional water vapor spectral model is essential in this region.

CH-Stretch Region

The final area for successful OP-FTIR spectroscopy is the CH stretch region from around 2,300 $cm^{-1}$ to around 3,200 $cm^{-1}$. Energy at these frequencies is absorbed by the stretching of carbon-hydrogen bonds in organic molecules Infrared techniques have their history and nomenclature routed in organic chemistry. The utility of this technology in open path work is limited by increasing water vapor interference on the high wavenumber end at longer path-lengths. Working above 3,000 cm$^{-1}$ is not possible with longer paths, in humid conditions. It was empirically shown in one exemplary test that the area from 2,400 cm$^{-1}$ to 2,600 cm$^{-1}$ is relatively free of water, and that the instrument noise is the limiting factor. Another observation is that the deuterated water vapor (HDO) bands from 2,600 cm$^{-1}$ to 2,800 cm$^{-1}$ and a large peak near 2,725 cm$^{-1}$ are all negative with the positive temperature change. Sometimes HDO is used to quantify water vapor, because the HDO features are removed from the overpowering and often opaque areas of the mid-infrared spectrum dominated by $H_2O$. This area of the spectrum also has strong instrumental throughput and detector response making it an ideal band to quantify water. The temperature effects on water will create a negative bias to any water quantification based on these features in addition to the method noise problem. Another point that was evident from this test is that the usable bandwidth toward the higher frequencies will be pushed upward with improved water reference creation and subtraction. In the lower frequency domain, there is little water and thus little or no method noise from water errors, even at $4\times10^6$ ppm·meters. As the frequency increases, the HDO lines are encountered. An incorrect water temperature reference here may produce a bad number for water concentration, but probably not a very poor subtraction, since all of the errors are negative, and any error in temperature probably would not be as great as the 25° K in the test. The shift and resolution are starting to rival the noise here but not overpower it.

Beyond 2,900 cm$^{-1}$, the difficulties become much worse. Shift errors and temperature errors become very much larger than instrument noise and must be accounted for to obtain favorable results. Resolution is not as big a problem as shift, but all of these errors continue to increase as the frequency increases, until there is little signal left. At 3,700 cm$^{-1}$, most of this bandwidth is unusable due to the magnitude of water vapor. The actual cutoff for useful bandwidth is dependent on how well the details in water spectrum are compensated.

Transmission Quantification of OP-FTIR

The traditional quantification of OP-FTIR in absorbance space using Beer-Lambert's law requires the collection of a background spectrum $I_0(v)$. As discussed above, there are many problems with instrumental parameters and ambient temperature changing between the acquisition of the background and the analytical spectrum ($I_A(v)$). (Although both $I_A(v)$ and $I_0(v)$ are functions of frequency, for convenience, this term has been dropped in the notation to simplify the presentation.) Any changes between $I_0$ and $I_A$, other than due to the presence of the target gas, can create absorbance features and interfere with quantification. When parameters such as spectral shift, spectral resolution, and temperature change between $I_0$ and $I_A$, the resulting interference resembles noise in absorbance space. "Method noise" is the term used to describe this effect in the US-EPA Method TO-16, as discussed above. The addition of method noise increases the instrument's effective noise and decreases the ability of the OP-FTIR to accurately determine target gas concentrations.

Even if the instrumental parameters and temperature effects are completely accounted for in the reference transmission spectra, there are other ways that $I_0$ and $I_A$ can differ, such as the addition of subtraction of various particulates from the path. At a given field location, there is no way, short of using extensive alternate sampling devices along the beam path, to be sure of what gases and particles are present in the beam at that time. The "perfect" background spectrum remains elusive. Nevertheless, the use of a background for quantification is the predominant method conventionally used for most OP-FTIR data. It is important to understand that $I_0(v)$ and $I_A(v)$ are both implied functions of frequency in the discussion that follows.

Accordingly, the present novel technique was developed to eliminate the need for a background to quantify concentrations of several important gases from a single beam spectrum. Instead of using an absorbance spectrum as an input to a quantification method, the single beam analytical spectrum $I_A$ is used with transmittance reference spectra to determine concentrations. Once the concentration is known, the spectrum of the target gas can be removed from the single beam through division, and other gases can be quantified without interference. This method is successful at quantifying the most important interfering gas, water vapor and also has potential to quantify several target gases, such as $CH_4$ and $HN_3$.

Absorbance Vs. Transmission Space

The single beam spectrum is produced when the raw data from the OP-FTIR, the interferogram, is converted into wavenumber space by a FFT. This spectrum resembles a transmittance spectrum in that all of the gases have downward pointing peaks. The spectrum is a result of absorbance by everything from the source to the detector during the scan. The overall shape of the single beam spectrum is the shape of the energy profile of the source and the sensitivity of the detector. From this broad black-body-like feature, the losses at specific wave-numbers from gases and optical components result in downward pointing features.

Absorbance spectra are the result of an absorbance calculation that requires two single beam spectra to create a background ($I_0$) and an analytical spectrum ($I_A$), as follows:

$$A = -\ln(I_A/I_0) = \alpha(v)CL. \quad (12)$$

One important advantage of using absorbance is that it is linearly related to concentration, as stated by the Beer-Lambert law. A significant drawback to using absorbance in open-path spectroscopy is the inability to obtain the true $I_0$. In single beam transmission space the main advantage is that it represents a single scan. All instrumental and environmental parameters are therefore nearly static. Because concentration is non-linear and inversely related to transmission, this presents a minor problem compared to the relative advantages.

Transmission Revisited

Again, the frequency dependence of the transmission spectrum bears noting. As energy travels from the source to the detector, it encounters many surfaces and substances along the way. Reflection, refraction, absorption, interference, and diffraction of this energy alter the profile of the energy after it leaves the source. The impact of these phenomena can all be considered in terms of a percent transmission.

$$\% T = \frac{I_{SingleBeam}}{I_0} \times 100 \quad (13)$$

This percent transmission is actually a set of many percent transmissions for the many things that could interfere with the transmission of the beam.

$$I_{SingleBeam} = I_{Source} \times \%T_{Fixed\ Instrument} \times \%T_{Retro} \times \%T_{Particulates} \times \%T_{H_2O} \times \%T_{CO_2} \%T_{CH_4} \quad (14)$$

There are hundreds of gases and kinds of particles in any open path beam, and each has a separate % T that has a unique wavelength profile. For any given gaseous component, the following equation describes the relationship of its % T to the single beam:

$$I_{residual} = \frac{I_{SingleBeam}}{\% \ T_{ppm \cdot m}} \quad (15)$$

where $\% \ T_{ppm \cdot m}$=percent transmission at a given path integrated concentration; and $I_{residual}$=spectrum remaining after the gas is removed.

The key concept here is that the elimination of the target gas from the single beam spectrum can be achieved by division with a percent transmission or transmittance reference spectrum, with the appropriate path-integrated concentration. Finding the path-integrated concentration that minimizes the traces of the target gas in the residual spectrum thus yields the correct path-integrated concentration of the gas.

Transmission Quantification Method
Advantage of Removing Gases in Intensity Space The path-integrated concentration of a gas in a beam can be determined by finding the transmittance spectrum that removes any trace of the features of that gas from the single beam through division. This novel technique is generally analogous to the subtraction of the perfect absorbance reference spectrum from an absorbance spectrum created with a background spectrum. The temperature, spectral shift, and the spectral resolution can all be determined from the single beam, so excellent reference transmittance spectra can be created synthetically at any path-integrated concentration for several gases. Alternatively, suitable reference transmittance spectra can be obtained from carefully-controlled laboratory experiments. An important benefit of this technique is that the process of dividing out a synthetic reference spectrum can not add anything to the single beam spectrum; whereas, the use of a non-ideal background that may have contaminants or instrumental differences can easily add unknowns or extra method noise to the absorbance spectrum.

As noted above, water vapor is the most important absorber in the mid-infrared, and its elimination from the single beam spectra is a vital step for the quantification of many other gases. Therefore, water vapor is the first target gas for the transmission quantification algorithm. After correctly quantifying and removing water from the single beam spectra, the other gases can be quantified without this main interference. In an exemplary graph 210 illustrated in FIG. 9, the effect of dividing a single beam 212 by several water vapor reference transmission spectra 214, 216, and 218 is shown. Note that in transmission space and single beam intensity space, the peaks are negative. Also, all of these reference spectra are calculated at 64 meters, which is the path-length of the single beam for these data. The plot of the division by 7,000 ppm decreases the size of the transmission lines, but they are still present. The division by 14,000 ppm creates positive transmission lines in the residual, which is a result of dividing too much water vapor out of the spectrum and is analogous to negative absorbance, which is not possible. Since 7,000 ppm is too low and 14,000 ppm is too high, the correct concentration of water vapor in the path is between 7,000 ppm and 14,000 ppm. The plot of the division by 10,000 ppm is closer to the actual concentration, but still leaves small residual transmission lines. The ideal $I_0$ lies somewhere between the plots that represent the residuals of over and under quantifications of water vapor. It is important to note that these residual spectra still have all of the information from every other % T with which the beam interacted, and nothing is added to the residual, assuming that the temperature, shift, and resolution of the reference spectra were correctly matched to the sample spectrum.

Quantify Using Differential Intensity.

A method of determining path-integrated concentration and therefore, creating the best synthetic water vapor transmission spectrum for a given single beam was developed. This technique is similar to differential optical absorption spectroscopy (DOAS), but uses a much larger bandwidth than is typically used with DOAS. Traditional DOAS methods focus on a single feature and compare a small band or bands on the peak of a feature to other bands that are off-peak. Numerous different mathematical models have been tested and used over the years. The transmission quantification method described here is an integration of the DOAS idea over the large bandwidth that is available with OP-FTIR. Bandwidths hundreds of wave-numbers wide containing information from hundreds of individual absorption lines can be used with this approach. It must be emphasized that although the present novel approach was developed for use in processing an analytical spectrum produced by a Fourier transform infrared spectrometer, it can also be applied to processing the analytical spectrum produced by differential optical absorption spectrometer (with either an ultraviolet or visible light source), as well as the analytical spectrum produced by a Raman spectrometer.

The first step is to separate the points of the reference water transmittance spectra into two separate arrays depending on their relative transmittance. For the development and testing of the method, the band chosen was from $2,400 \ cm^{-1}$ to $3,300 \ cm^{-1}$. This band includes hundreds of water features. The method of separation that was chosen was a comparison of each transmittance point to a floating median of transmittance in wave-number space. Accordingly, each point of the transmittance spectrum is compared to the median of the transmittance points within a window around that point. If a point in the transmittance spectrum is below the median, then it has relatively low transmittance due to water absorption.

This comparison to the median finds all of the local maxima and minima in transmittance space. How local the maxima and minima are depends on the window width chosen. The minima in transmittance for a synthetic water spectrum are the result of peaks in absorbance. These points are therefore considered absorbers or more correctly "relative absorbers." The term "relative absorber" is more appropriate, since all points in the region have some absorbance. This concept is referred to above as the "water continuum spectrum." These points that are local minima in transmittance are contrasted with a similar array of points that represent local maxima in transmittance that indicate a lack of absorbance. The local maxima are the points that have transmittance values higher than the same floating median of transmittance. The points that are higher than the floating median are considered relative non-absorbers.

The use of a mean rather than a median for separation would have created some difficulties, because the sharp water lines would have resulted in many more non-absorbers. Having a median split provides equal numbers of absorbers and non-absorbers gives a more consistent distribution across the spectrum, which helps in the following steps, where a smoothing algorithm is applied to each array and large voids in either series would become a problem for the smoothing operation. However, it is important to emphasize that other values beside the median can be employed to dichotomize the spectrum, such as the geometric mean or other percentiles, without loosing the generality of the present novel analysis method.

FIG. 10 is an exemplary graph 220 that shows an area of the mid-infrared water vapor spectrum with a floating median separating the absorbers from the non-absorbers. An exemplary method uses a reference spectrum near the middle of the expected path-integrated concentration range to create these two opposing arrays, which appears to be a good choice, as with traditional spectroscopy, to have the reference(s) representing the expected range. The creation of a two mask function is the first step of the transmission quantification algorithm, as discussed herein.

The general shape of the infrared features of water vapor and other small molecules in the gas phase is conducive to the separation into relative more absorbing and less-absorbing arrays, because there are many sharp lines that create many local maxima and minima, which assures that both mask functions have good representation across the spectral band as seen clearly in FIG. 10. In contrast to this result, the median split separation of an infrared spectrum of a large molecule hydrocarbon in the C—H stretch region would only have a few local minima and maxima to exploit. The method would reduce to a basic peak/off peak DOAS approach when applied to gases with wide features.

Figure 9:
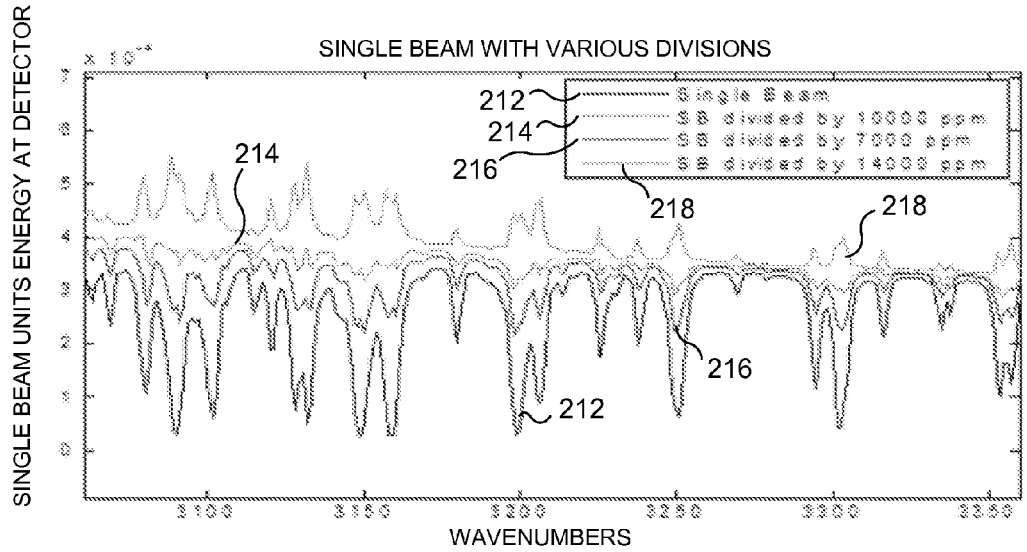
FIG. 9 is an exemplary schematic diagram illustrating the data processing pathways for both instrumental spectra creation and a synthetic spectrum creation.

The next step in the transmission quantification method is to take an input single beam intensity spectrum from the OP-FTIR and divide it by a series of transmittance spectra for water vapor. It may be desirable for the series to include path-integrated concentrations below and above the expected path-integrated concentration of the single beam input, to provide a margin of safety in obtaining the best accuracy. However, it should also be possible to interpolate or extrapolate the spectra based on only one or a few references, with some loss of accuracy. Of course this alternative would assume some model for how transmission changes with concentration if extrapolating beyond the range of the data. These transmittance spectra can be created from the HITRAN or other database with various software tools, or can be empirically determined using gas cells or other techniques. From the series of divisions, a series of residuals is created. A series of three division residuals is shown in FIG. 9. FIGS. 11A and 11B illustrate exemplary graphs 230 and 232, respectively, of a single beam input spectrum (FIG. 11A), and a transmittance reference spectrum (FIG. 11B), which are two inputs into the present novel transmittance quantification model.

The division of the single beam by a reference results in a residual as shown in an exemplary graph 234 in FIG. 12A. The mask functions contain a great deal of information about where in wave number space water vapor absorption will occur in the form of two "channels." The next step is to apply these channels to the input data. At this point, the two mask functions are applied to the residual of the divisions. The residuals are now split into two spectral arrays that are created by multiplying the residuals by each of the mask functions as shown in an exemplary graph 236 in FIG. 12B. These two spectral arrays are then smoothed, using a moving average over a window width, which is the same width as the moving median band width, as shown in an exemplary graph 238 in FIG. 12C.

The results of a division and smoothing process are shown in an exemplary graph 240 in FIG. 13, for a series of reference transmittance spectra. The references cover the range from 8,000 to 12,000 ppm at 64 meters. The plots in the upper boxes represent the transmittance reference spectra for the band from 3100 cm$^{-1}$ to 3180 cm$^{-1}$. The concentration increases from left to right, and the features therefore become larger (smaller numerically). The lower boxes in graph 240 represent a residual 242 of a synthetic single beam sample spectra divided by the corresponding reference above it. Also shown are less absorbing smoothed spectra 244, and more absorbing smooth spectra 246. The X-axis is identical for the upper and lower boxes. The input single beam represents 64 meters and 10,000 ppm water vapor. In the center frame, both the reference and sample have the same path integrated concentration. It can be seen in this frame that the two smoothed arrays are practically collinear. Therefore, the total differential intensity $I_D$ between them is zero, and there is no differential absorption due to water and thus, no water in the residual.

For the quantification algorithm, the total differential intensity is plotted against the path integrated concentration of the input reference spectra, as indicated by the following relationship.

$$I_D = \sum_{j=v_1}^{j=v_2} (I_{moreABS,j} - I_{lessABS,j}) \quad (16)$$

Concentration Vs. Total Differential Intensity

The quantity chosen to compare the residuals is the sum of a simple point-by-point subtraction of the entire smoothed more-absorbing spectra from the smoothed less-absorbing spectra. This quantity is referred to herein as "the total differential intensity," $I_D$, as defined in Eq. (16) above. When this quantity is plotted against the path-integrated concentration of the divisor reference transmittance spectra, the relationship is monotonic and slightly quadratic, as shown in an exemplary graph 250 in FIG. 14.

The path-integrated concentration can be determined from the plot as the point where the total differential intensity is minimized. The correct point in path-integrated concentration does not exactly correspond to the zero $I_D$ due to the shape of the single beam. There is a slight bias due to the relationship between the two arrays and the shape of the instrumental spectrum, which is illustrated for a region of the spectrum where the instrument response changes significantly, in an exemplary graph 252 in FIG. 15. This bias is determined by calculating the same $I_D$ on an estimated $I_0$. Essentially, the calculation uses an estimated $I_0$ as an input spectrum and creates the two arrays, smoothing them and calculating the total differential intensity, which typically introduces a small error, but the error is still important. In a region of the spectrum with no change in instrumental function with wave-number, this error would trend towards zero.

The path-integrated concentration of the gas is determined from the regression line of total differential intensity in the residual vs. path-integrated concentration of water in the divisor reference spectrum (FIG. 14). A quadratic fit was chosen due to significant improvements over a linear fit. Table 2 shows that the addition of a quadratic term caused small but significant improvements and the addition of higher order terms was insignificant.

TABLE 2

Determination of best degree polynomial for quantification.
Percent change from convergence with added degree of polynomial

| | linear | quadratic | cubic | 4th power |
|---|---|---|---|---|
| | Methane concentration from Yakima data | | | |
| 1171 cm$^{-1}$ to 1219 cm$^{-1}$ | 0.4 | 0.02 | 0 | 0 |
| 2906 cm$^{-1}$ to 3292 cm$^{-1}$ | 1.38 | 0.04 | −0.01 | 0 |
| | Water concentration from Yakima data | | | |
| 1171 cm$^{-1}$ to 1219 cm$^{-1}$ | 0.59 | 0 | 0 | 0 |
| 2906 cm$^{-1}$ to 3292 cm$^{-1}$ | 2.02 | 0.03 | 0 | 0 |

The concentration of a gas is determined by using a quadratic fit on the relationship between $I_D$ and reference divisor concentration while setting $I_D$ to the bias value determined from the single beam, as shown in FIG. 15. This regression line predicts the point in path-integrated water vapor concentration where the more absorbing pixels and the less absorbing pixels of the single beam divided by the synthetic water reference smooth to the same line.

Testing of Quantification Method
Testing Against Noise

In order to determine the robustness of this quantification technique in the field, Gaussian noise was added to synthetic single beams at various levels to determine the potential magnitude of the errors introduced into the path-integrated concentration prediction. FIG. 16 includes an exemplary graph 254 showing a small region of the spectrum with a wide range of different noise levels added. The noise was measured as RMS noise in absorbance units from US-EPA Method TO-16, in the wave-number region 2,480 $cm^{-1}$ to 2,520 $cm^{-1}$. The data were calculated for the synthetic noise added spectra by creating two synthetic single beam spectra with equal noise added and creating an absorbance file from them. A linear regression on the 80 points around 2,500 $cm^{-1}$ was then performed. The differences from this line were then all squared. The mean of these squared differences was then calculated. The square root of this mean is the value used for RMS noise.

The effect of window size on the ability to quantify water vapor was also investigated by running the algorithm with median split window sizes of 24.1 $cm^{-1}$, 48.2 $cm^{-1}$, and 96.4 $cm^{-1}$ at all noise levels, which respectively corresponds to 50, 100, and 200 points, with the data spacing of 0.48 $cm^{-1}$ that was used throughout the field and synthetic data in this disclosure. The spectral region used in the quantification was from 2,400 $cm^{-1}$ to 3,300 $cm^{-1}$. These spectra are a result of the water vapor absorptions as determined by E-Trans™, and the Gaussian noise added with MATLAB™ being superimposed on the instrumental spectrum of the AirSentry™ OP-FTIR. The results are summarized in exemplary graphs 256 and 258, which are respectively shown in FIGS. 17 and 18. The algorithm is robust to the effects of noise when quantifying water vapor. Transmission quantification was able to quantify water vapor within 1%, up to noise levels of 100 times the expected noise level in a typical OP-FTIR ($10^{-2}$ absorbance units). There were slight differences in the predictions across the median split window sizes, but they were not significant. In FIGS. 17 and 18, the means for each of 15 separate runs are plotted at each noise level, with the standard deviations shown by the error bars. The X-axis is RMS noise determined by performing EPA defined RMS noise calculations on the absorbance file created from them in the 2500 $cm^{-1}$ region. The Y-axis represents actual and predicted water path-integrated concentrations.

Testing Against Sinusoidal Interference

The next test for transmission quantification was the introduction of sinusoidal functions onto the single beam spectra before quantification. In the field, an OP-FTIR can encounter particulate matter, droplets of water, or other optical interference that can change the shape of the single beam spectra, often introducing broadband waves of interference and making a given background inappropriate. Traditional Beer's law-based quantification techniques deal with this issue by doing a baseline correction to the absorbance spectrum. To investigate these effects on the ability of transmission quantification to predict the correct path-integrated water vapor concentration, a multitude of sinusoidal functions were added to synthetic single beam spectra before quantification. These sinusoidal interfering functions had a magnitude of 10% of the signal and resembled strong particulate scattering that is sometimes seen in the field. The wavelength was varied from 2.4 $cm^{-1}$ to 240 $cm^{-1}$, and the phase offset was varied from 0 to $2\pi$. FIG. 19 includes an exemplary graph 260, which shows an example of a single beam before and after the addition of sinusoidal interference functions with wavelengths of 240 $cm^{-1}$ and 120 $cm^{-1}$. The translation effect of changing the phase offset of the interfering function on the single beam spectra is illustrated in an exemplary graph 262, in FIG. 20.

The transmission quantification algorithm handled the added sinusoidal interferences well, predicting path-integrated concentrations within 1% as long as the wavelength of the interfering wave was above 40 $cm^{-1}$. Varying phase resulted in considerable systematic changes in the predicted water path-integrated concentration, but was important only with shorter wavelength interference. In FIG. 21, each point in frequency space of an exemplary graph 264 represents the standard deviation of predicted path-integrated concentration across all phases as a percentage of the true value in the synthetic spectra. FIG. 22 is an exemplary graph 266, which shows several plots across phase space, each at a specific wavelength. The trend toward better accuracy with increasing wavelength can be seen in both FIGS. 21 and 22. Depending on the phase offset, the predictions can be over or under the actual path-integrated concentration at the same wavelength. The effect of sinusoidal interference of varying frequency and phase on the ability on the transmission quantification method to predict the concentration of water vapor in synthetic spectra is illustrated in an exemplary three-dimensional graph 268, which is shown in FIG. 23.

The effect on transmission quantification of sinusoidal interference of the single beam spectrum is minimal for large interfering features. As long as the window size is smaller than the frequency of the interfering signal the algorithm is very accurate. High frequency interference can pose problems. When frequencies smaller than the window size used in the median and smoothing process are added to the single beam spectrum, significant errors can arise. Both phase and frequency are important in the manifestation of this effect. Errors of up to 20% in predicted concentration were observed in some of the simulations. Therefore to minimize possible errors, the window size should be selected to be smaller than interfering features that are expected in the single beam spectrum, but also should be larger than the absorbing feature size (typically measured by the full-width, half-maximum of absorbance lines) for the target gas species in the analysis. Selection of the window size is guided by the need to minimize interference, while still being able to analyze the target gas by separating absorbing and non-absorbing regions in the spectrum.

Testing Against Interference from Other Gases

An important source of interference with OP-FTIR data is the interference by other gases that absorb infrared radiation at the same wavelengths as the target gas. This problem is commonly addressed by including likely interfering species in a classic or partial least squares quantification technique in absorbance space. If the method of transmission quantification is to be effective, it must also be able to deal with this problem. Water vapor and methane both have many overlapping absorption lines in the region of the spectrum from 2,800 $cm^{-1}$ to 3,300 $cm^{-1}$. To evaluate the effects of these interferences on the quantification of each gas, synthetic single beam spectra were created with varying amounts of both gases using E-Trans™ software. The simulation uses the actual concentrations encountered in the field at the Yakima, Wash. Airport in July, 2006, where methane and water vapor were both present. As can be seen in an exemplary graph 270 that is illustrated in FIG. 24, the addition of water vapor to the spectrum causes the transmission quantification method to decrease the predicted methane concentration. Methane has a similar effect on water vapor as seen in an exemplary graph 272, as illustrated in FIG. 25. This result is due to the water absorbing more in the regions of the spectrum assigned to the less absorbing array in the methane transmission quantification. Since the water vapor model is built from pure water spectra (no methane), the relative amount of transmission in the two quantifying arrays (more absorbing and less absorbing) when methane is present results in errors in the determination of water vapor concentration.

A good way to deal with this problem is via stepwise quantification with iteration. As mentioned above, water vapor has more influence on the single beam spectra than other gases and should be quantified first and, subsequently, removed from the spectra first. The spectrum that remains is referred to as the "residual spectrum."

In absorbance space, using the traditional Beer's law CLS or PLS methods of quantification, all of the gases are typically quantified at the same time, creating a single residual spectrum. Sometimes minimization of the residual spectrum is the goal of these algorithms. The residual is created by subtracting all of the quantified gases out of the absorbance spectrum. To do this, a spectrum for each gas needs to be created by interpolating reference spectra to the proper concentration that was found in the sample. When these absorbance spectra are all subtracted from the input absorbance spectra of the sample, what remains is the residual.

The transmission quantification algorithm also uses residuals to determine concentration. As described above, the concentration of a gas as determined by this method is the concentration that just fully removes that gas from the residual of the single beam divided by a transmission spectrum. As the concentration of a gas is determined, the residual single beam spectrum is created that still contains information about all of the other gases, as stated above in Eq. (15). Once the features from the first gas are removed, the second gas can be more accurately determined.

This stepwise quantification should be done in order of decreasing concentration. The removal of gas #1 from the single beam spectrum makes the prediction of gas #2 more accurate; however, there is a small error remaining as the concentration of gas #1 was determined with some of gas #2 in the beam. This problem can be solved by iterating through the gases until the change in predicted concentration from the last prediction is insignificant.

The process suggested above is stepwise quantification. First the most abundant gas, water vapor, is quantified from the input single beam spectrum, and a residual single beam spectrum is created based on this predicted concentration. The input spectrum has many gases other than the water vapor, so the water vapor prediction is not as accurate as possible. Next, the second gas (methane in the example) is quantified from the residual single beam spectrum. The methane prediction is affected by any other gases that may be in the spectrum and by the water vapor error from the inaccuracies from the first guess of water vapor. This process of first estimation continues for all of the gases being quantified. After this point, the process is repeated starting again with water vapor. This time the first estimations of all of the other gases are removed from the input spectrum so the prediction is more accurate. The process is repeated until the changes from prediction n to prediction n+1 are not significant.

To test this method, synthetic single beam spectra were created with 11,000 ppm water vapor and 2.5 ppm methane with various amounts of noise. The noise ranged from $10^{-3}$ to $10^{-2}$ absorbance units and caused some errors in the final predicted concentrations. The level of noise did not change the number of iterations needed to converge. All runs required only four iterations before the change in predicted concentration was below 0.001% (and therefore, the results were acceptably accurate).

TABLE 1

Percent change from iteration for water vapor and methane quantification.

| | Step 2 % change | Step 3 % change | Step 4 % change |
|---|---|---|---|
| Water 11,000 ppm | 3.58 | 0.0365 | 0.0004 |
| Methane 2.5 ppm | 0.89 | 0.0096 | 0.0001 |

Testing Against Shift and Resolution

The final synthetic test for the transmission quantification algorithm was to have input single beam spectra that are not matched to the input reference spectra in terms of resolution and spectral shift. It is possible to determine these quantities "a priori" from the single beam, but the sensitivity is still of interest, since the accuracy of the pre-determined spectral shift and resolution is not perfect.

In the first simulation, synthetic single beam spectra were created containing 2.5 ppm methane, with spectral shifts of $-0.5$ cm$^{-1}$ to 0.5 cm$^{-1}$. The spectral shifts are measured relative to the spectral shifts of the methane references used in the transmission quantification algorithm. This range is larger than would be expected from an OP-FTIR in the field under most circumstances. The other parameters were held constant and included a spectral resolution of 1.2 cm$^{-1}$, temperature of 295° K and a path-length of 64 meters. Based upon an exemplary graph 274 in FIG. 26, it is clear that no significant errors will result in predicted concentration, unless the OP-FTIR has an abnormal amount of shift during the experiment. The observed range of spectral shift in the instrument is not close to the amount needed to create a one percent 1% change in predicted concentration. A difference in shift causes an underestimation of concentration by the transmission quantification method regardless of the shift difference being positive or negative.

In the final simulation synthetic single beam spectra were created containing 2.5 ppm methane with spectral resolutions from 0.97 cm$^{-1}$ to 1.4 cm$^{-1}$. Resolutions finer than 0.97 cm$^{-1}$ are not possible with a nominal resolution of 1 cm$^{-1}$. The upper limit of 1.4 cm$^{-1}$ is higher than has been seen with the ETG AirSentry™ and close to the limit of acceptance for a spectrometer with a nominal resolution of 1 cm$^{-1}$. For the simulation, a reference library was created at 1.2 cm$^{-1}$, and the spectral shift and all other parameters were held constant for the references and the input single beam spectra. An exemplary graph 276, which is illustrated in FIG. 27, shows that resolution effects over the entire expected range will not cause errors in predicted concentration much above 1%. There is a general relationship of finer resolution resulting in over prediction of concentration with this method and coarser resolution resulting in under predicting concentration. The robustness to resolution errors are due in part to the fact that a resolution change of the input spectra does not result in transmission points in wave-number space changing relative transmission; but, only the absolute transmission is affected. The peaks get weaker and spread out but they are still peaks.

Testing Against Yakima Dataset

The exemplary novel transmission method was used to generate water vapor concentrations for the Yakima, Wash. Airport dataset. The absolute humidity was calculated from the relative humidity and the temperatures recorded by the airport meteorological station. A window width of 48 cm$^{-1}$ was used on the band from 1,171 cm$^{-1}$ to 1,267 cm$^{-1}$. Exemplary graph 278 in FIG. 28 shows this comparison. The reference spectra used in the quantification of these data were all at 295° K. In an exemplary graph 280 in FIG. 29, the errors from the quantification are plotted against the temperature from the airport meteorological station. The extremely high correlation indicates that when the set of reference spectra are used with the proper temperature, very little error will remain.

The quantification of the Yakima dataset was repeated with temperature compensation. Each analytical single beam intensity spectrum was quantified using transmittance references created with the optically derived temperature from that spectrum. FIG. 30 illustrates the temperature-compensated concentration calculations in an exemplary graph 282. The data are smoothed and compared to the airport meteorological station. The temperature correction brings the transmission quantification much closer to the airport data, as expected.

Logical Steps for Implementing Novel Approach

FIGS. 31 and 32 respectively include a flowchart 300 and a schematic block diagram 350 that illustrate exemplary logical steps and other details of the process for implementing the present novel approach for determining the concentration of an absorbing specie from an analytical spectrum 312 and a series of transmittance reference spectra data 302, examples of which are shown in FIG. 32 as transmittance reference spectra 354a, 354b, and 354c. The analytical spectrum can be in any region of the electromagnetic spectrum and have the units of intensity vs. wavelength. The transmittance spectra can be synthetic (such as derived from the HITRAN database, as discussed above) or created from known samples using an empirical approach. A step 304 in FIG. 31 uses the transmittance reference data spectra to create two mask functions (as discussed above, in connection with FIG. 10). In this step, a moving median is used to divide the individual points along the wavelength axis into "more absorbing" and "less absorbing" points, producing two mask arrays 308 of which each point has the value 1 or 0. A step 306 then divides the analytical spectrum by each of the series of transmittance spectra, producing spectral residuals 314 from the division, one for each reference spectra. Next (in FIG. 31), a step 310 multiplies each residual 314 by both mask functions created in step 304 and removes all zeros from the results, producing two arrays 316 for each input reference spectra, including an array 364 that represents the spectra of only the more absorbing points after the division, and an array 362 that represents the spectra of only the less absorbing points (FIG. 32).

In a step 318, all of arrays 316 are now smoothed using a moving mean that fills in the voids created by removing the zeros and creates opposing values at each wavelength, producing smoothed absorbing and non-absorbing residuals 320. For each input reference spectra, the quantity "Differential Intensity," $I_D$ is determined by subtracting the absorbing smoothed masked residual from the non-absorbing smoothed masked residual in a step 322. The result of this step is a series of values 324 for $I_D$ for different reference concentrations. Graph 250 in FIG. 10 illustrates examples of such values and illustrates a next step 326, which provides for solving for a concentration 328 (regress for $I_D$=0). The point where $I_D$=0 represents the determined concentration of the absorbing specie in the analytical spectrum. In a step 330, a transmittance spectrum is created for the calculated concentration by interpolating the reference spectra bracketing the determined concentration. A step 332 provides that the analytical spectrum is then divided by the transmittance spectrum created in step 330, resulting in a residual spectrum 370 (FIG. 32) that is free of the absorbing specie quantified and ready for further analysis. As noted in a step 334, this residual can be used in repeating the steps, starting with step 310, to determine the concentration of the next gas—until there are no other gases for which a concentration will be determined by this novel approach.

Applicability to Processing an Input Sample from Other Types of Spectrometer

The Transmission quantification technique described here requires an input sample spectrum from a broadband spectrometer of some kind and at least one transmission spectrum of the absorbing species that is to be quantified. It is again emphasized that the input sample spectrum could be from an FTIR spectrometer or an ultraviolet (UV) or visible (VIS) light Differential Optical Absorption Spectrometer (DOAS). The transmission spectrum or series of reference transmission spectra can be obtained from a spectrometer or synthetically created from known coefficients. Providing more spectra and spectra that are closer to the sample concentration are desirable for producing a better result.

Processing of ultraviolet or visible wavelength DOAS spectra would proceed in the same way as for FTIR data processing, if the sample data are in the form of a single beam intensity spectrum and if the references are available in the form of transmission spectra. If the reference spectra are in the form of "derivative" transmission spectra, then the it would be appropriate to first integrate the derivative references to produce transmission references, before proceeding in the manner discussed above and dividing the reference spectra into the single beam sample spectrum. Alternatively, the derivative of the single beam sample spectrum can be computed and then divided by the derivative reference spectra for quantification; however, this approach is less desirable because it will enhance noise in the single beam sample spectrum, and degrade the signal-to-noise ratio, potentially decreasing the sensitivity of the present approach.

Experimental Limitations

The experimental data used to test the transmission quantification technique were collected in a single 14 hour period, which is a very limited sampling domain. Also the pathlength was only 32 meters each way, for a total of 64 meters. Typically much longer paths are used in the field.

Another limitation of the experimental data is the accuracy of the water content data from the airport meteorological station. The synthetic simulations suggest that the OP-FTIR can quantify water with an accuracy of a tiny fraction of a percent. The meteorological station relative humidity and temperature equipment is only accurate to 2% at best. To properly assess the accuracy of this novel approach, field comparisons should be made against far more accurate reference data. Another limitation is that the sampling interval for the airport was one hour, and the spectral data interval was nine minutes after averaging. The time averaging alone could prevent the two measuring devices from agreeing within more than 1% of each other. This problem prevents a real test of the limits of the transmission quantification technique. Water vapor and methane were the only gases tested empirically using this novel approach, and there was only synthetic data to test the methane concentration predictions. This approach should be equally applicable for determining the concentration of a number of other gases with distinctive absorption lines, such as ammonia, carbon monoxide, $NO_x$, sulfur dioxide, ozone, and many other gases. In contrast, it is likely that the novel method described herein using a median split of the residuals to evaluate concentration will not be very effective for determining the concentration of those gases that have only broad absorbance features. In the case of gases with such broad absorbance features, transmission quantification can still be applied, but another method of minimizing the residuals in the single beam spectrum should be applied, by computing the first or higher-order derivative of both the sample and reference spectra before applying the described quantification method. Alternatively, another method of minimizing the residuals in the single beam spectrum could be applied, such as a least-squares or partial least squares approach. Gases with broad absorbance features include many important hydrocarbons that are of great interest in the field of air quality. However, the proper quantification of water vapor and other gases comprising small molecules will help to solve the problem of interference when determining the concentration of gases having the broad absorption features.

Exemplary Computing Device for Use in Practicing the Method

FIG. 33 schematically illustrates an exemplary system 450 suitable for implementing the present novel technique. Computer 464 may be a generally conventional personal computer (PC) such as a laptop, desktop computer, server, or other form of computing device. Computer 464 is coupled to a display 468, which is used for displaying text and graphics to the user. Included within computer 464 is a processor 462. A memory 466 (with both read only memory (ROM) and random access memory (RAM)), a non-volatile storage 460 (such as a hard drive or other non-volatile data storage device) for storage of data and machine readable and executable instructions comprising modules and software programs, and digital signals, a network interface 452, and an optical drive 458 are coupled to processor 462 through a bus 454. Data that are stored can include the analytical spectrum (or the spectrum can be input in real-time from the detector for processing in accord with the novel approach), as well as the transmittance reference data. Any of these data can alternatively be accessed over a network 470, such as the Internet or other network, through network interface 452. Optical drive 458 can read a compact disk (CD) 456 (or other optical storage media, such as a digital video disk (DVD)) on which machine instructions are stored for implementing the present novel technique, as well as other software modules and programs that may be run by computer 464. The machine instructions are loaded into memory 466 before being executed by processor 462 to carry out the steps for implementing the present technique, e.g., carrying out divide, multiply, and subtraction steps, as discussed above. The user can provide input to and/or control the process through keyboard/mouse 472, which is coupled to computer 464.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for determining, using a computing device, an actual concentration of a gas in a path, the method comprising the steps of:
   coupling an output from a spectrometer to the computing device;
   storing on the computing device, reference transmittance data for at least one concentration of the gas and a sample input signal corresponding to an analytical spectrum ($I_A$) of light that has propagated along the path, the analytical spectrum corresponding to light absorbed along the path;
   dividing, using the computing device, the analytical spectrum by the reference transmittance data to determine a plurality of residual spectra, including a residual spectrum for each concentration in the reference transmittance data;
   separating, using the computing device, each of the residual spectra into absorbing and non-absorbing residual portions; and
   identifying, out of the plurality of residual spectra, a residual spectra with a minimum difference between absorbing and non-absorbing portions; and
   determining, from the residual spectra with the minimum difference and without a background spectrum $I_0$, the actual concentration of the gas in the path.

2. The method of claim 1, wherein the absorbing and non-absorbing portions are separated by comparing transmittance points in the reference transmittance data to a median of transmittance.

3. The method of claim 2, wherein the median is a floating median defined by a discrete window around the transmittance points.

4. A method for determining an actual concentration of a gas in a path, the method comprising the steps of:
   providing, using a spectrometer, an optically derived analytical spectrum ($I_A$) for the path, and transmittance reference data for the gas, wherein the transmittance data comprises a plurality of transmittance spectrum for each of a corresponding plurality of different concentrations of the gas, and wherein the analytical spectrum corresponds to light absorbed along the path;
   dividing the analytical spectrum by the transmittance spectrum for each of the plurality of different concentrations of the gas, to determine residual spectra for the different concentrations of the gas;
   using mask functions derived from the transmittance reference data, separating each of the residual spectra into absorbing and non-absorbing residual portions;
   smoothing the absorbing and non-absorbing residual portions to produce smoothed absorbing and non-absorbing residual portions; and
   determining an actual concentration of the gas in the path without a background spectrum $I_0$ by identifying the concentration of the gas for which a difference between the smoothed absorbing and non-absorbing residual portions is a minimum compared to differences between the smoothed absorbing and non-absorbing residual portions for other concentrations of the gas.

5. The method of claim 4, further comprising the step of determining an absorbing mask function and a non-absorbing mask function from the reference transmittance data.

6. The method of claim 5, wherein the step of determining the absorbing mask function and the non-absorbing mask function comprises the step of comparing each transmittance point of a reference transmittance spectrum to a floating median of transmittance within a window around that transmittance point, wherein the absorbing mask is based on the transmittance points that are on one side of the floating median, and the non-absorbing mask is based on the transmittance points on an opposite side of the floating median.

7. The method of claim 4, wherein the step of using the mask functions comprises the step of multiplying each of the residual spectra by the mask functions, to produce the absorbing and non-absorbing residual portions.

8. The method of claim 7, further comprising the step of removing specific values after multiplying each of the residual spectra by the mask functions, to produce the absorbing and non-absorbing residual portions.

9. The method of claim 4, wherein the step of determining the actual concentration of the gas in the path by identifying the concentration of the gas for which a difference between the smoothed absorbing and non-absorbing residual portions is a minimum comprises the step of subtracting the smoothed absorbing residual portions spectra from the non-absorbing smoothed portions for each of the different concentrations of the gas to determine a differential intensity.

10. The method of claim 9, wherein the step of determining the actual concentration of the gas in the path by identifying the concentration of the gas for which a difference between the smoothed absorbing and non-absorbing residual portions is a minimum further comprises the step of selecting the concentration of the gas that minimizes the differential intensity.

11. The method of claim 4, further comprising the step of interpolating the transmittance reference spectra to create an interpolated transmittance spectra for the actual concentration of the gas that was determined.

12. The method of claim 11, further comprising the step of dividing the analytical spectrum by the interpolated transmittance reference spectrum to determine a new residual spectrum that can be used for determining a concentration of a different gas in the path.

13. The method of claim 4, further comprising the step of creating the analytical spectrum by directing light along the path and obtaining the analytical spectrum using a spectrometer selected from a group of spectrometers consisting of:
    a Fourier transform infrared spectrometer;
    an ultraviolet absorption spectrometer;
    a visible light spectrometer; and
    a Raman spectrometer.

14. A non-transitory computer readable medium encoded with a computer program containing instructions stored therein for causing a computer processor to perform a plurality of functions to determine an actual concentration of a gas in an path using an optically derived analytical spectrum ($I_A$) for the path, and using transmittance reference data for the gas, wherein the transmittance data comprise a plurality of transmittance spectrum for each of a corresponding plurality of different concentrations of the gas, and wherein the analytical spectrum corresponds to light absorbed along the path, said plurality of functions including:
    coupling with an output from a spectrometer to the computing device;
    dividing the analytical spectrum by the transmittance spectrum for each of the plurality of different concentrations of the gas, to determine residual spectra for the different concentrations of the gas;
    using mask functions derived from the transmittance reference data, separating each of the residual spectra into absorbing and non-absorbing residual portions;
    smoothing the absorbing and non-absorbing residual portions to produce smoothed absorbing and non-absorbing residual portions; and
    determining an actual concentration of the gas in the path without a background spectrum $I_0$ by identifying the concentration of the gas for which a difference between the smoothed absorbing and non-absorbing residual portions is a minimum compared to differences between the smoothed absorbing and non-absorbing residual portions for other concentrations of the gas.

15. A system for determining an actual concentration of a gas in a path using an optically derived analytical spectrum ($I_A$) for the path, and using transmittance reference data for the gas, wherein the transmittance data comprise a plurality of transmittance spectrum for each of a corresponding plurality of different concentrations of the gas, and wherein the analytical spectrum corresponds to light absorbed along the path, the system comprising:
    a memory in which are stored the transmittance data, and a plurality of machine executable instructions;
    an input port coupled to a spectrometer output to receive an input signal corresponding to the analytical spectrum; and
    a processor that is coupled to the memory and the input port, the processor executing the machine executable instructions to carry out a plurality of functions, including:
        dividing the analytical spectrum by the transmittance spectrum for each of the plurality of different concentrations of the gas, to determine residual spectra for the different concentrations of the gas;
        using mask functions derived from the transmittance reference data, separating each of the residual spectra into absorbing and non-absorbing residual portions;
        smoothing the absorbing and non-absorbing residual portions to produce smoothed absorbing and non-absorbing residual portions; and
        determining an actual concentration of the gas in the path without a background spectrum $I_0$ by identifying the concentration of the gas for which a difference between the smoothed absorbing and non-absorbing residual portions is a minimum compared to differences between the smoothed absorbing and non-absorbing residual portions for other concentrations of the gas.

16. The system of claim 15, wherein the execution of the machine executable instructions by the processor further causes the processor to carry out the function of determining an absorbing mask function and a non-absorbing mask function from the reference transmittance data.

17. The system of claim 16, wherein the execution of the machine executable instructions by the processor further causes the processor to carry out the function of comparing each transmittance point of a reference transmittance spectrum to a floating median of transmittance within a window around that transmittance point, wherein the absorbing mask is based on the transmittance points that are on one side of the floating median, and the non-absorbing mask is based on the transmittance points on an opposite side of the floating median.

18. The system of claim 15, wherein the execution of the machine executable instructions by the processor further causes the processor to carry out the function of multiplying the residual spectra by the mask functions, to produce the absorbing and non-absorbing residual portions.

19. The system of claim 18, wherein the execution of the machine executable instructions by the processor further causes the processor to carry out the function of removing zeroes after multiplying the residual spectra by the mask functions, to produce the absorbing and non-absorbing residual portions.

20. The system of claim 15, wherein the execution of the machine executable instructions by the processor further causes the processor to carry out the function of subtracting the smoothed absorbing residual portions from the non-absorbing smoothed portions for each of the different concentrations of the gas to determine a differential intensity.

21. The system of claim 20, wherein the execution of the machine executable instructions by the processor further causes the processor to carry out the function of selecting the concentration of the gas that minimizes the differential intensity, to determine the actual concentration of the gas in the path.

22. The system of claim 15, wherein the execution of the machine executable instructions by the processor further causes the processor to carry out the function of interpolating the transmittance reference spectra to create an interpolated transmittance spectra for the actual concentration of the gas that was determined.

23. The system of claim 22, wherein the execution of the machine executable instructions by the processor further causes the processor to carry out the function of dividing the analytical spectrum by the interpolated transmittance reference spectrum to determine a new residual spectrum that can be used for determining a concentration of a different gas in the path.

24. The system of claim 15, further including a spectrometer that produces the input signal corresponding to the analytical spectrum, wherein the spectrometer is selected from a group of spectrometers consisting of:
a Fourier transform infrared spectrometer;
an ultraviolet absorption spectrometer;
a visible light spectrometer; and
a Raman spectrometer.

* * * * *